United States Patent
Barbosa et al.

(10) Patent No.: US 7,300,949 B2
(45) Date of Patent: Nov. 27, 2007

(54) THIAZOLOPYRAZOLES AND METHODS OF THEIR USE

(75) Inventors: Joseph Barbosa, Lambertville, NJ (US); Cynthia A. Fink, Lebanon, NJ (US); Spencer D. Kimball, East Windsor, NJ (US); Hartmuth Kolb, Marina Del Rey, CA (US); Zhi-Cai Shi, Monmouth Junction, NJ (US); Ashok R. Tunoori, East Windsor, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 446 days.

(21) Appl. No.: 11/094,241

(22) Filed: Mar. 31, 2005

(65) Prior Publication Data

US 2005/0282874 A1    Dec. 22, 2005

Related U.S. Application Data

(60) Provisional application No. 60/557,699, filed on Mar. 31, 2004.

(51) Int. Cl.
C07D 513/02    (2006.01)
A61K 31/429    (2006.01)

(52) U.S. Cl. ................................. 514/366; 548/153
(58) Field of Classification Search ................ 514/366; 548/153
See application file for complete search history.

(56) References Cited

U.S. PATENT DOCUMENTS 6,566,363 B2 *    5/2003    Chong et al. .......... 514/254.04
2002/0049215 A1    4/2002    Chong et al.

FOREIGN PATENT DOCUMENTS

WO    WO 02/12250 A2    2/2002

OTHER PUBLICATIONS

International Search Report, International Application No. PCT/US05/010956, Mar. 31, 2005.

* cited by examiner

*Primary Examiner*—Kamal A. Saeed
(74) *Attorney, Agent, or Firm*—Max Bachrach

(57) ABSTRACT

This invention concerns novel thiazolopyrazole compounds and compositions comprising them. Methods of using these compounds for the treatment, prevention and management of various diseases and disorders are also encompassed by the invention.

18 Claims, No Drawings

THIAZOLOPYRAZOLES AND METHODS OF THEIR USE

This application claims priority to U.S. Provisional application No. 60/557,699, filed Mar. 31, 2004, the entirety of which is incorporated herein by reference.

1. FIELD OF THE INVENTION

This invention relates to novel thiazolopyrazoles and methods of their use for the treatment, prevention and management of various diseases and disorders.

2. BACKGROUND OF THE INVENTION

Protein Kinases (PKs) are enzymes that catalyze the phosphorylation of hydroxyl groups on tyrosine, serine and threonine residues of proteins. The phosphorylation of proteins modulates various cell activities such as cell growth, differentiation and proliferation. Abnormal PK activity has been linked to a host of disorders, ranging from relatively non-life threatening diseases such as psorisasis to extremely virulent diseases such as glioblastoma (brain cancer).

A great deal of effort has been expended in an attempt to identify ways to modulate PK activity. Examples are: biomimetic approaches using large molecules patterned on those involved in the actual cellular processes (e.g., mutant ligands (U.S. Pat. No. 4,966,849); soluble receptors and antibodies (WO 94/10202, Kendall et al., *Proc. Nat'l Acad. Sci.*, 90: 10705-09 (1994), Kim et al., *Nature*, 362: 841-844 (1993)); RNA ligands (Jelinek et al., *Biochemistry*, 33: 10450-56); Takano et al., *Mol. Bio. Cell*, 4: 358A (1993); Kinsella et al., *Exo. Cell Res.*, 199: 56-62 (1992); Wright et al., *J. Cellular Phys.*, 152: 448-57); and tyrosine kinase inhibitors (WO 94/03427; WO 92/21660; WO 91/15495; WO 94/14808; U.S. Pat. No. 5,330,992; Mariani et al., *Proc. Am. Assoc. Cancer Res.*, 35: 2268 (1994)). Despite such attempts, a need still exists for effective methods of modulating PK activity.

3. SUMMARY OF THE INVENTION

This invention encompasses compounds of formula (1):

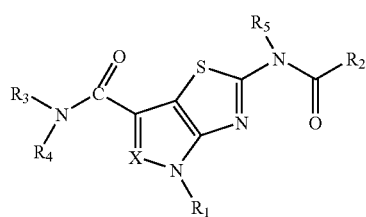

(1)

wherein:

X is CH or N;

$R_1$, $R_3$ and $R_4$ are each independently H, optionally substituted alkyl, optionally substituted alkenyl, optionally substituted alkynyl, optionally substituted aryl, optionally substituted heteroaryl, optionally substituted heterocycloalkyl, optionally substituted heterocycle, optionally substituted arylalkyl, optionally substituted heterocycloalkylalkyl, optionally substituted heteroarylalkyl, optionally substituted alkoxycarbonyl, optionally substituted aminocarbonyl, optionally substituted carbonyl, or optionally substituted sulfonyl; or $R_3$ and $R_4$, with the nitrogen to which they are attached, form an optionally substituted heterocycle;

$R_2$ is H, optionally substituted alkyl, optionally substituted alkenyl, optionally substituted alkynyl, optionally substituted aryl, optionally substituted heteroaryl, optionally substituted heterocycloalkyl, optionally substituted heterocycle, optionally substituted arylalkyl, optionally substituted heterocycloalkylalkyl, or optionally substituted heteroarylalkyl;

$R_5$ is H, alkyl, heteroalkyl, heterocycloalkyl, alkyl or aryl carbonyl, or optionally substituted alkyl or aryl sulfonyl;

and pharmaceutically acceptable salts, solvates, stereoisomers and prodrugs thereof.

In another embodiment, this invention encompasses compounds of formula (2):

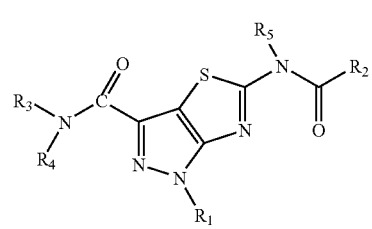

(2)

wherein:

$R_1$, $R_3$ and $R_4$ are each independently H, optionally substituted alkyl, optionally substituted alkenyl, optionally substituted alkynyl, optionally substituted aryl, optionally substituted heteroaryl, optionally substituted heterocycloalkyl, optionally substituted heterocycle, optionally substituted arylalkyl, optionally substituted heterocycloalkylalkyl, optionally substituted heteroarylalkyl, optionally substituted alkoxycarbonyl, optionally substituted aminocarbonyl, optionally substituted carbonyl, or optionally substituted sulfonyl; or $R_3$ and $R_4$, with the nitrogen to which they are attached, form an optionally substituted heterocycle;

$R_2$ is H, optionally substituted alkyl, optionally substituted alkenyl, optionally substituted alkynyl, optionally substituted aryl, optionally substituted heteroaryl, optionally substituted heterocycloalkyl, optionally substituted heterocycle, optionally substituted arylalkyl, optionally substituted heterocycloalkylalkyl, or optionally substituted heteroarylalkyl;

$R_5$ is H, alkyl, heteroalkyl, heterocycloalkyl, alkyl or aryl carbonyl, or optionally substituted alkyl or aryl sulfonyl;

and pharmaceutically acceptable salts, solvates, stereoisomers and prodrugs thereof.

In one specific embodiment, $R_3$ and $R_4$, with the nitrogen atom to which they are attached, form an optionally substituted heterocycle. An example of an optionally substituted heterocycle is an optionally substituted pyrrolidine.

In another specific embodiment, $R_5$ is H, and $R_2$ is lower alkyl.

In another specific embodiment, $R_5$ is H, and $R_2$ is cyclopropyl.

In another specific embodiment, $R_2$ and $R_5$ are both lower alkyl.

In another specific embodiment, $R_5$ is H, and $R_2$ is aryl.

In another specific embodiment, $R_5$ is H, and $R_2$ is phenyl.

In another specific embodiment, $R_1$ is branched alkyl (e.g., t-butyl).

In another specific embodiment, $R_2$ is optionally substituted aryl (e.g., optionally substituted phenyl).

In another specific embodiment, $R_1$ is t-butyl, and $R_2$ is optionally substituted phenyl.

In another embodiment, this invention encompasses compounds of formula (3):

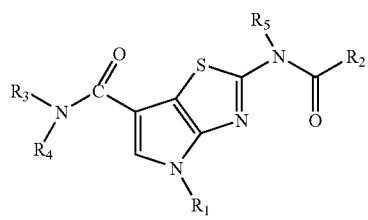

(3)

wherein:

$R_1$, $R_3$ and $R_4$ are each independently H, optionally substituted alkyl, optionally substituted alkenyl, optionally substituted alkynyl, optionally substituted aryl, optionally substituted heteroaryl, optionally substituted heterocycloalkyl, optionally substituted heterocycle, optionally substituted arylalkyl, optionally substituted heterocycloalkylalkyl, optionally substituted heteroarylalkyl, optionally substituted alkoxycarbonyl, optionally substituted aminocarbonyl, optionally substituted carbonyl, or optionally substituted sulfonyl; or $R_3$ and $R_4$, with the nitrogen to which they are attached, form an optionally substituted heterocycle;

$R_2$ is H, optionally substituted alkyl, optionally substituted alkenyl, optionally substituted alkynyl, optionally substituted aryl, optionally substituted heteroaryl, optionally substituted heterocycloalkyl, optionally substituted heterocycle, optionally substituted arylalkyl, optionally substituted heterocycloalkylalkyl, or optionally substituted heteroarylalkyl;

$R_5$ is H, alkyl, heteroalkyl, heterocycloalkyl, alkyl or aryl carbonyl, or optionally substituted alkyl or aryl sulfonyl;

and pharmaceutically acceptable salts, solvates, stereoisomers and prodrugs thereof.

In one specific embodiment, $R_1$ is branched alkyl (e.g., t-butyl).

In another embodiment, $R_2$ is optionally substituted aryl (e.g., optionally substituted phenyl).

In another embodiment, $R_1$ is t-butyl, and $R_2$ is p-methylphenyl.

In another embodiment, $R_3$ is H, and $R_4$ is optionally substituted alkyl, in particular, optionally substituted branched alkyl.

In another embodiment, $R_3$ is H, and $R_4$ is straight or branched alkyl, substituted with heteroaryl, heterocycle, or alkoxy.

Another embodiment of this invention encompasses pharmaceutical compositions comprising compounds of formula (1), (2), or (3), and pharmaceutically acceptable salts, solvates, stereoisomers or prodrugs thereof.

In another embodiment, this invention encompasses methods of treating, preventing and managing various diseases and disorders, which comprise administering to a patient (e.g., a mammal, preferably a human) in need of such treatment, prevention or management a therapeutically or prophylactically effective amount of a compound of formula (1), (2), or (3), or a pharmaceutically acceptable salt, solvate, stereoisomer or prodrug thereof.

4. DETAILED DESCRIPTION OF THE INVENTION

This invention encompasses novel thiazolopyrazole compounds, pharmaceutical compositions and dosage forms comprising them, and methods of treating, preventing and managing various diseases or disorders using them. Examples of diseases or disorders include, but are not limited to: allergic disorders (e.g., immunodeficiency diseases and hypersensitivity); cardiovascular disorders (e.g., hypertension and arteriosclerosis); dental and oral disorders (e.g., inflammation of the oral mucosa); dermatologic disorders (e.g., dermatitis and skin infections); disorders due to physical agents (e.g., altitude or motion sickness); endocrine and metabolic disorders (e.g., hypopituitarism and hyperthyroism); gastrointestinal disorders (e.g., inflammatory bowel disease and pancreatitis); gentourinary disorders (e.g., urinary incontinence and myoneurogenic disorders); gynecologic and obstetrics disorders (e.g., sexual dysfunction and gynecologic inflammations); hematological and oncologic disorders (e.g., anemias, myeloproliferative disorder and cancer); hepatic and biliary disorders (e.g., fatty liver and hepatitis); infectious diseases (e.g., diseases caused by bacterial, viral or fungal infections); musculoskeletal and connective tissue disorders (e.g., rheumatoid arthritis and systemic sclerosis); neurologic disorders (e.g., pain and sleep disorders); nutritional disorders (e.g., protein-energy malnutrition); ophthalmologic disorders (e.g., conjunctivitis and keratitis); psychiatric disorders (e.g., anxiety and mood disorders); and pulmonary disorders (e.g., asthma and bronchitis).

4.1 Definitions

Unless otherwise specified, the meanings of various terms and phrases used herein are described below.

The term "alkyl" means a saturated straight chain or branched hydrocarbon having from 1 to 20 carbon atoms, specifically, 1-10 carbon atoms, more specifically, 1-4 carbon atoms. The term "lower alkyl" refers to a hydrocarbon having from 1 to 10, specifically, 1 to 6, more specifically, 1 to 4 carbon atoms. An alkyl group is an optionally substituted straight, branched or cyclic (cycloalkyl) saturated hydrocarbon group. When substituted, alkyl groups may be substituted as described herein at any available point of attachment. An alkyl group substituted with an alkyl group may be referred to as a "branched alkyl group." Examples of unsubstituted alkyl groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, and dodecyl. Alkyl groups may also comprise one or more carbon-to-carbon double bonds or one or more carbon-to-carbon triple bonds.

The term "alkenyl" means a straight chain or branched hydrocarbon having from 2 to 20 carbon atoms, specifically 2-10 carbon atoms, more specifically 2-6 carbon atoms, and including at least one carbon-carbon double bond. Representative straight chain and branched $(C_2-C_{10})$alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, and 3-decenyl. The double bond of an alkenyl group may be unconjugated or conjugated to another unsaturated group. An alkenyl group may be unsubstituted or substituted.

The term "alkynyl" means a straight chain or branched non-cyclic hydrocarbon having from 2 to 20 carbon atoms, specifically 2-10 carbon atoms, more specifically 2-6 carbon atoms, and including at lease one carbon-carbon triple bond. Representative straight chain and branched —$(C_2-C_{10})$alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like. The triple bond of an alkynyl group may be unconjugated or conjugated to another unsaturated group. An alkynyl group may be unsubstituted or substituted.

The term "alkoxy" means an alkyl group bonded through an oxygen linkage (—O—). Examples of alkoxy include, but are not limited to, —$OCH_3$, —$OCH_2CH_3$, —$O(CH_2)_2CH_3$, —$O(CH_2)_3CH_3$, —$O(CH_2)_4CH_3$, and —$O(CH_2)_5CH_3$.

The term "aryl" refers to monocyclic and bicyclic aromatic rings, e.g., phenyl, as well as groups that are fused, e.g., napthyl or phenanthrenyl. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more substituents as defined herein. Representative aryl groups include, but are not limited to, phenyl, tolyl, anthracenyl, fluorenyl, indenyl, azulenyl, phenanthrenyl and naphthyl.

The term "arylalkyl" refers to an aromatic ring bonded to an alkyl group.

The term "cycloalkyl" means a specie of alkyl containing from 3 to 15 carbon atoms, without alternating or resonating double bonds between carbon atoms. It may contain from 1 to 4 rings. Examples of unsubstituted cycloalkyls include, but are not limited to, cyclopropyl, cyclobutyl, cyclopentyl, cyclohexyl, and adamantyl. A cycloalkyl may be substituted with one or more of the substituents as defined below.

The term "halogen" or "halo" refers to chlorine, bromine, fluorine or iodine.

The term "heteroalkyl" refers to an alkyl moiety which comprises a heteroatom such as N, O, P, B, S, Si, Sb, Al, Sn, As, Se or Ge. The heteroatom may be connected to the rest of the heteroalkyl moiety by a saturated or unsaturated bond. Thus, an alkyl substituted with a group, such as heterocycloalkyl, substituted heterocycloalkyl, heteroaryl, substituted heteroaryl, alkoxy, aryloxy, boryl, phosphino, amino, silyl, thio, or seleno, is within the scope of the term heteroalkyl. Examples of heteroalkyls include, but are not limited to, cyano, benzoyl, 2-pyridyl and 2-furyl.

The term "heteroaryl" means a carbocyclic aromatic ring containing from 5 to 14 ring atoms, of which at least one (e.g., one, two, or three) is a heteroatom (e.g., nitrogen, oxygen, or sulfur). Heteroaryl ring structures include, but are not limited to, mono-, bi-, and tricyclic compounds, as well as fused heterocyclic moieties. Examples of heteroaryls include, but are not limited to, triazolyl, tetrazolyl, oxadiazolyl, pyridyl, furyl, benzofuranyl, thiophenyl, thiazolyl, benzothiophenyl, benzoisoxazolyl, benzoisothiazolyl, quinolinyl, pyrrolyl, indolyl, oxazolyl, benzoxazolyl, imidazolyl, benzimidazolyl, thiazolyl, benzothiazolyl, isoxazolyl, pyrazolyl, isothiazolyl, pyridazinyl, pyrimidinyl, pyrazinyl, triazinyl, cinnolinyl, phthalazinyl, quinazolinyl, benzoquinazolinyl, acridinyl, pyrimidyl, oxazolyl, benzo[1,3]dioxole and 2,3-dihydro-benzo[1,4]dioxine. A group may be unsubstituted or substituted.

The term "heteroarylalkyl" means a heteroaryl group to which an alkyl group is attached.

The term "heterocycle" means a monocyclic or polycyclic ring comprising carbon and hydrogen atoms, optionally having 1 or 2 multiple bonds, and the ring atoms contain at least one heteroatom, specifically 1 to 3 heteroatoms, independently selected from nitrogen, oxygen, and sulfur. Heterocycle ring structures include, but are not limited to, mono-, bi-, and tri-cyclic compounds. Specific heterocycles are monocyclic or bicyclic. Representative heterocycles include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl and tetrahydrothiopyranyl. A heterocyclic ring may be unsubstituted or substituted.

The term "heterocycloalkyl" refers to a cycloalkyl group in which at least one of the carbon atoms in the ring is replaced by a heteroatom (e.g., O, S or N).

The term "heterocycloalkylalkyl" means a heterocycloalkyl group to which the an alkyl group is attached.

The term "substituted," when used to describe a chemical structure or moiety, refers to a derivative of that structure or moiety wherein one or more of its hydrogen atoms is replaced with a substituent such as, but not limited to: alkyl, alkenyl, alkynyl, and cycloalkyl; alkoxyalkyl; aroyl; halo; haloalkyl (e.g., trifluoromethyl); heterocycloalkyl; haloalkoxy (e.g., trifluoromethoxy); hydroxy; alkoxy; cycloalkyloxy; heterocylooxy; oxo; alkanoyl; aryl; heteroaryl (e.g., indolyl, imidazolyl, furyl, thienyl, thiazolyl, pyrrolidyl, pyridyl, and pyrimidyl); arylalkyl; alkylaryl; heteroaryl; heteroarylalkyl; alkylheteroaryl; heterocyclo; heterocycloalkyl-alkyl; aryloxy, alkanoyloxy; amino; alkylamino; arylamino; arylalkylamino; cycloalkylamino; heterocycloamino; mono- and di-substituted amino; alkanoylamino; aroylamino; aralkanoylamino; aminoalkyl; carbamyl (e.g., $CONH_2$); substituted carbamyl (e.g., CONH-alkyl, CONH-aryl, CONH-arylalkyl or instances where there are two substituents on the nitrogen); carbonyl; alkoxycarbonyl; carboxy; cyano; ester; ether; guanidino; nitro; sulfonyl; alkylsulfonyl; arylsulfonyl; arylalkylsulfonyl; sulfonamido (e.g., $SO_2NH_2$); substituted sulfonamido; thiol; alkylthio; arylthio; arylalkylthio; cycloalkylthio; heterocyclothio; alkylthiono; arylthiono; and arylalkylthiono. In some embodiments, a substituent itself may be substituted with one or more chemical moieties such as, but not limited to, those described herein.

The term "pharmaceutically acceptable salts" refers to salts prepared from pharmaceutically acceptable non-toxic acids or bases including inorganic acids and bases and organic acids and bases. Suitable pharmaceutically acceptable base addition salts include, but are not limited to, metallic salts made from aluminum, calcium, lithium, magnesium, potassium, sodium and zinc and organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences* (18th ed., Mack Publishing, Easton Pa.: 1990) and *Remington: The Science and Practice of Pharmacy* (19th ed., Mack Publishing, Easton Pa.: 1995).

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh).

As used herein, and unless otherwise indicated, the terms "biohydrolyzable amide," "biohydrolyzable ester," "biohydrolyzable carbamate," "biohydrolyzable carbonate," "biohydrolyzable ureido," "biohydrolyzable phosphate" mean an amide, ester, carbamate, carbonate, ureido, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, alkoxyacyloxy esters, alkyl acylamino alkyl esters, and choline esters. Examples of biohydrolyzable amides include, but are not limited to, lower alkyl amides, $\alpha$-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

As used herein, and unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein, and unless otherwise indicated, the term "stereoisomeric mixture" encompasses racemic mixtures as well as stereomerically enriched mixtures (e.g., R/S=30/70; 35/65, 40/60, 45/55, 55/45, 60/40, 65/35 and 70/30).

The terms "treat," "treating" and "treatment," as used herein, contemplate an action that occurs while a patient is suffering from the specified disease or disorder, which reduces the severity of the disease or disorder, or retards or slows the progression of the disease or disorder.

As used herein, unless otherwise indicated, the terms "prevent," "preventing" and "prevention" contemplate an action that occurs before a patient begins to suffer from the specified disease or disorder, which inhibits or reduces the severity of the disease or disorder.

As used herein, and unless otherwise indicated, the terms "manage," "managing" and "management" encompass preventing the recurrence of the specified disease or disorder in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

As used herein, and unless otherwise specified, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound means an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

As used herein, and unless otherwise specified, a "prophylactically effective amount" of a compound is an amount sufficient to prevent a disease or condition, or one or more symptoms associated with the disease or condition, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

It should be noted that if there is a discrepancy between a depicted structure and a name given that structure, the structure should be accorded more weight. In addition, if the stereochemistry of a structure or a portion of a structure is not indicated with, for example, bold or dashed lines, the structure or the portion of the structure is to be interpreted as encompassing all stereoisomers of it.

4.2 Compounds of the Invention

This invention encompasses compounds of formula (1):

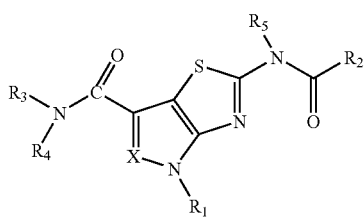

(1)

wherein:

X is CH or N;

$R_1$, $R_3$ and $R_4$ are each independently H, optionally substituted alkyl, optionally substituted alkenyl, optionally substituted alkynyl, optionally substituted aryl, optionally substituted heteroaryl, optionally substituted heterocycloalkyl, optionally substituted heterocycle, optionally substituted arylalkyl, optionally substituted heterocycloalkylalkyl, optionally substituted heteroarylalkyl, optionally substituted alkoxycarbonyl, optionally substituted aminocarbonyl, optionally substituted carbonyl, or optionally substituted sulfonyl; or $R_3$ and $R_4$, with the nitrogen to which they are attached, form an optionally substituted heterocycle;

$R_2$ is H, optionally substituted alkyl, optionally substituted alkenyl, optionally substituted alkynyl, optionally substituted aryl, optionally substituted heteroaryl, optionally substituted heterocycloalkyl, optionally substituted heterocycle, optionally substituted arylalkyl, optionally substituted heterocycloalkylalkyl, or optionally substituted heteroarylalkyl;

$R_5$ is H, alkyl, heteroalkyl, heterocycloalkyl, alkyl or aryl carbonyl, or optionally substituted alkyl or aryl sulfonyl;

and pharmaceutically acceptable salts, solvates, stereoisomers and prodrugs thereof.

In another embodiment, this invention encompasses compounds of formula (2):

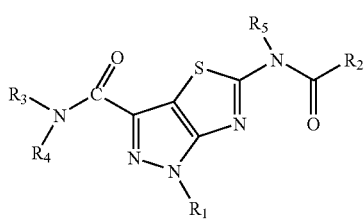

(2)

wherein:

$R_1$, $R_3$ and $R_4$ are each independently H, optionally substituted alkyl, optionally substituted alkenyl, optionally substituted alkynyl, optionally substituted aryl, optionally substituted heteroaryl, optionally substituted heterocycloalkyl, optionally substituted heterocycle, optionally substituted arylalkyl, optionally substituted heterocycloalkylalkyl, optionally substituted heteroarylalkyl, optionally substituted alkoxycarbonyl, optionally substituted aminocarbonyl, optionally substituted carbonyl, or optionally substituted sulfonyl; or $R_3$ and $R_4$, with the nitrogen to which they are attached, form an optionally substituted heterocycle;

$R_2$ is H, optionally substituted alkyl, optionally substituted alkenyl, optionally substituted alkynyl, optionally substituted aryl, optionally substituted heteroaryl, optionally substituted heterocycloalkyl, optionally substituted heterocycle, optionally substituted arylalkyl, optionally substituted heterocycloalkylalkyl, or optionally substituted heteroarylalkyl;

$R_5$ is H, alkyl, heteroalkyl, heterocycloalkyl, alkyl or aryl carbonyl, or optionally substituted alkyl or aryl sulfonyl;

and pharmaceutically acceptable salts, solvates, stereoisomers and prodrugs thereof.

In one specific embodiment, $R_3$ and $R_4$, with the nitrogen atom to which they are attached, form an optionally substituted heterocycle. An example of an optionally substituted heterocycle is an optionally substituted pyrrolidine.

In another specific embodiment, $R_5$ is H, and $R_2$ is lower alkyl.

In another specific embodiment, $R_5$ is H, and $R_2$ is cyclopropyl.

In another specific embodiment, $R_2$ and $R_5$ are both lower alkyl.

In another specific embodiment, $R_5$ is H, and $R_2$ is aryl.

In another specific embodiment, $R_5$ is H, and $R_2$ is phenyl.

In another specific embodiment, $R_1$ is branched alkyl (e.g., t-butyl).

In another specific embodiment, $R_2$ is optionally substituted aryl (e.g., optionally substituted phenyl).

In another specific embodiment, $R_1$ is t-butyl, and $R_2$ is optionally substituted phenyl.

Specific compounds of the invention include those listed in Table 1, and pharmaceutically acceptable salts, solvates, stereoisomers, racemic mixtures, stereomerically enriched mixtures, and prodrugs thereof:

TABLE 1

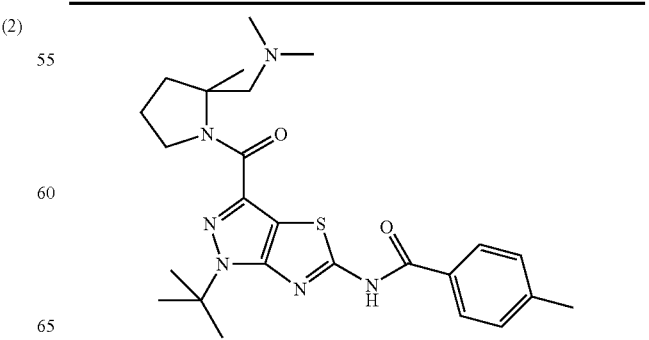

TABLE 1-continued
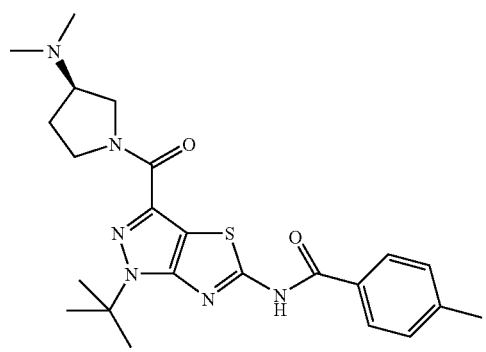
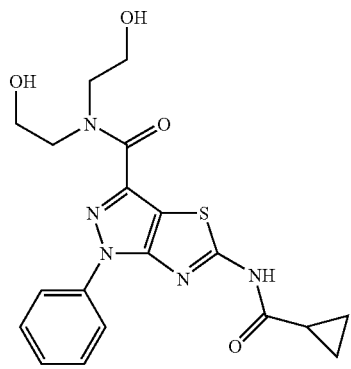
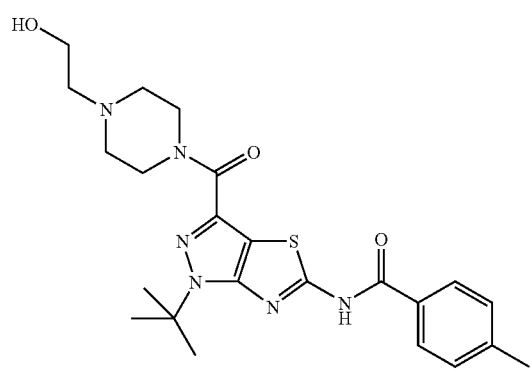
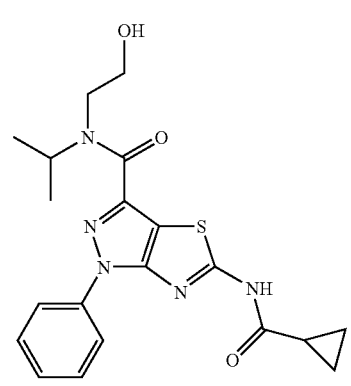
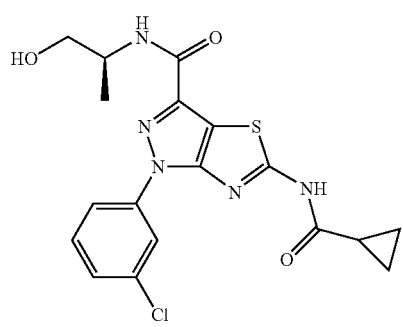
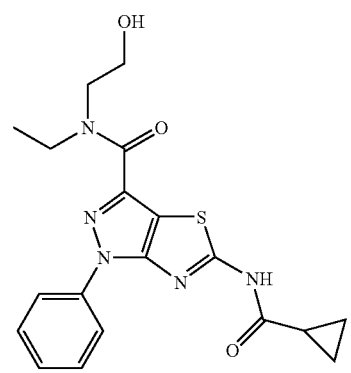
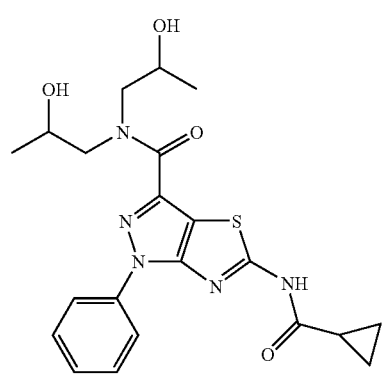
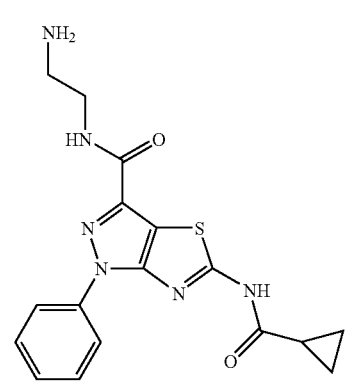

TABLE 1-continued
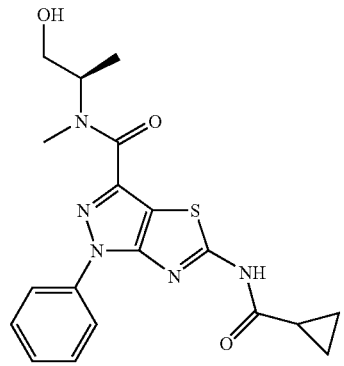
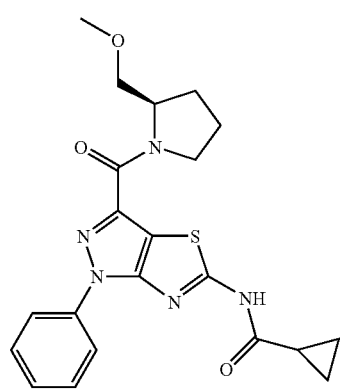
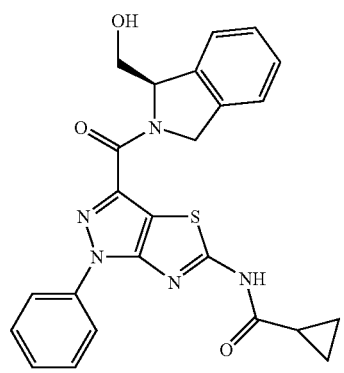
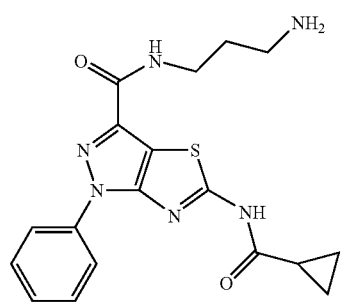
TABLE 1-continued
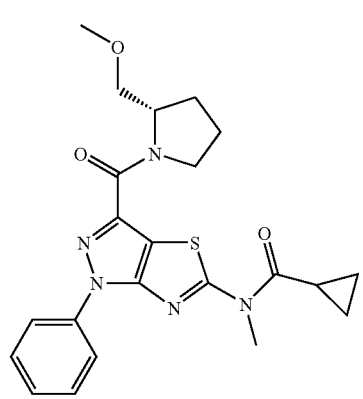
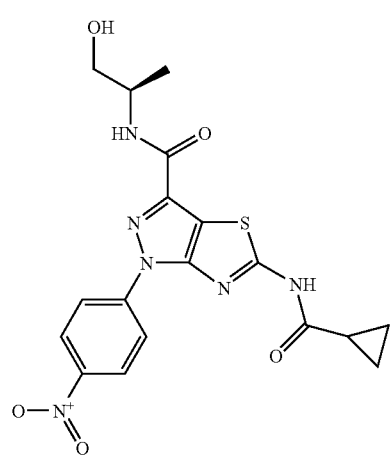
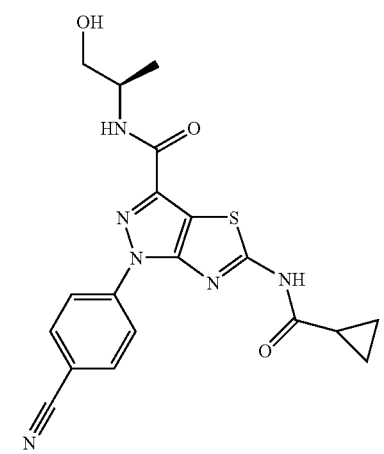

TABLE 1-continued
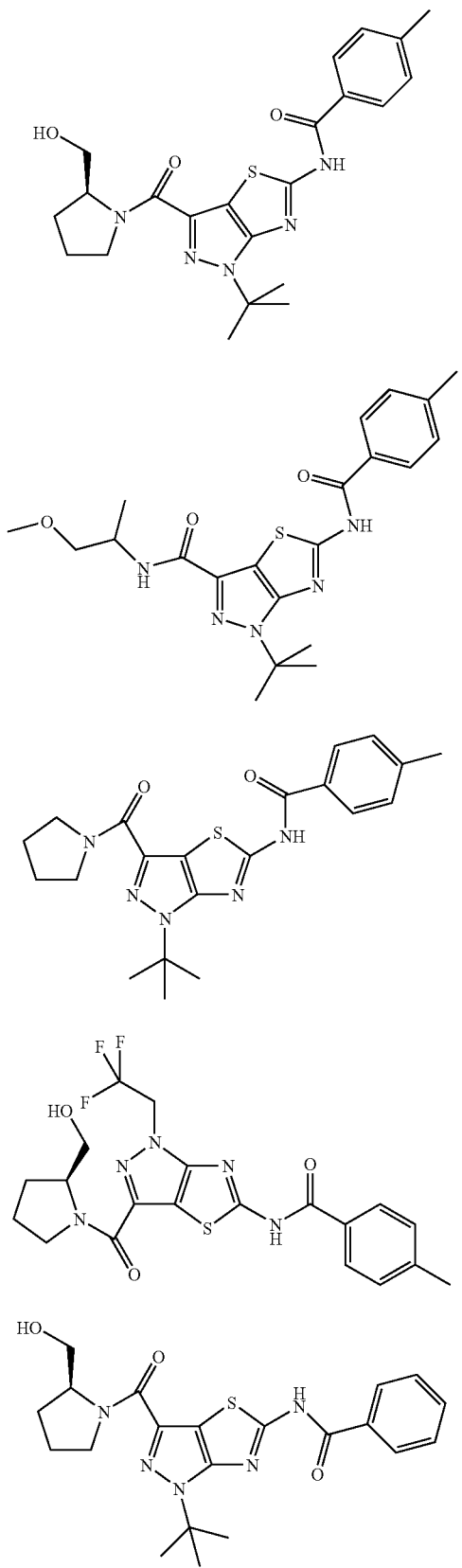
TABLE 1-continued
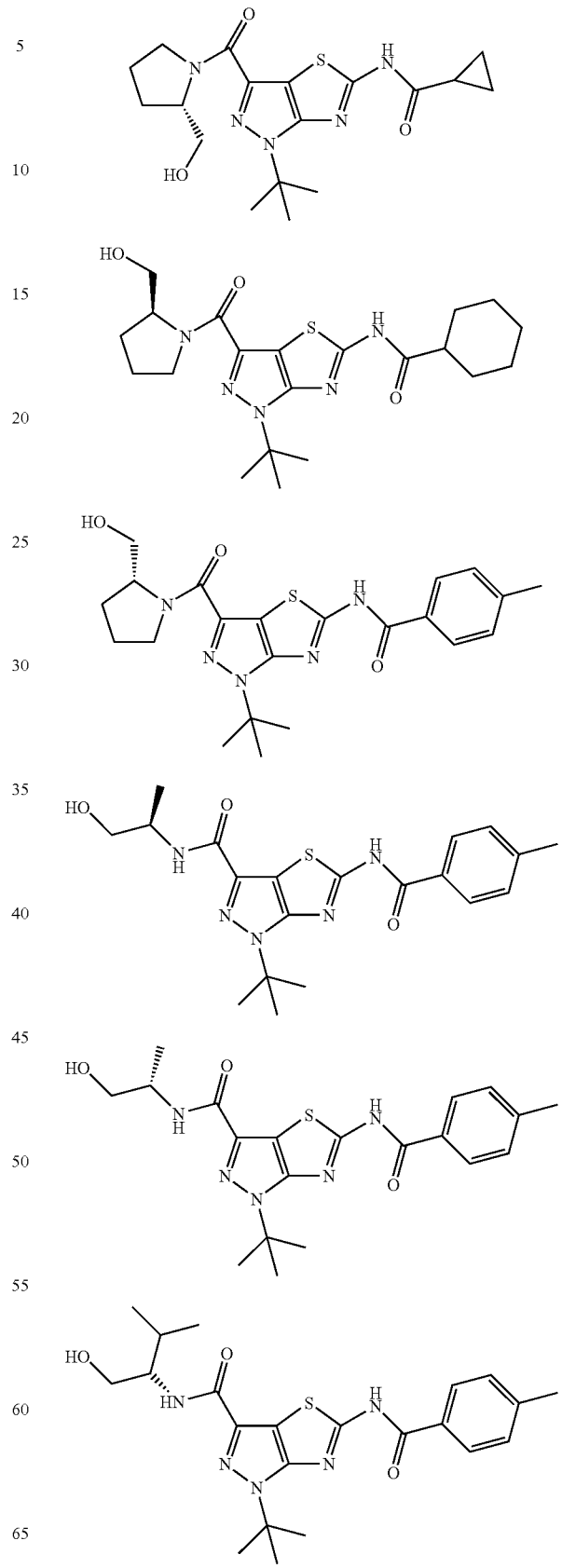

TABLE 1-continued
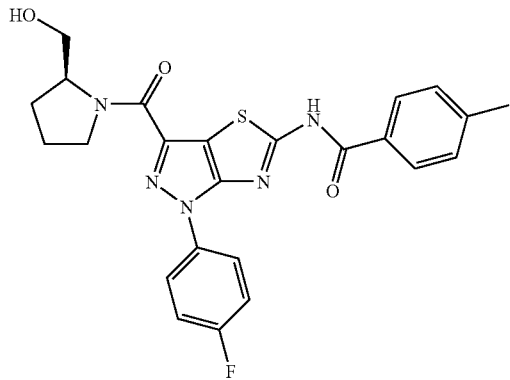
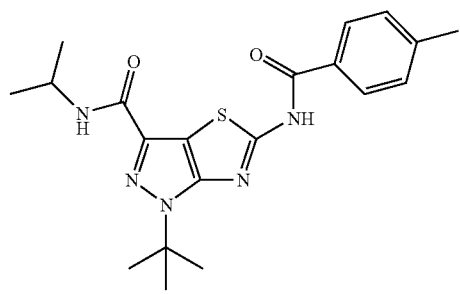
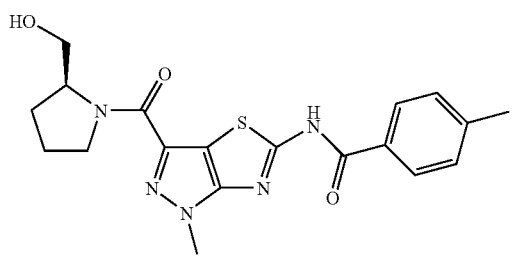
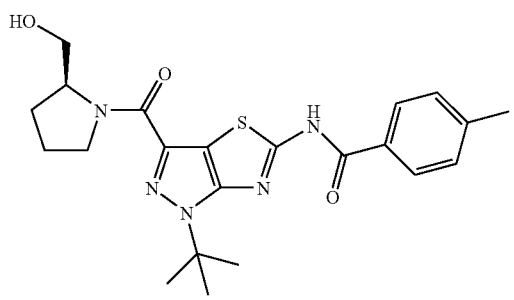
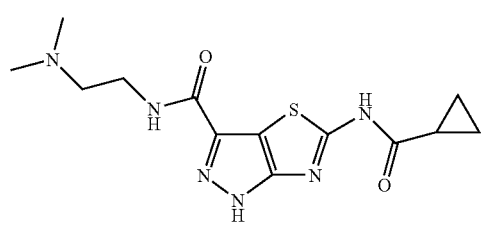
TABLE 1-continued
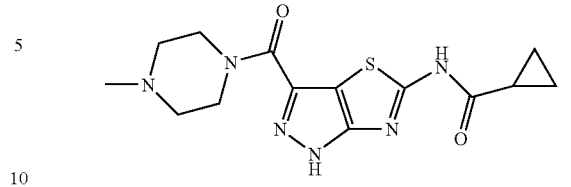
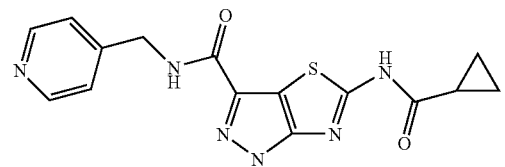
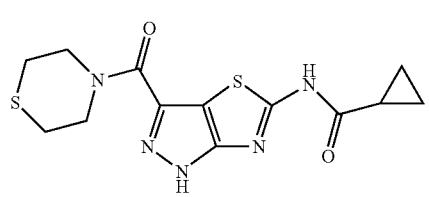
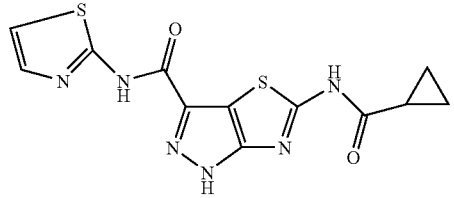
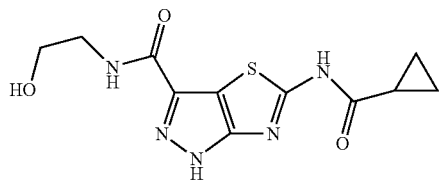
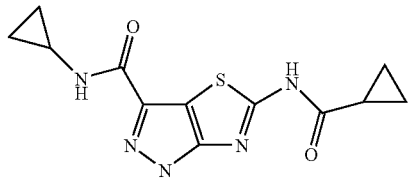
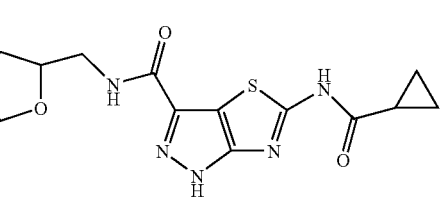
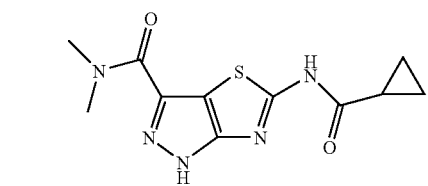

TABLE 1-continued
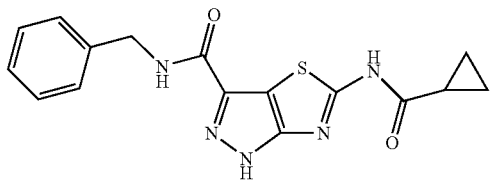
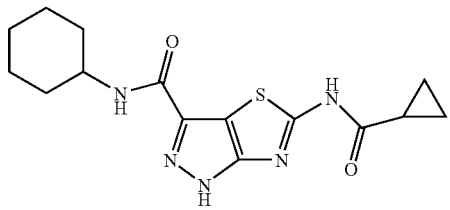
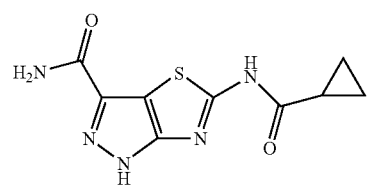
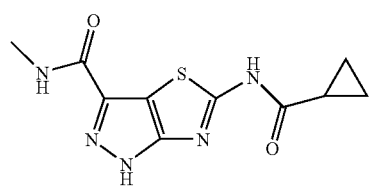
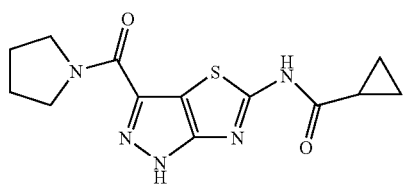
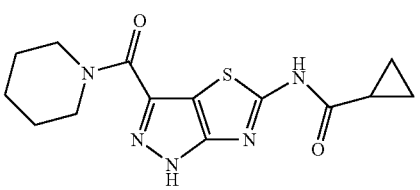
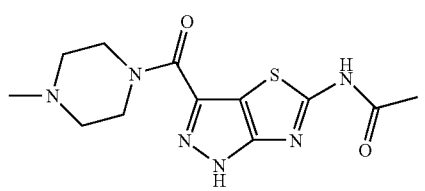
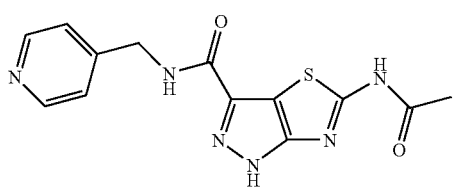
TABLE 1-continued
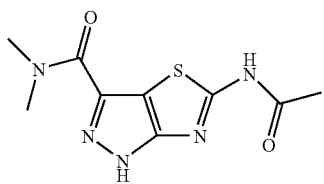
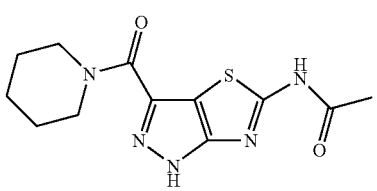
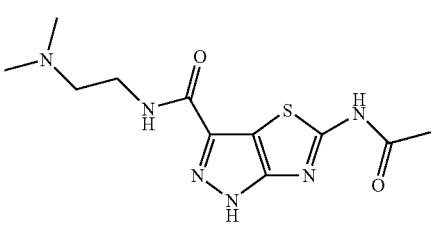
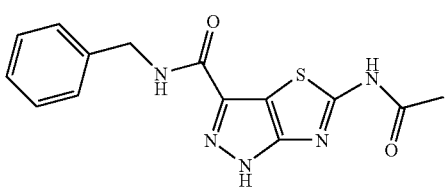
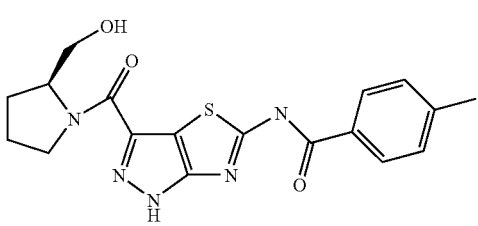
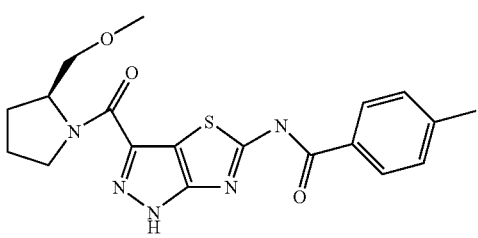
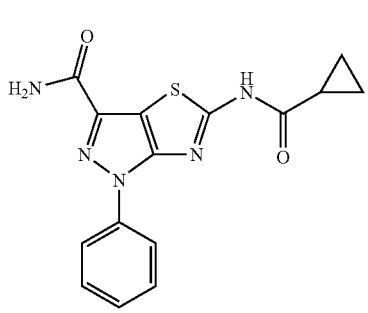

TABLE 1-continued
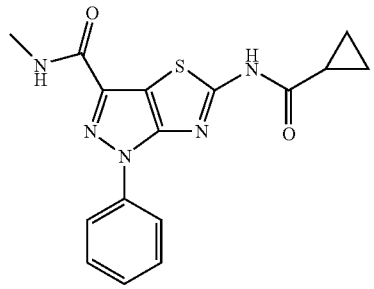
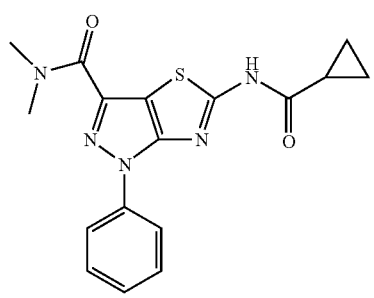
TABLE 1-continued
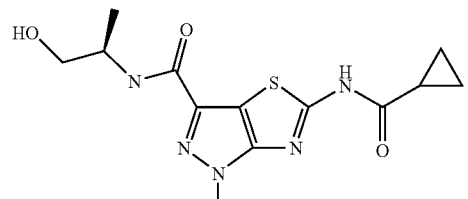
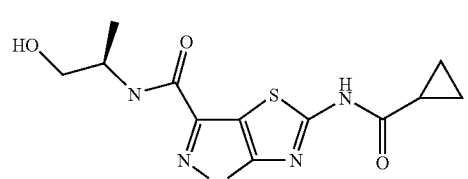
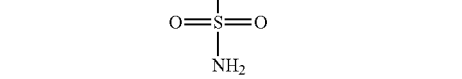
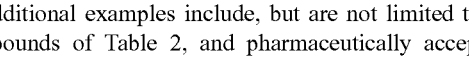
Additional examples include, but are not limited to, the compounds of Table 2, and pharmaceutically acceptable salts, solvate, stereoisomers, racemic mixtures, stereomerically enriched mixtures, and prodrugs thereof:
TABLE 2
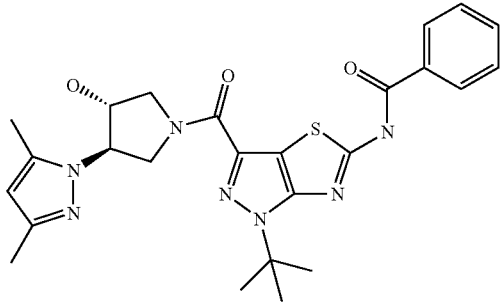

TABLE 2-continued
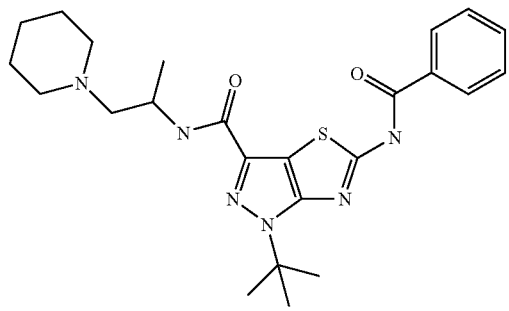
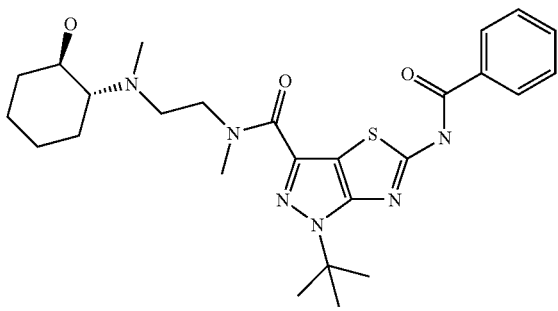
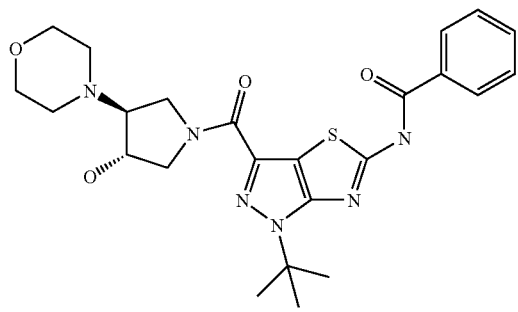
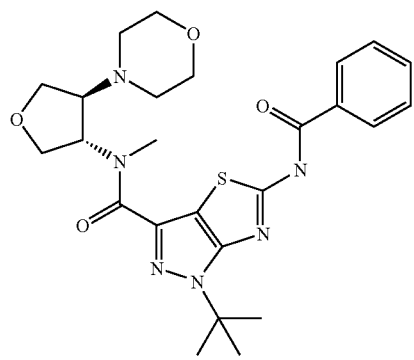
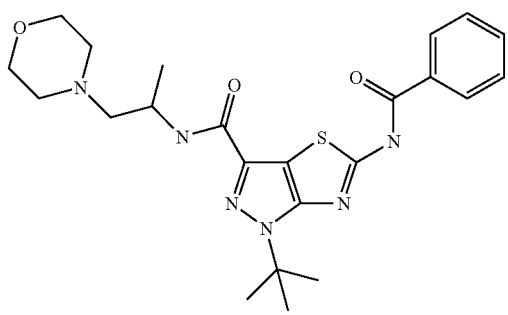

TABLE 2-continued
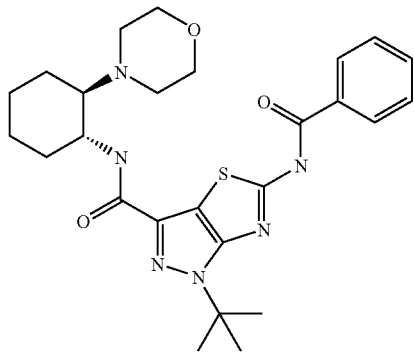
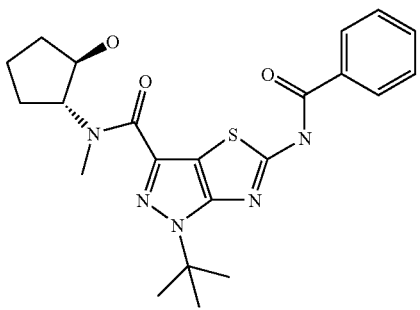
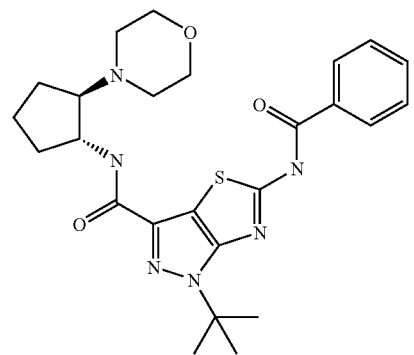
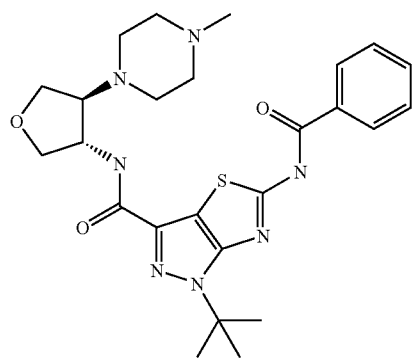

TABLE 2-continued
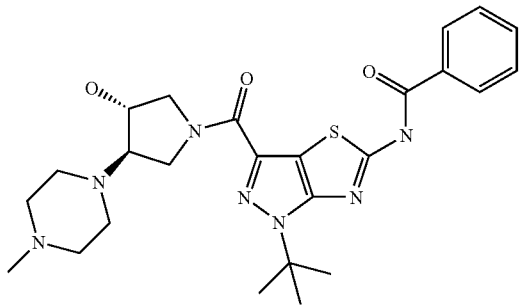
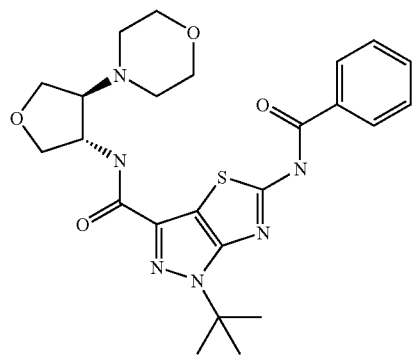
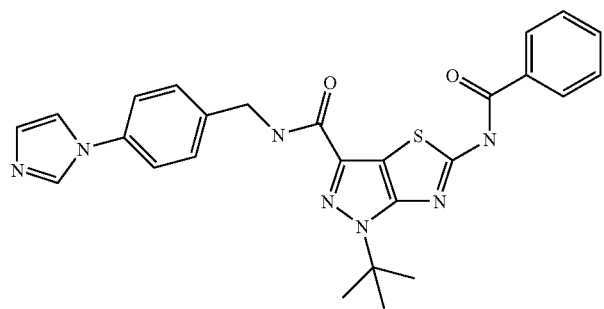
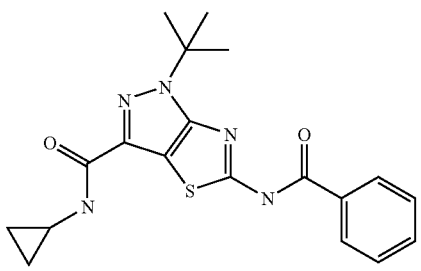
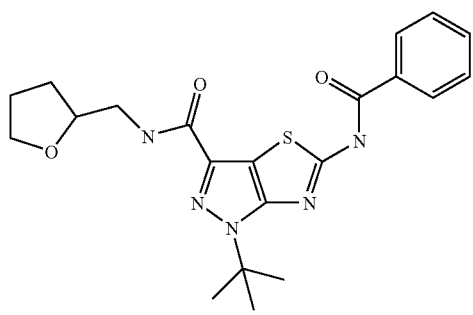

TABLE 2-continued
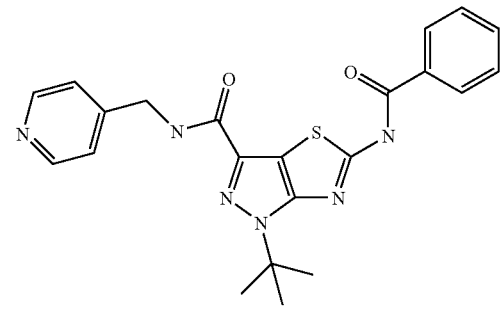
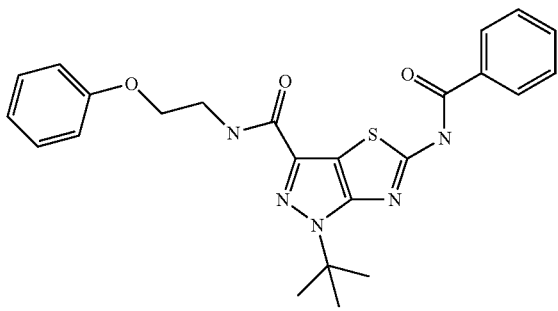
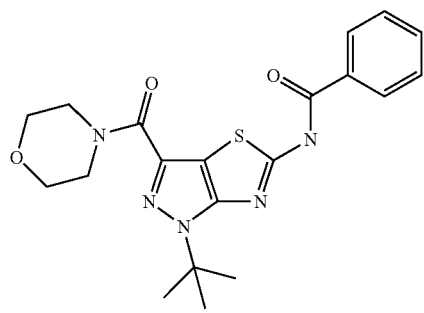
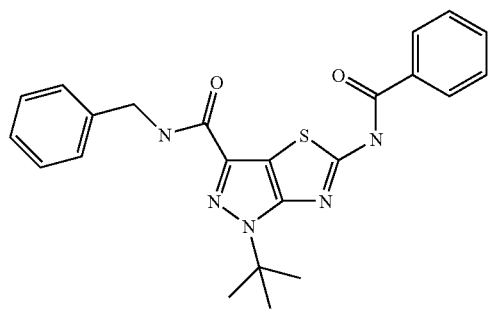
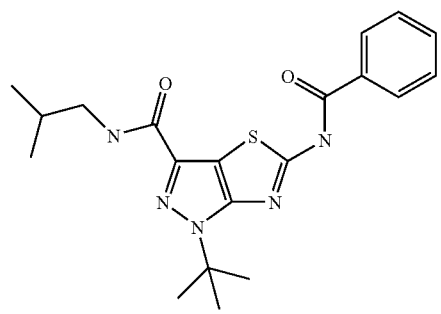

TABLE 2-continued
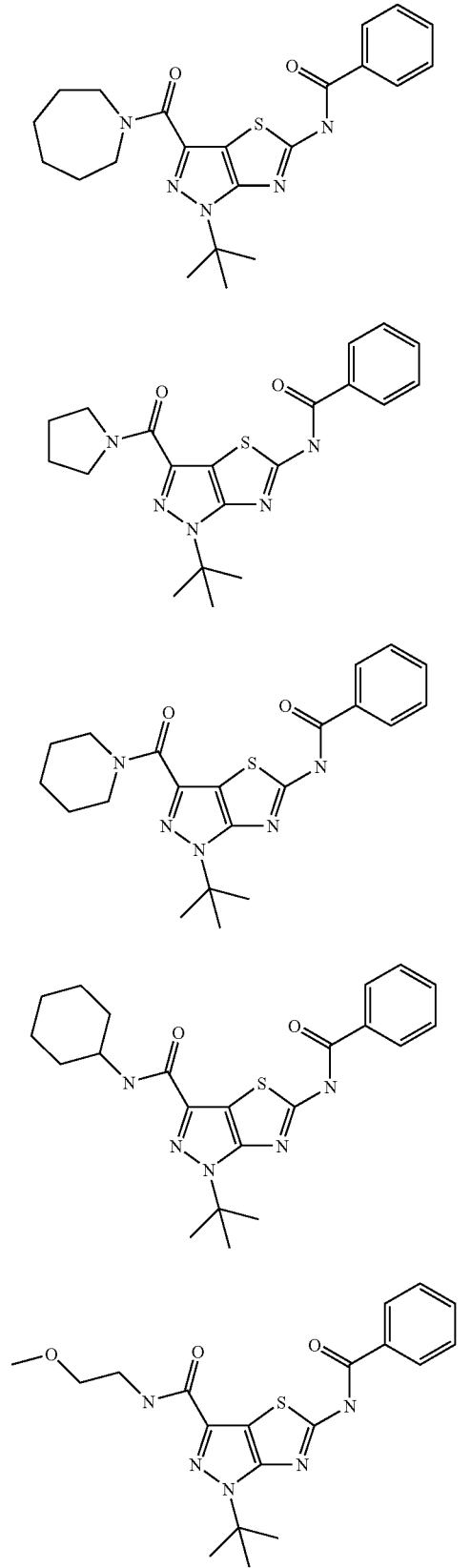

TABLE 2-continued
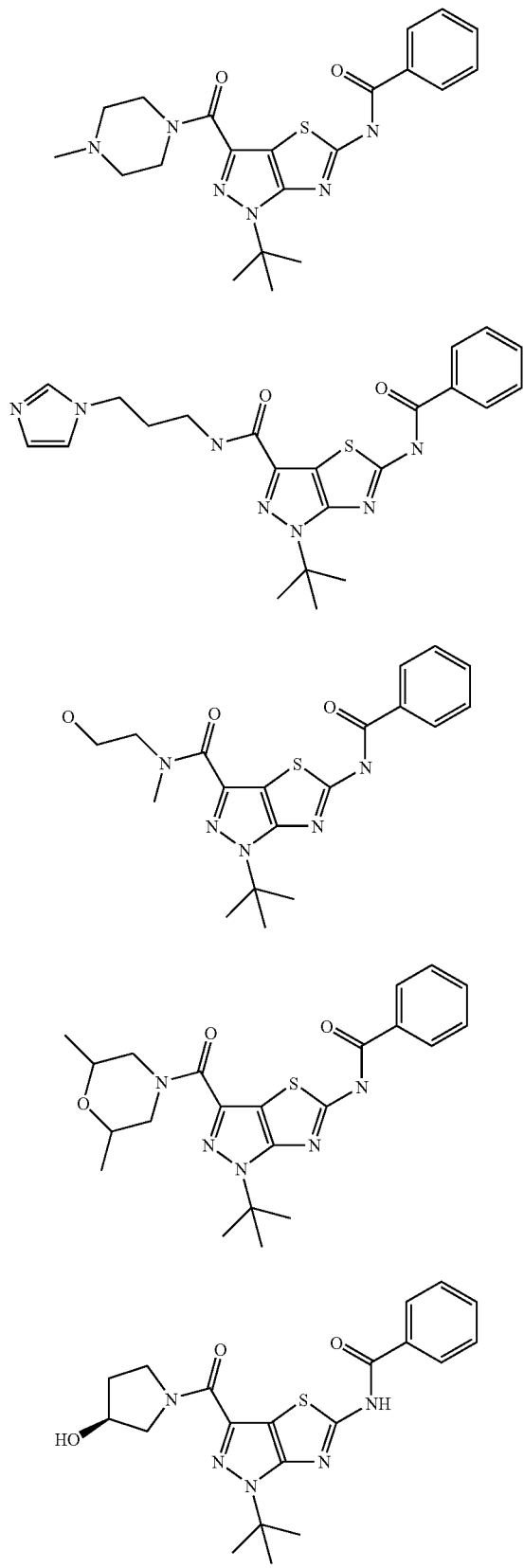

TABLE 2-continued
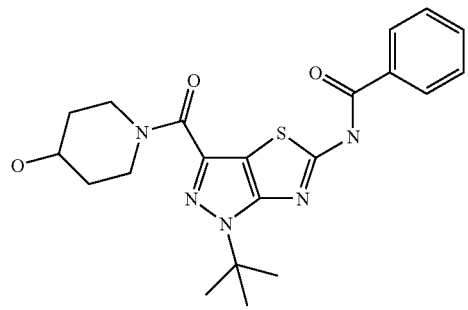
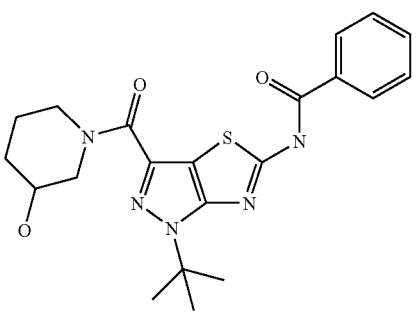
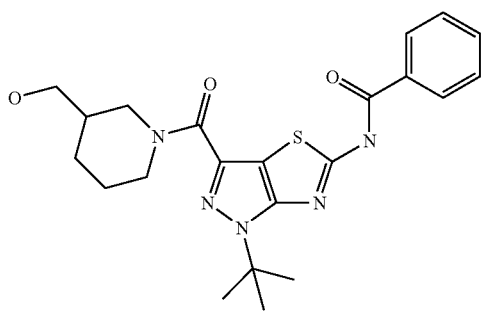
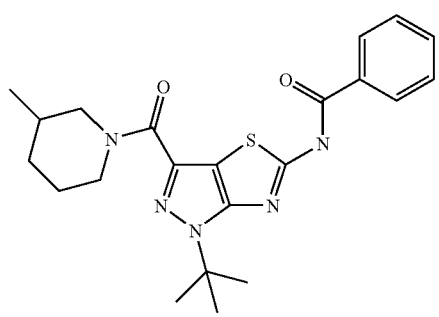
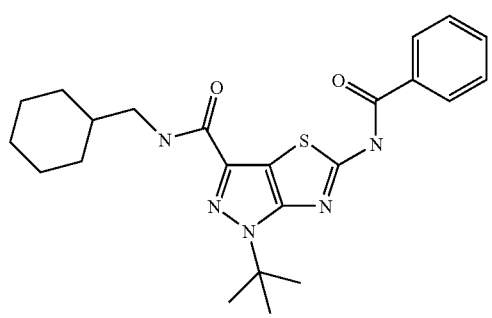

TABLE 2-continued
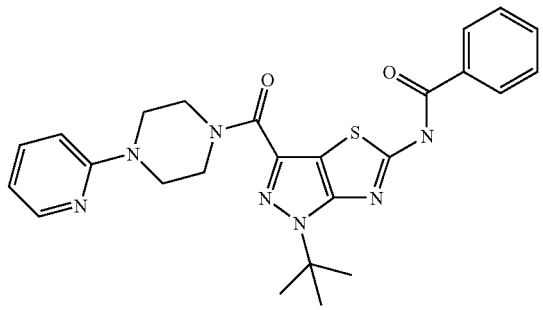
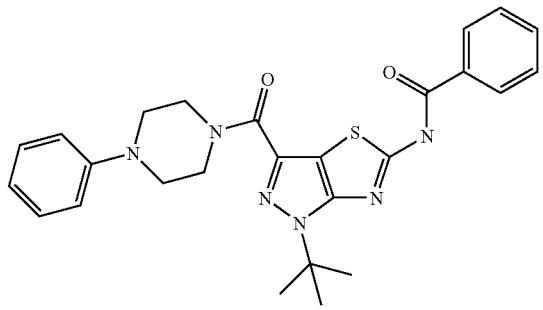
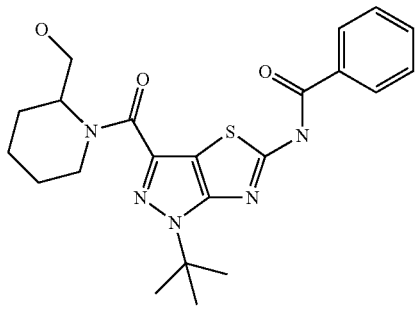
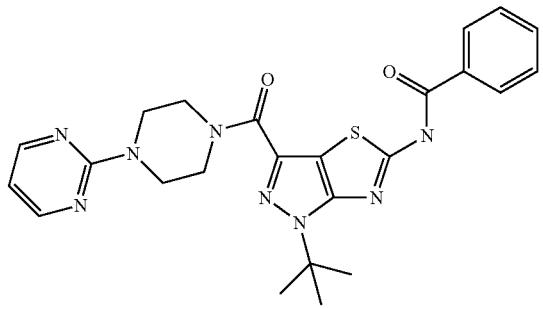
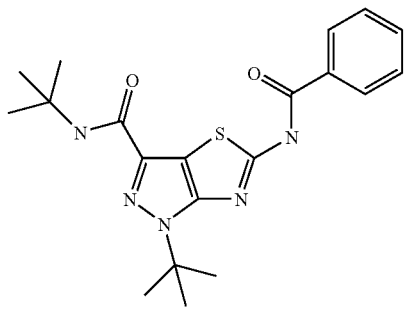

TABLE 2-continued
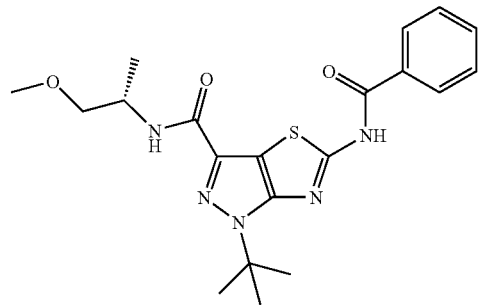
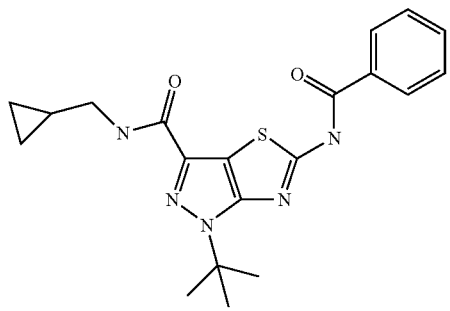
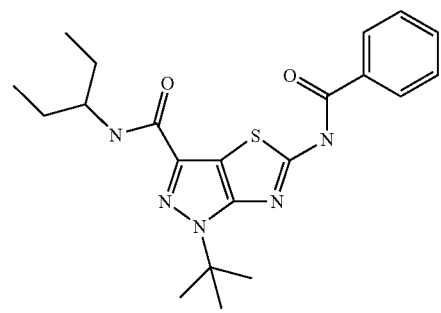
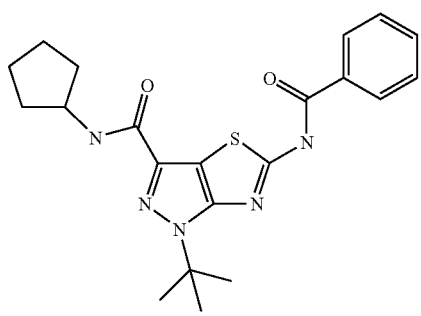
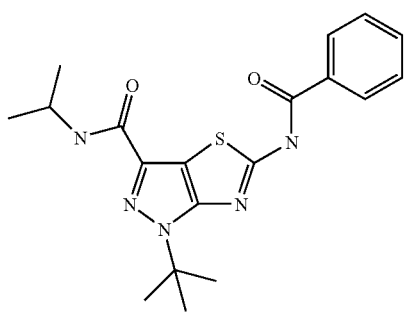

TABLE 2-continued
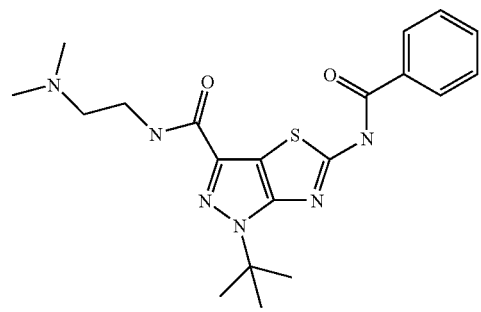
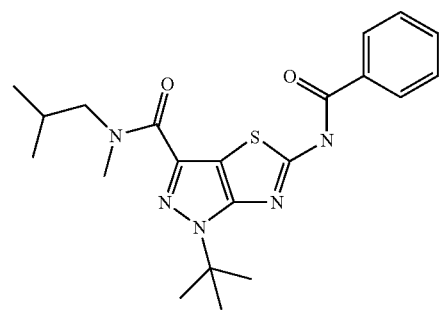
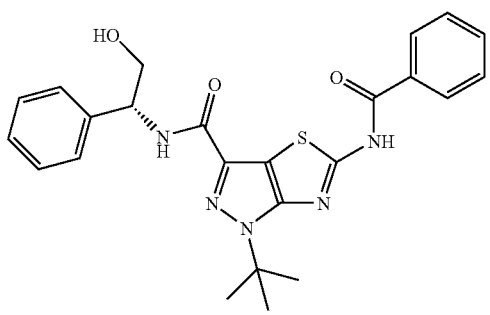
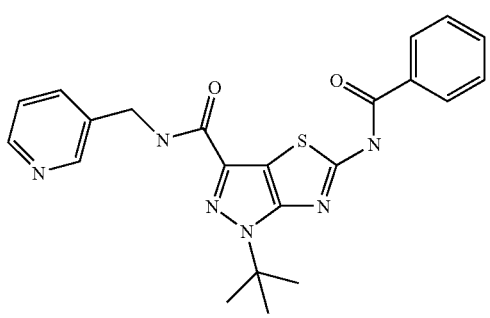
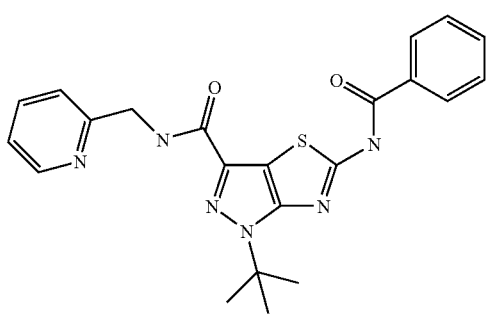

TABLE 2-continued
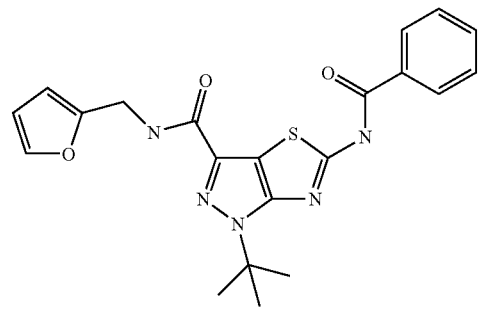
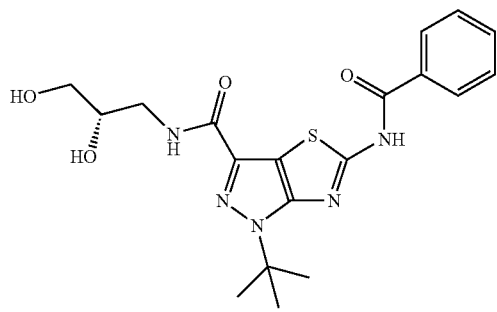
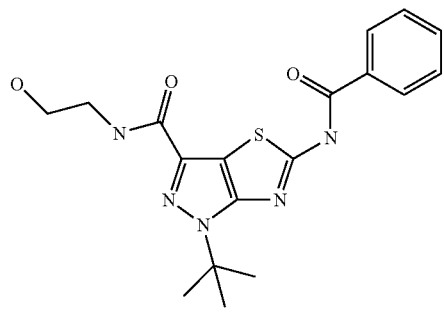
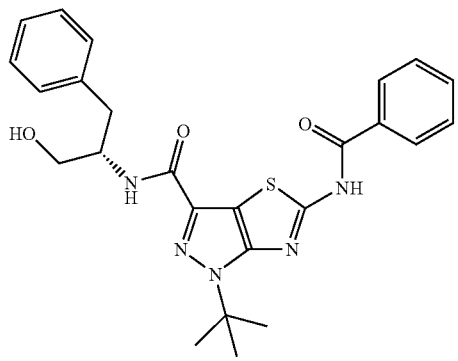
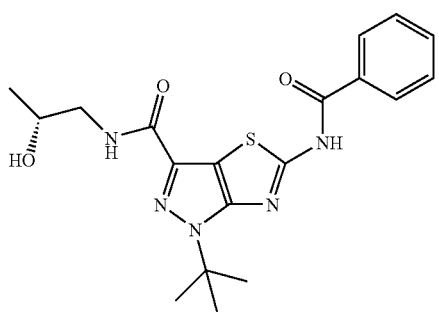

TABLE 2-continued
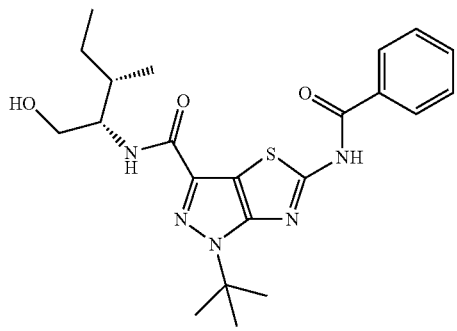
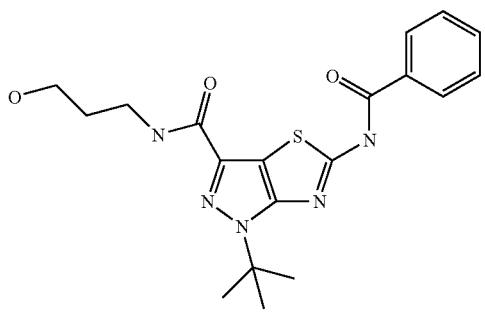
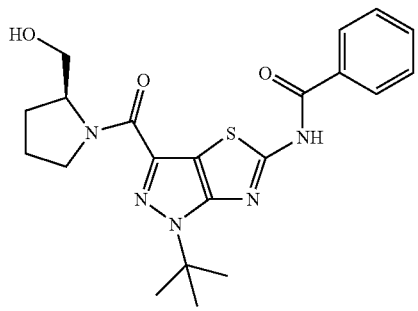
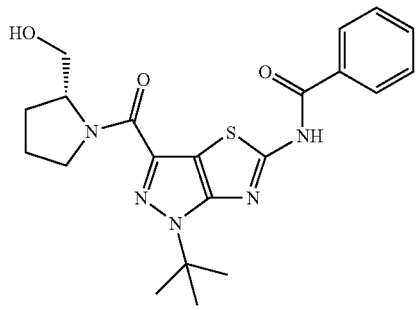
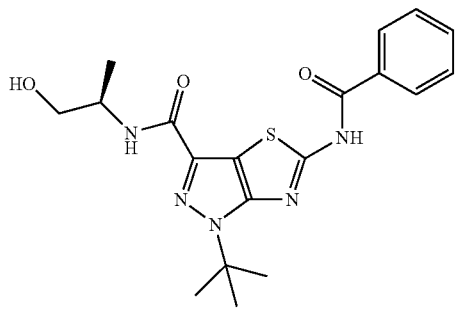

TABLE 2-continued
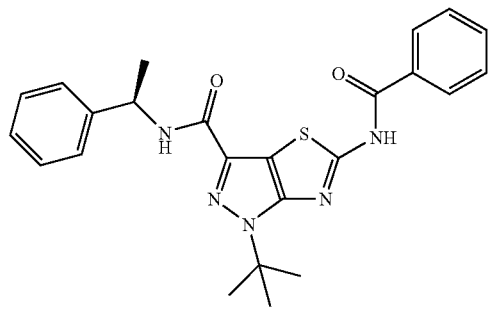
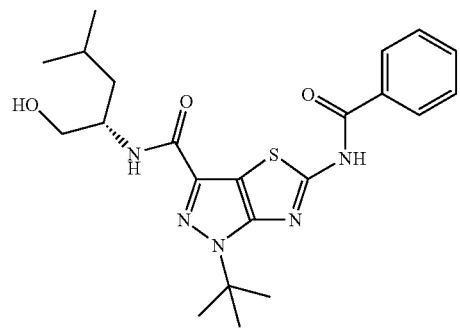
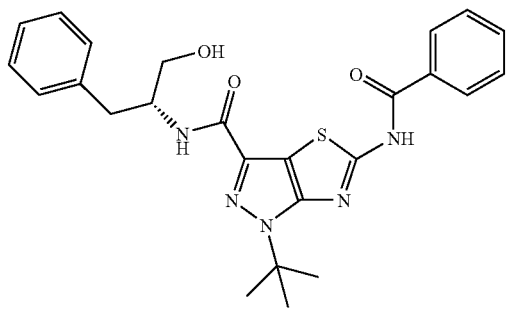
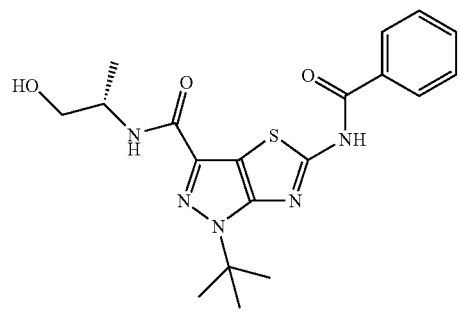
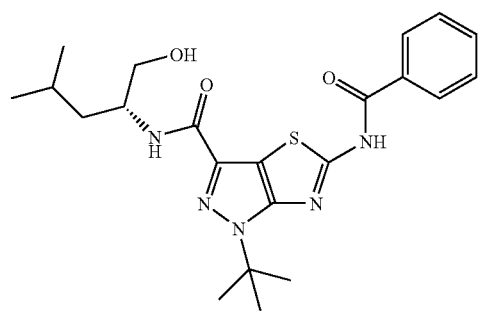

TABLE 2-continued
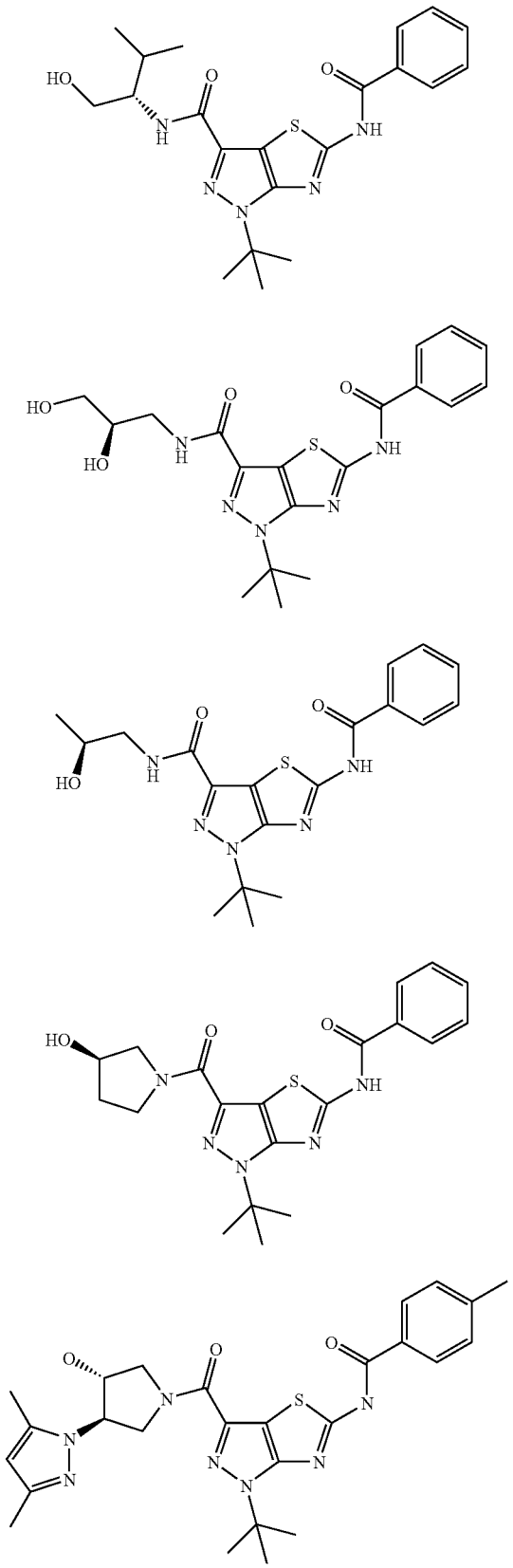

TABLE 2-continued
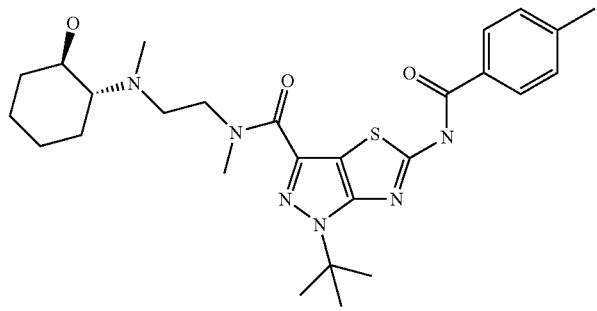
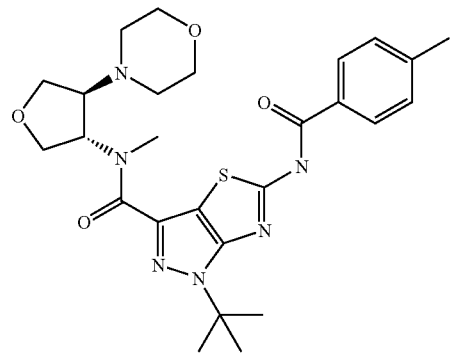
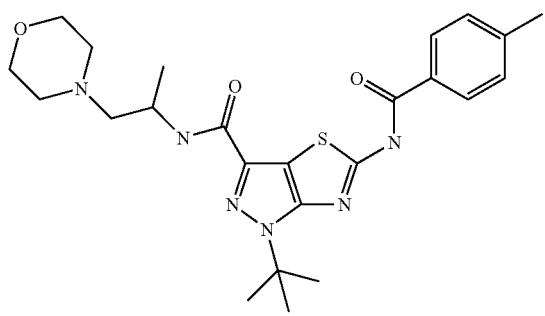
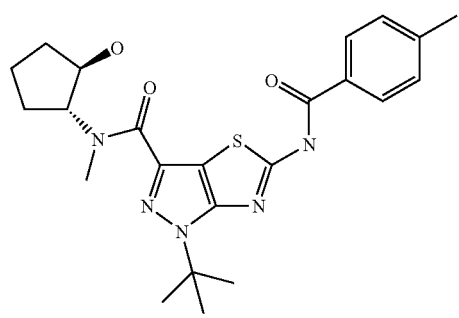
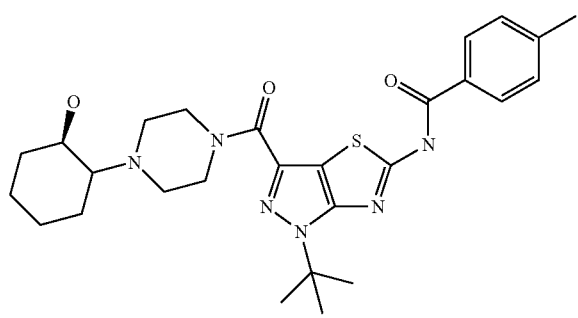

TABLE 2-continued
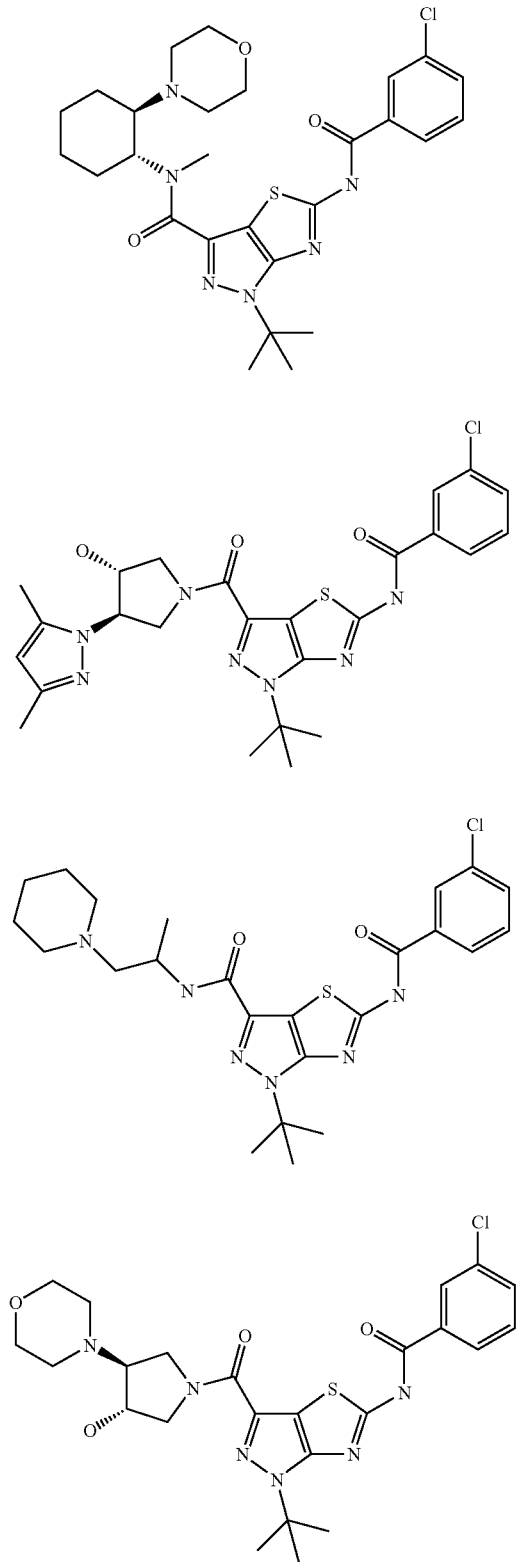

TABLE 2-continued
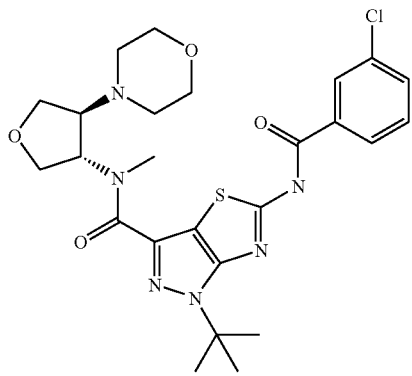
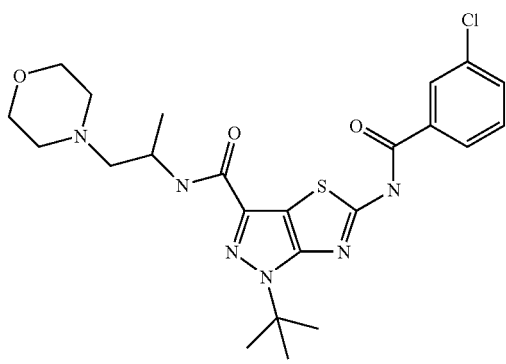
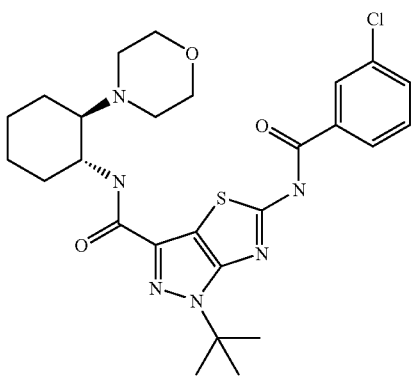
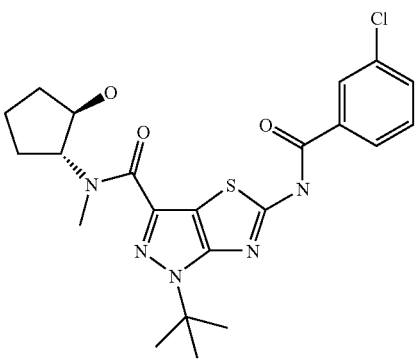

TABLE 2-continued
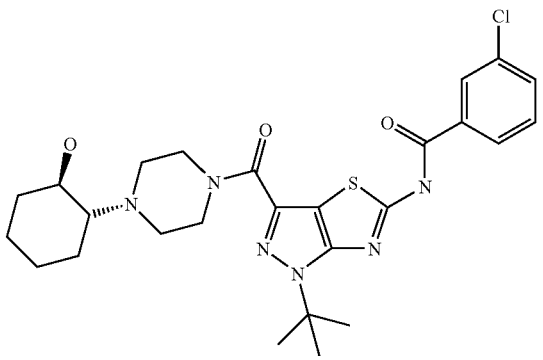
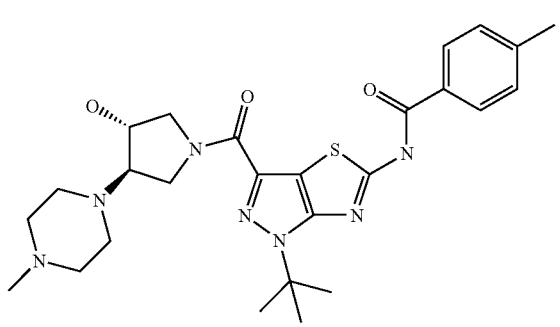
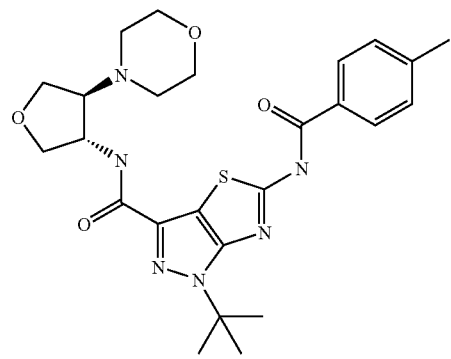
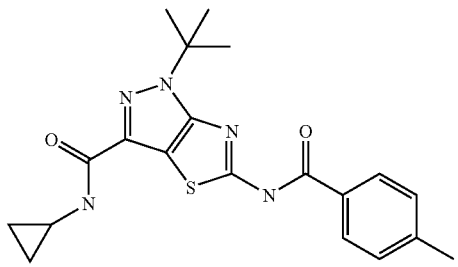
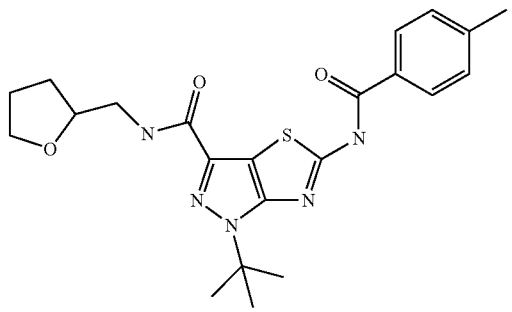

TABLE 2-continued
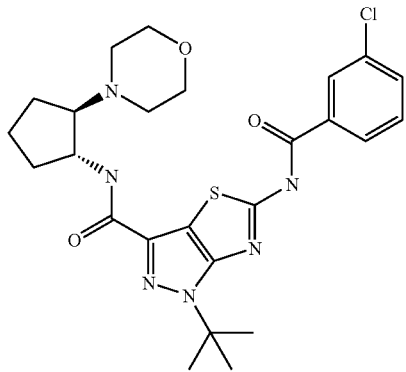
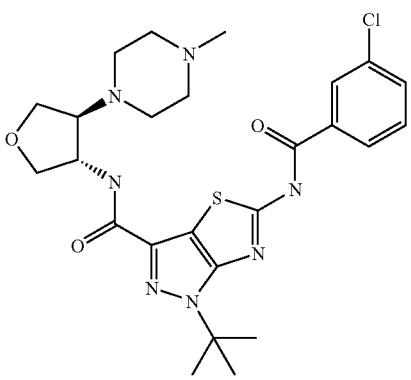
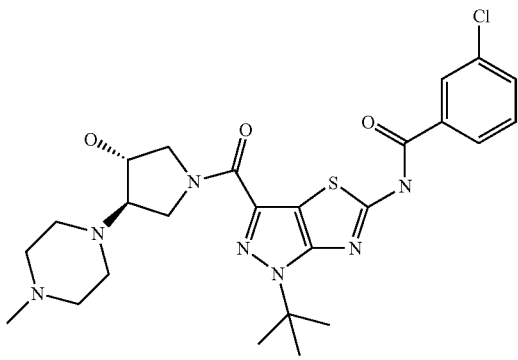
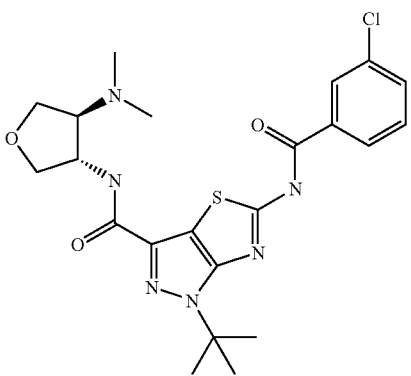

TABLE 2-continued
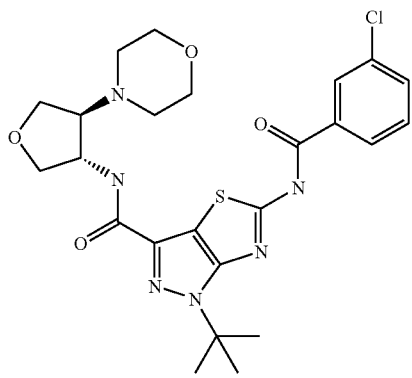
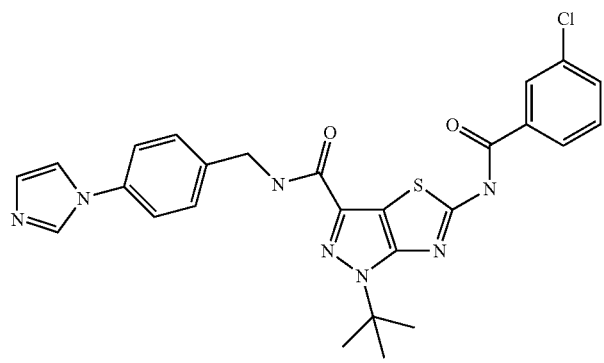
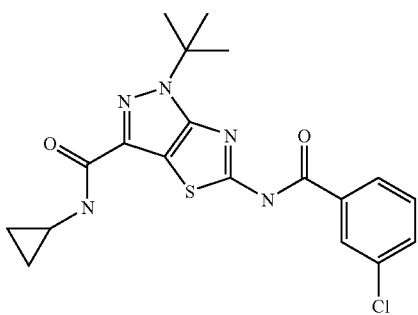
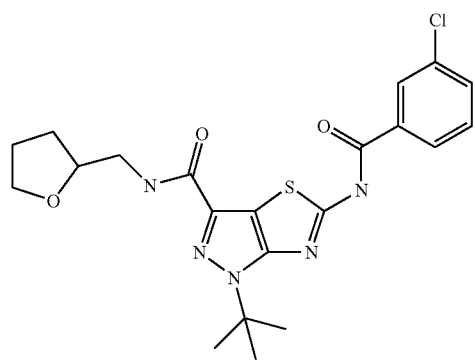

TABLE 2-continued
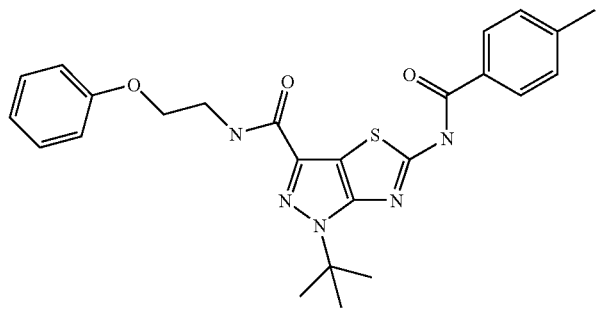
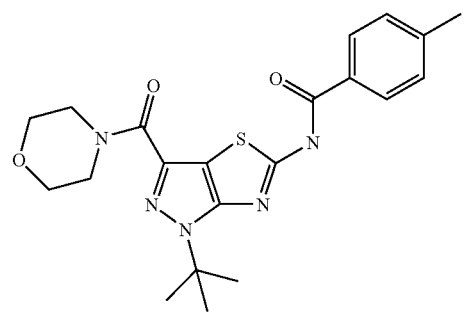
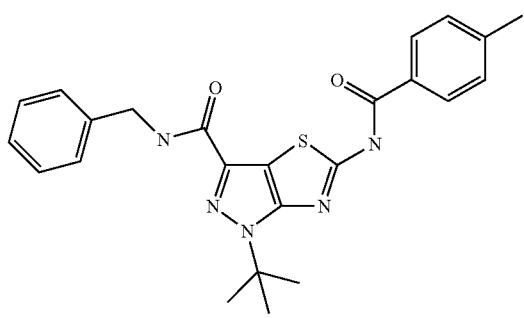
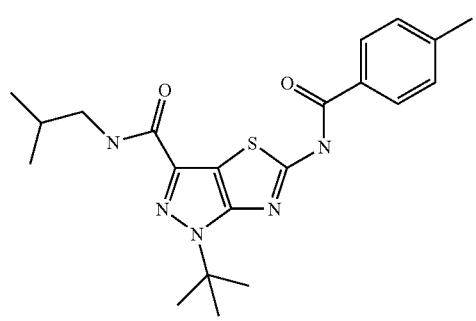
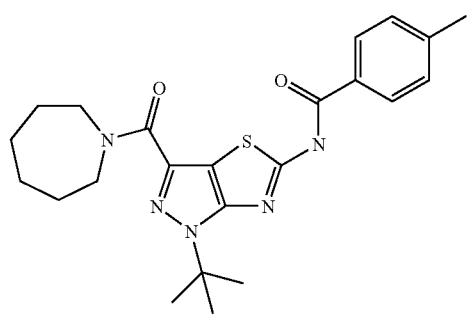

TABLE 2-continued
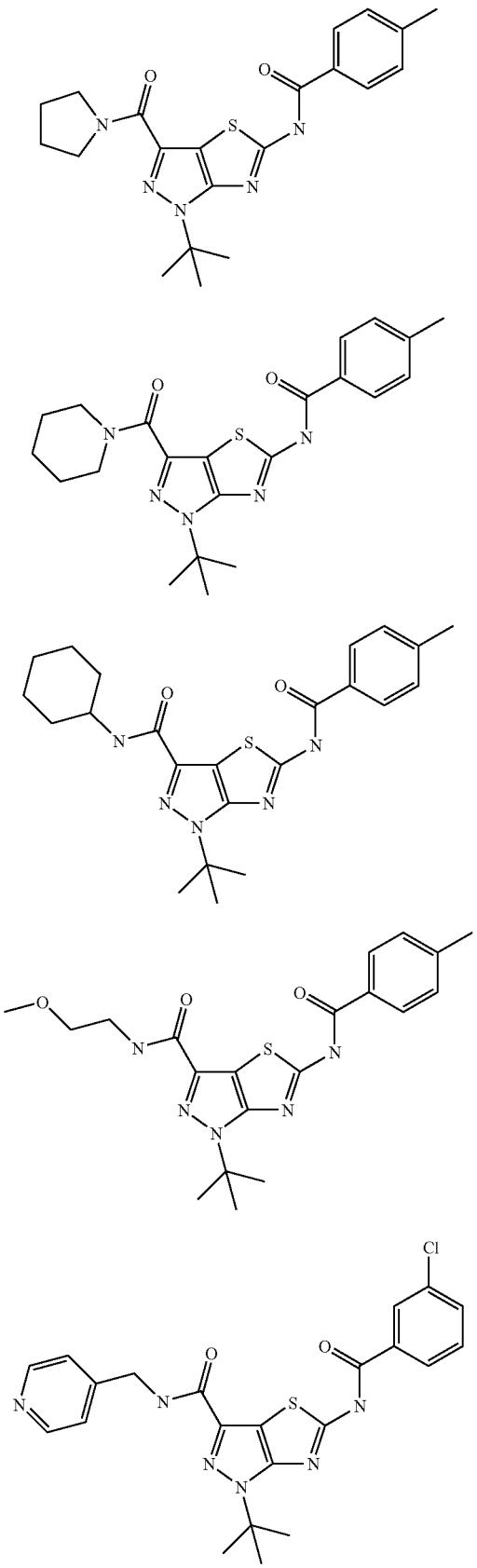

TABLE 2-continued
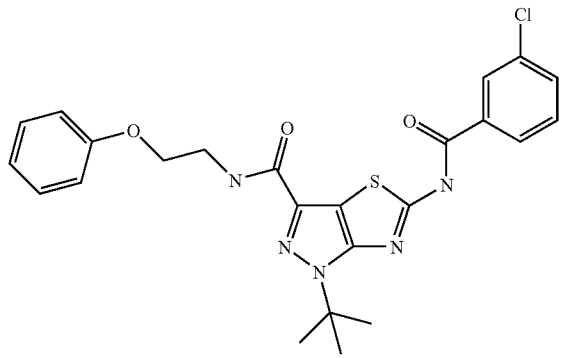
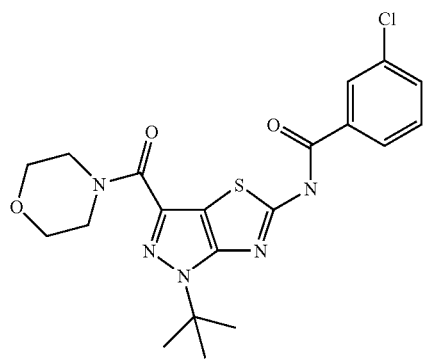
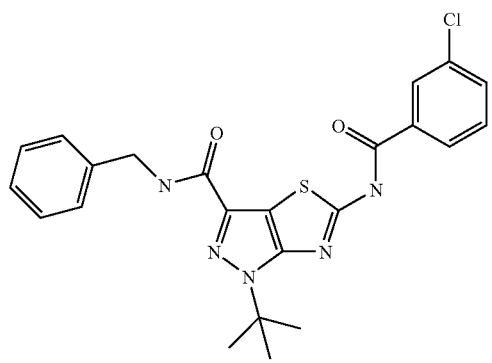
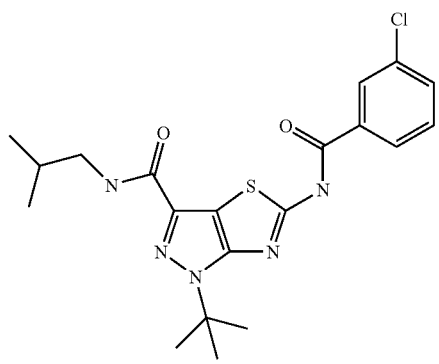

TABLE 2-continued
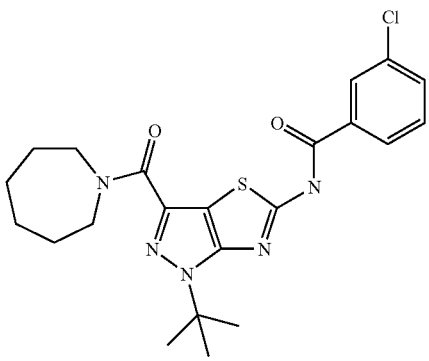
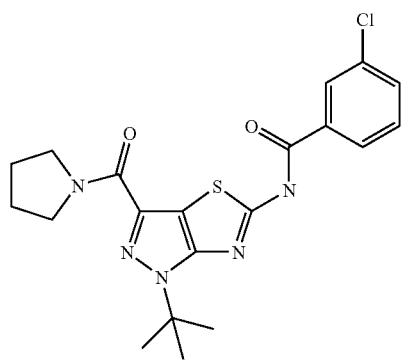
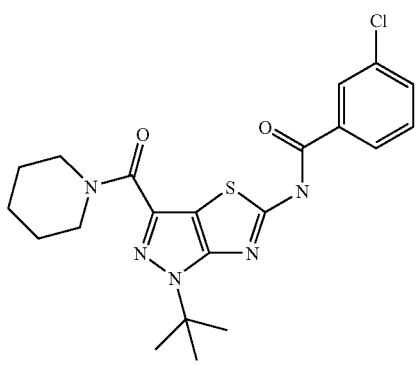
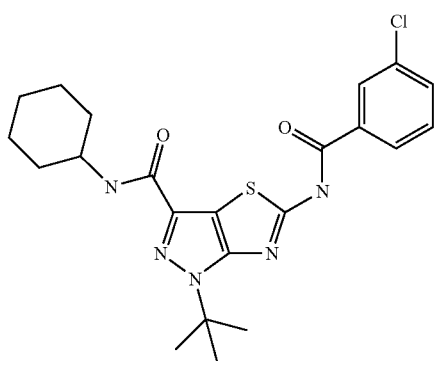

TABLE 2-continued
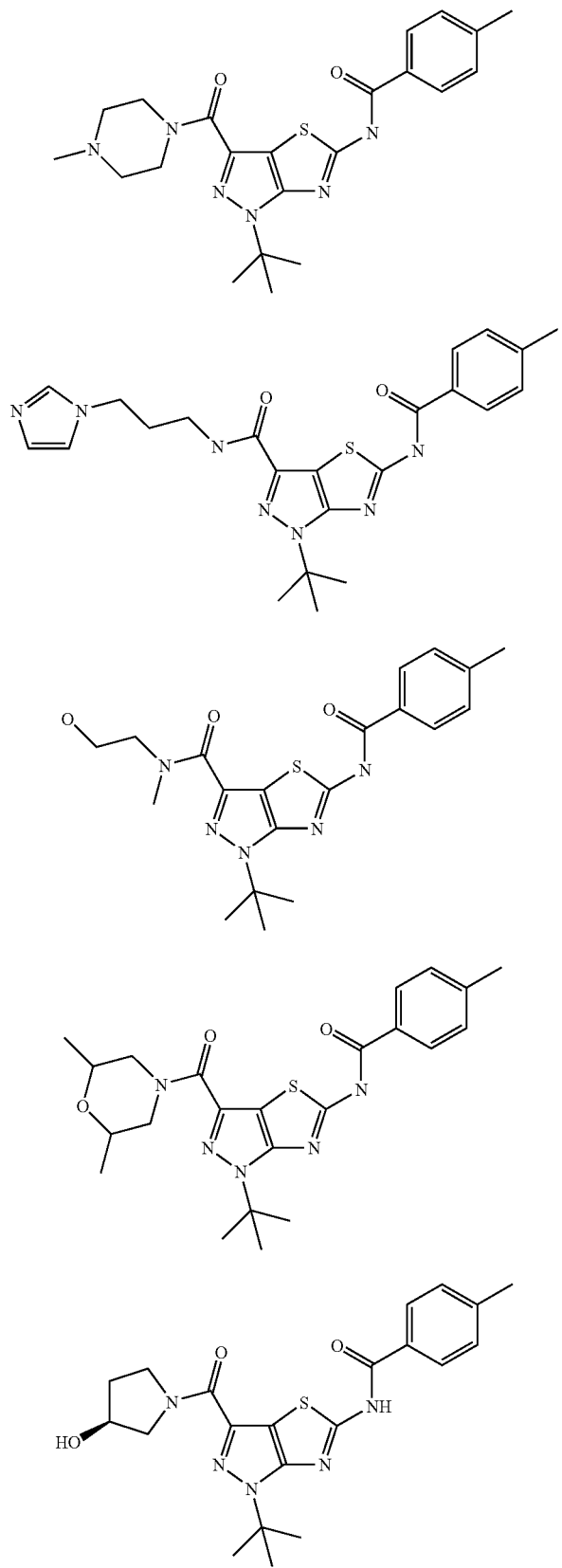

TABLE 2-continued
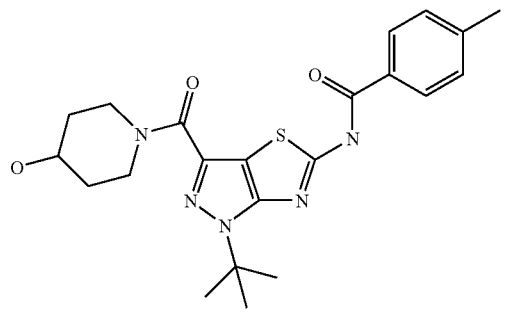
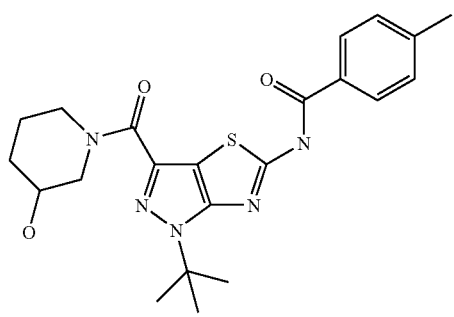
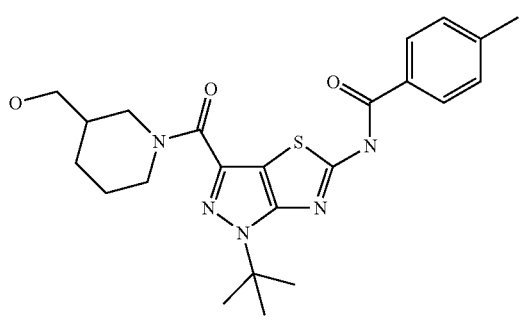
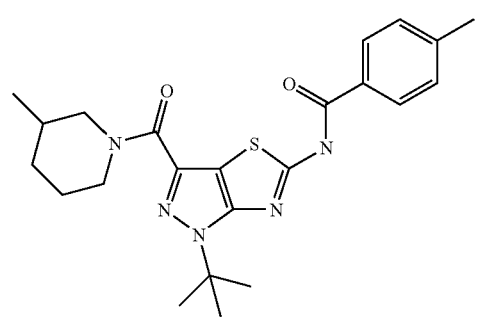
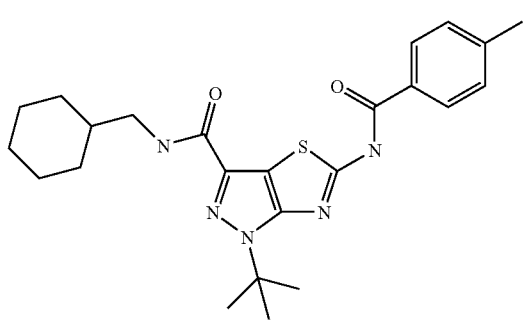

TABLE 2-continued
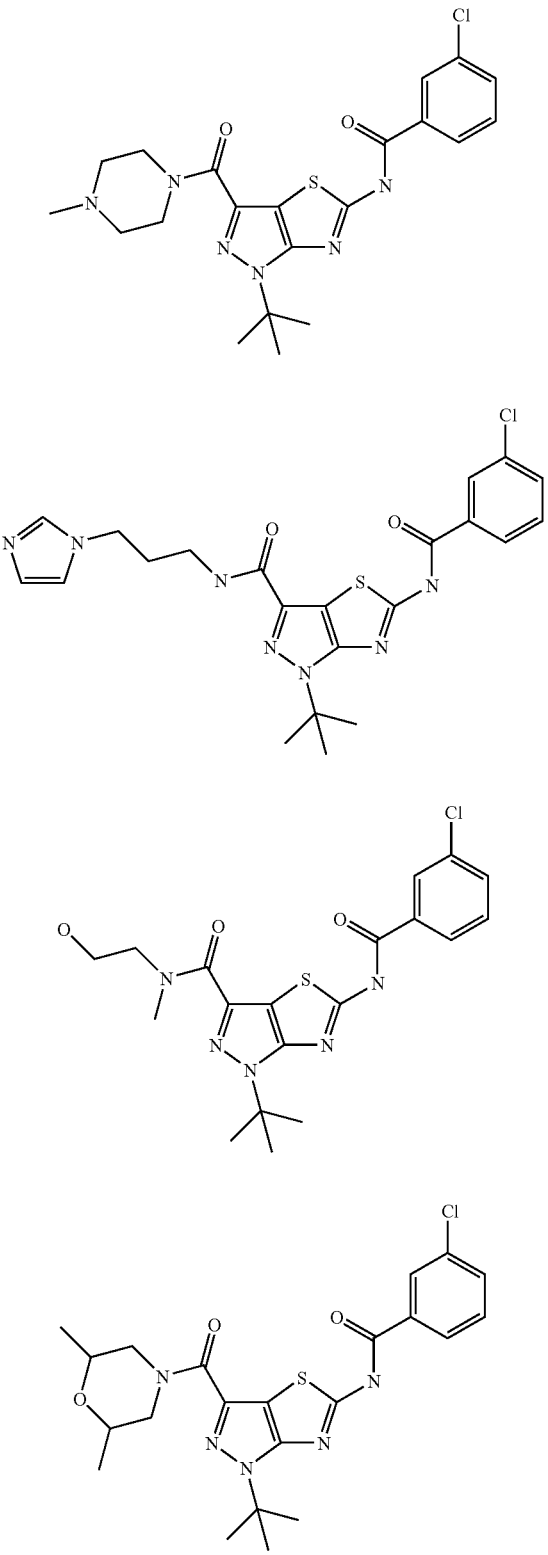

TABLE 2-continued
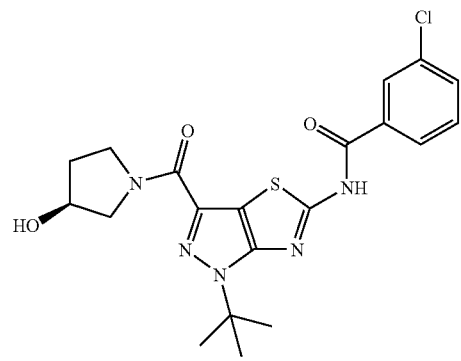
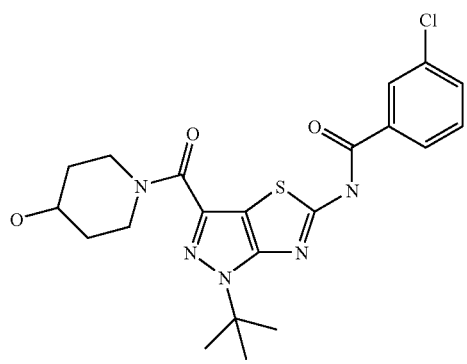
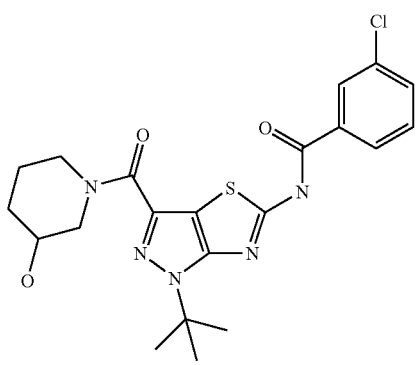
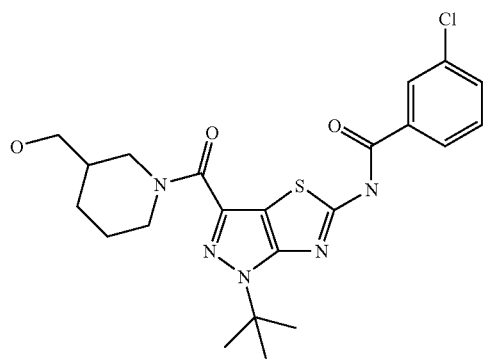

TABLE 2-continued
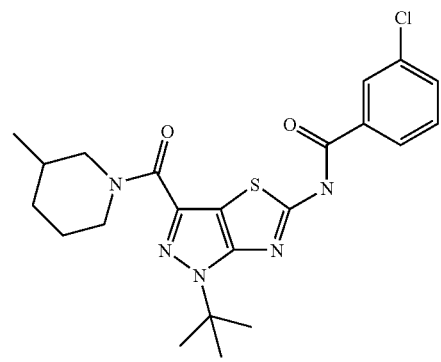
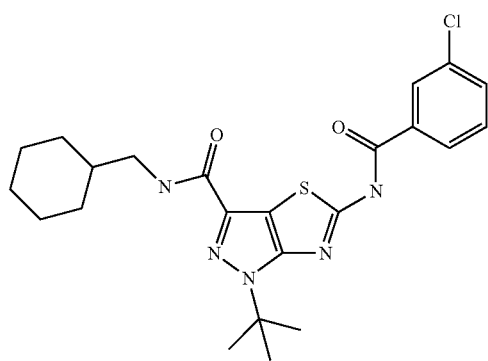
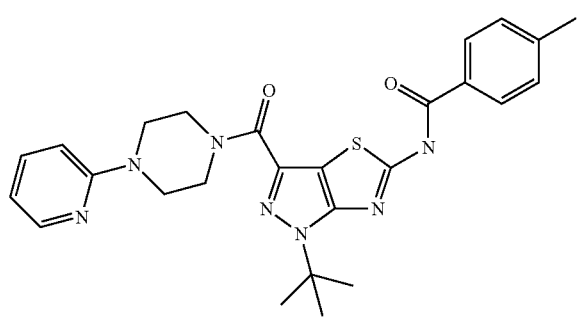
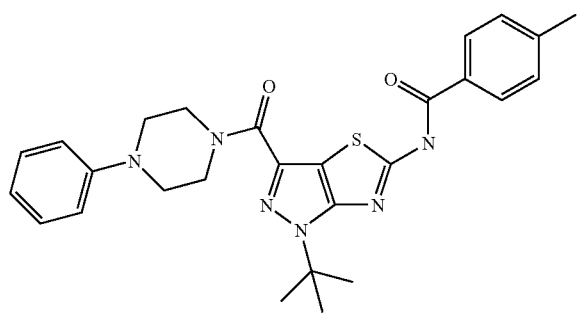

TABLE 2-continued
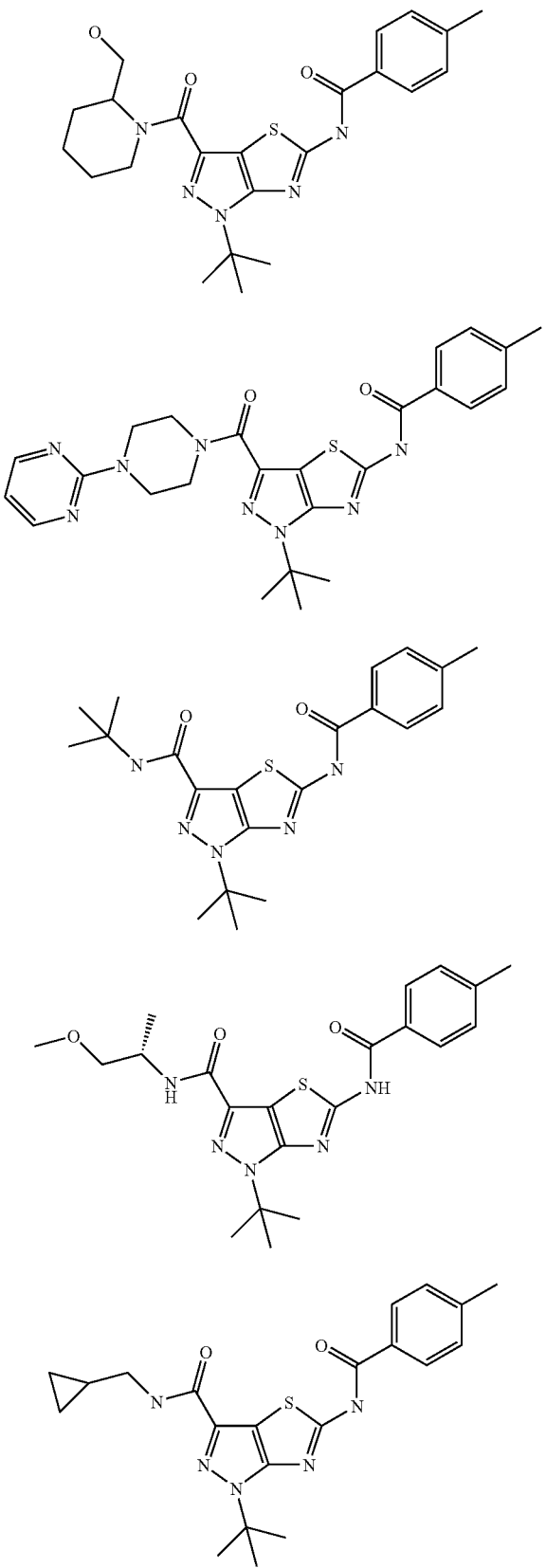

TABLE 2-continued
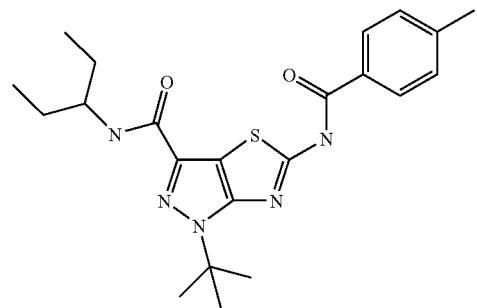
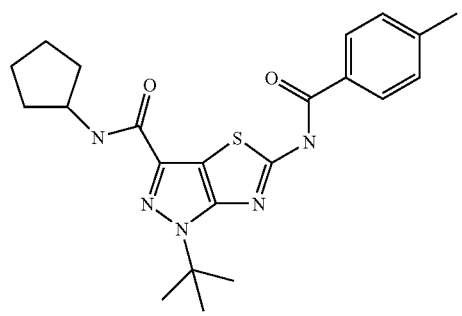
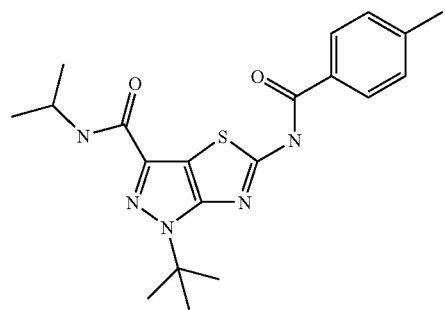
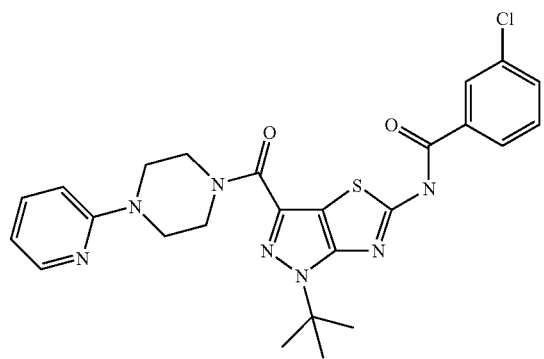

TABLE 2-continued
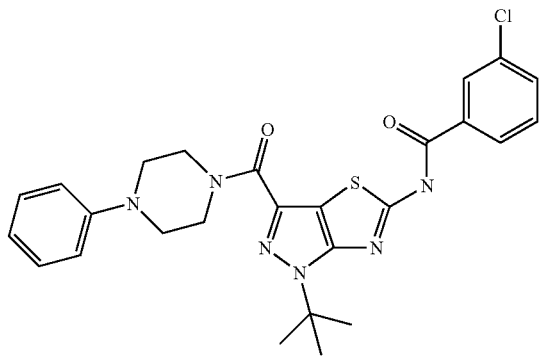
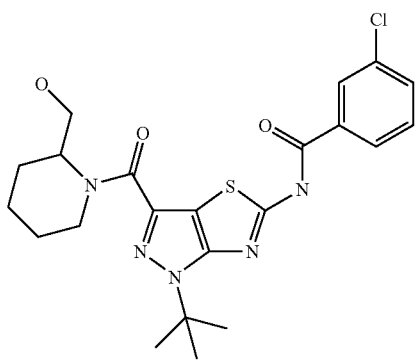
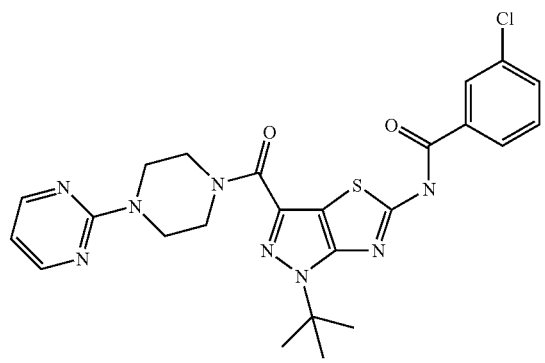
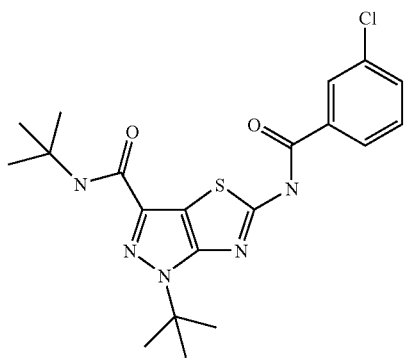

TABLE 2-continued
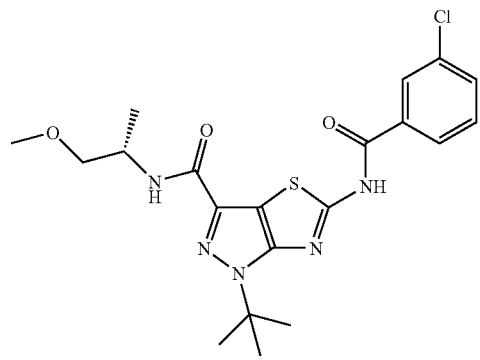
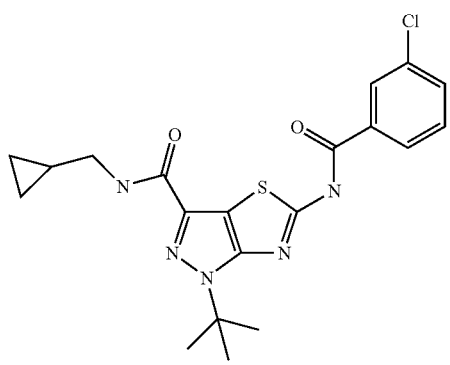
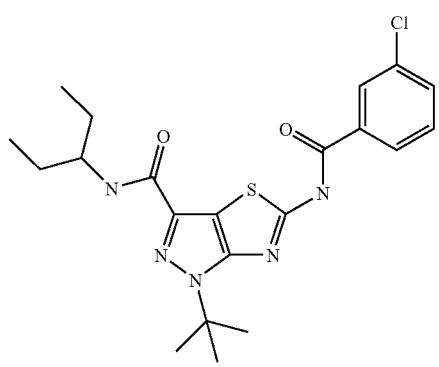
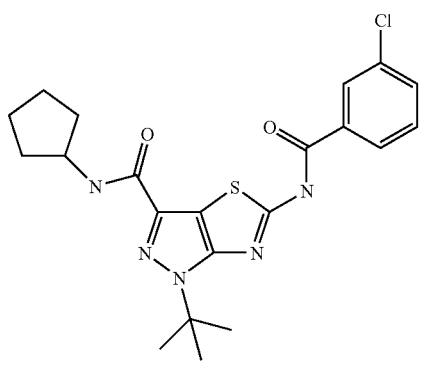

TABLE 2-continued
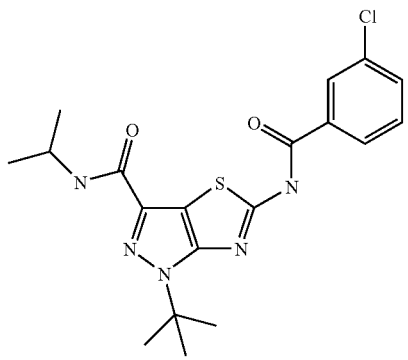
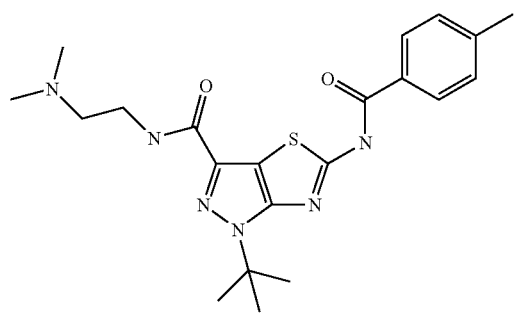
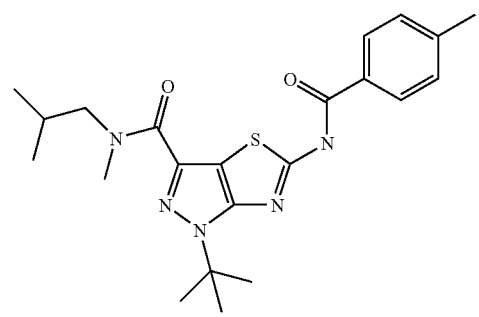
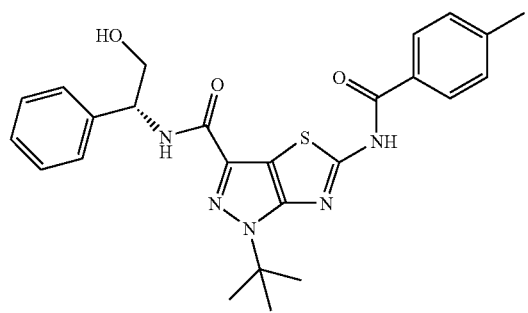

TABLE 2-continued
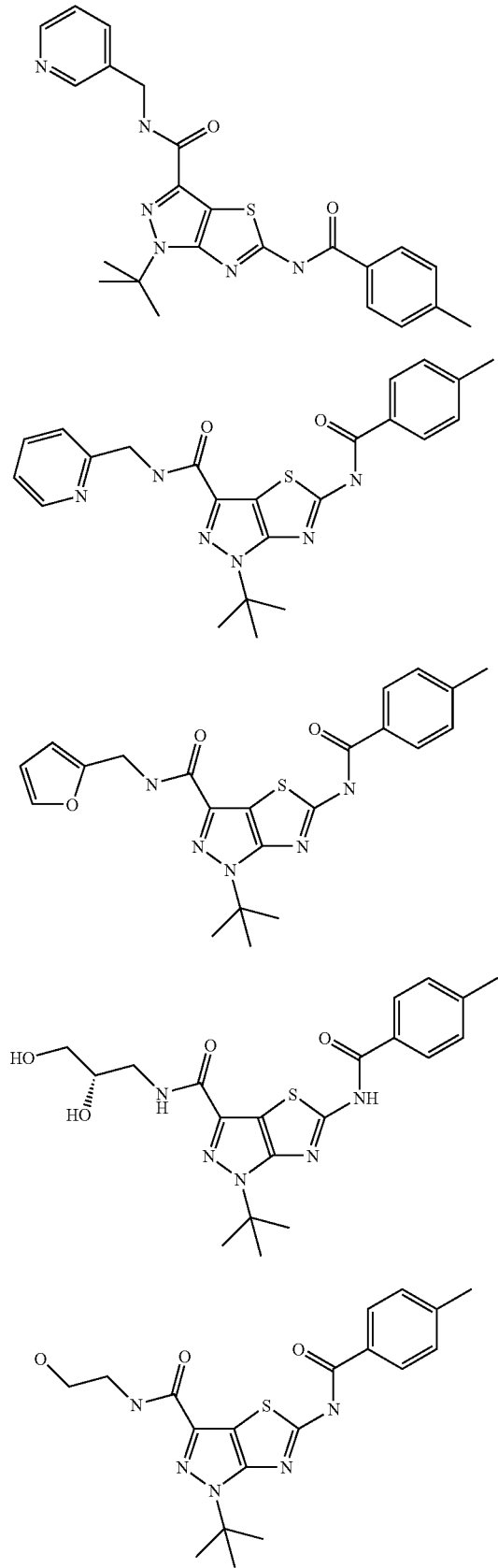

TABLE 2-continued
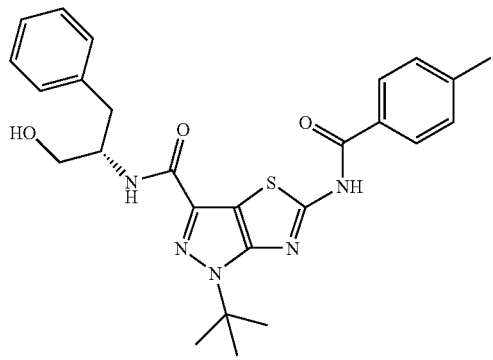
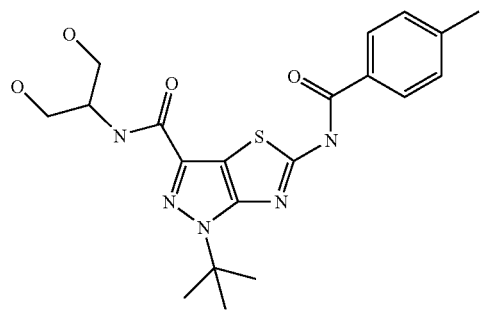
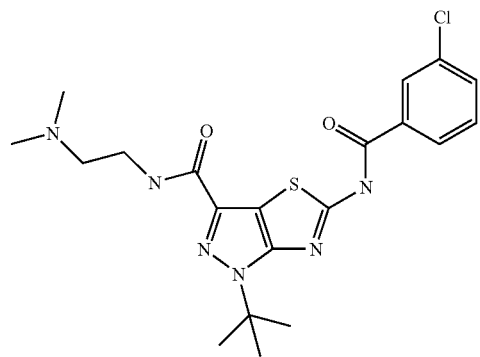
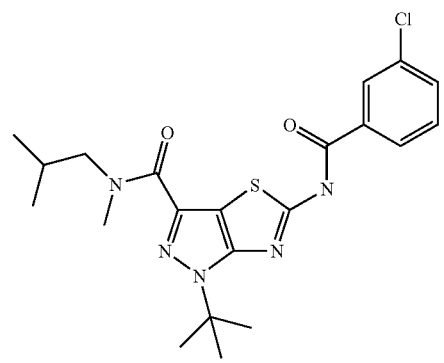

TABLE 2-continued
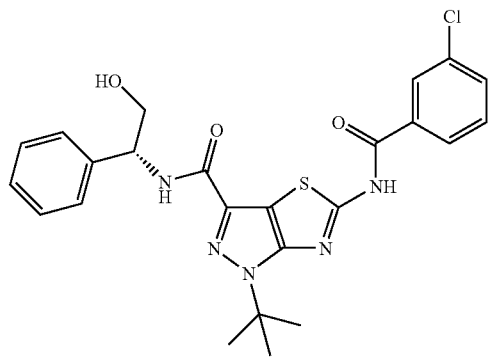
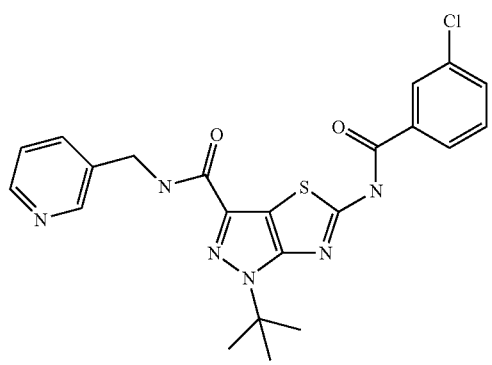
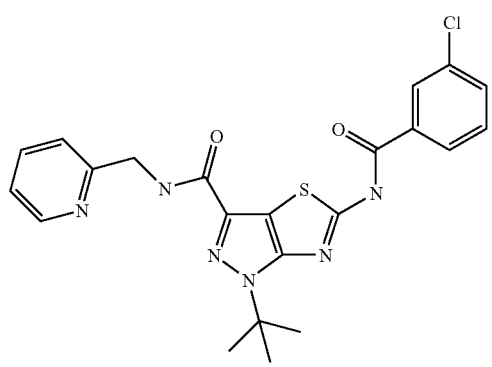
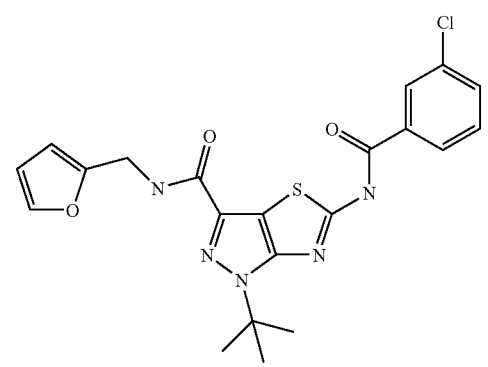

TABLE 2-continued
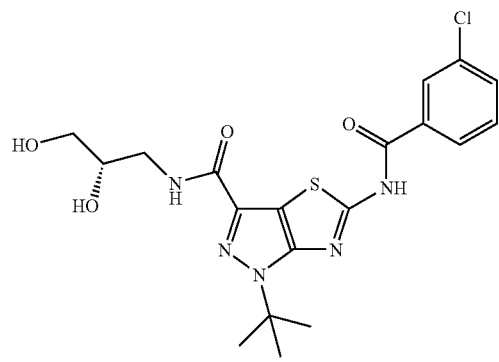
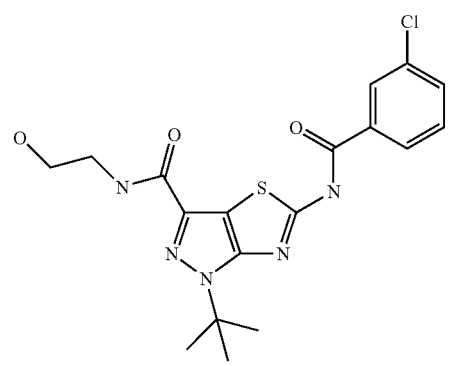
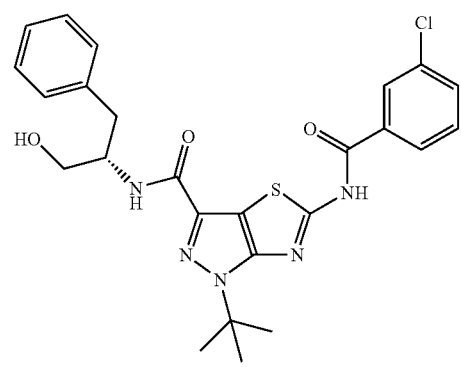
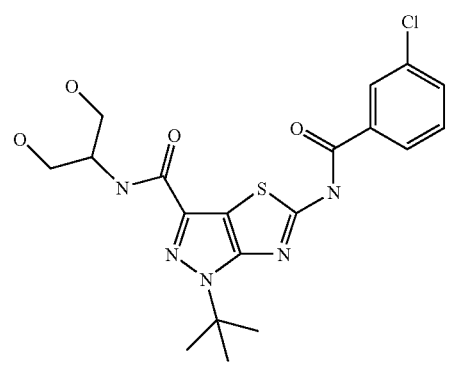

TABLE 2-continued
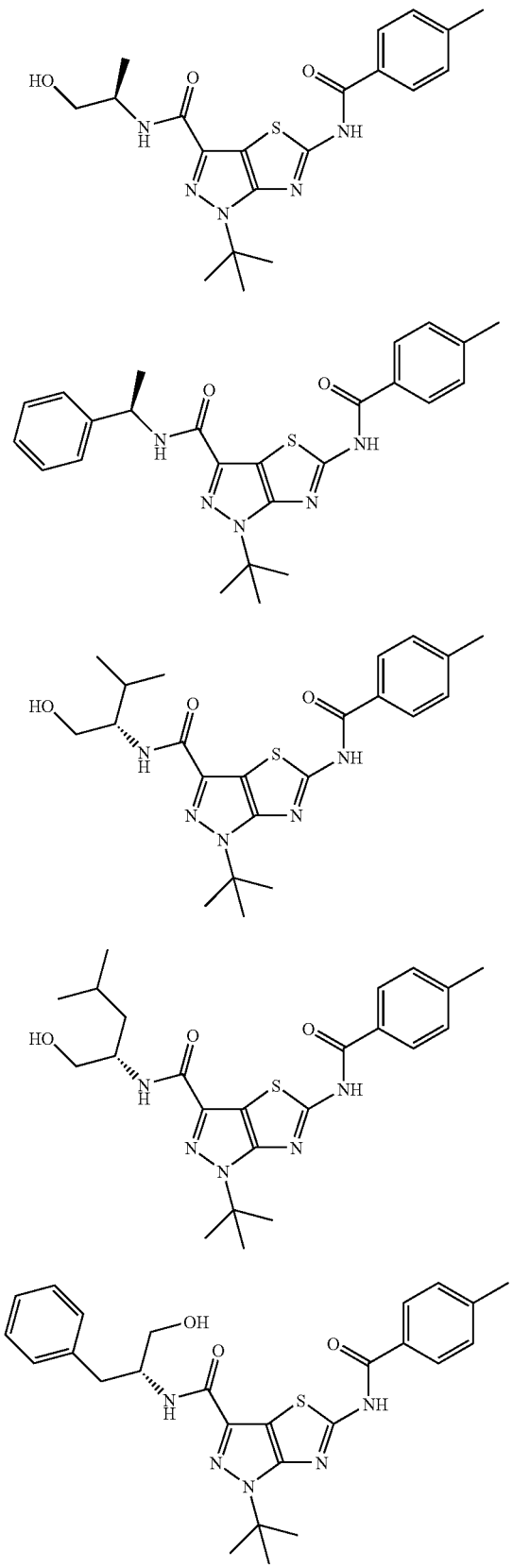

TABLE 2-continued
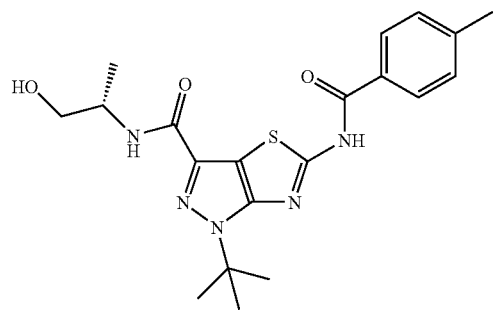
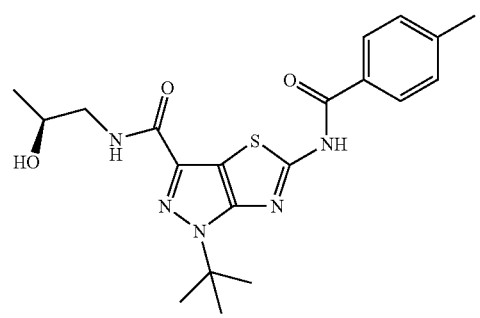
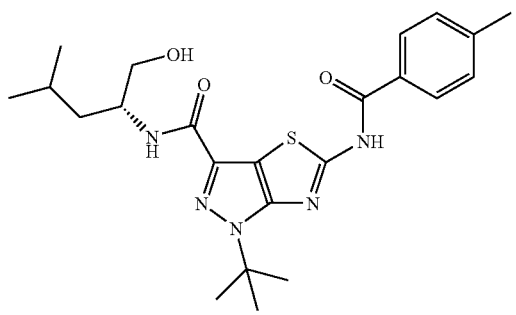
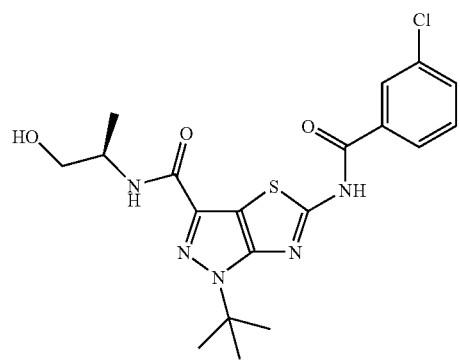

TABLE 2-continued
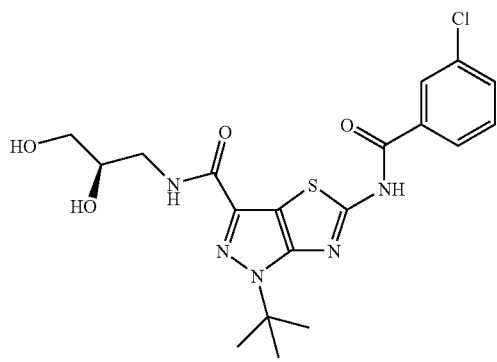
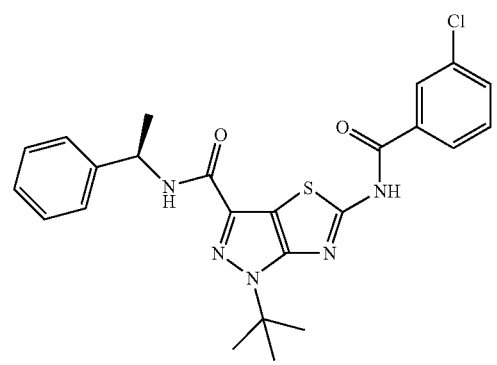
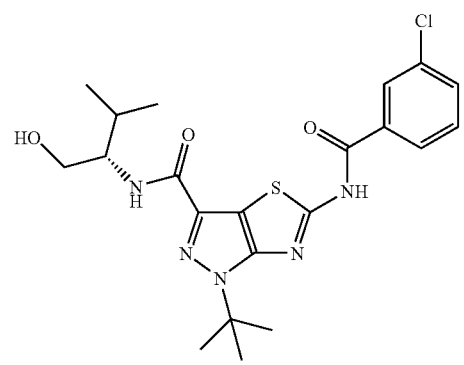
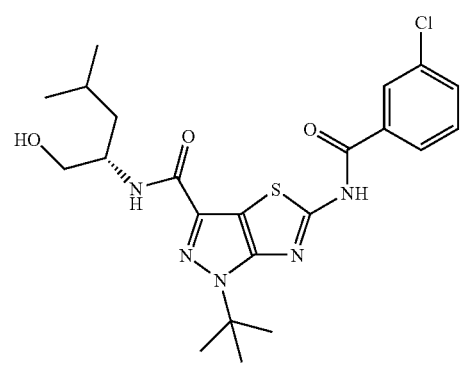

TABLE 2-continued
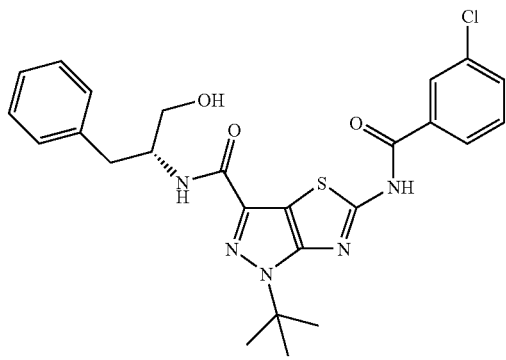
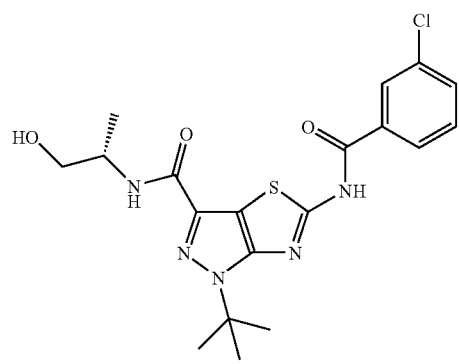
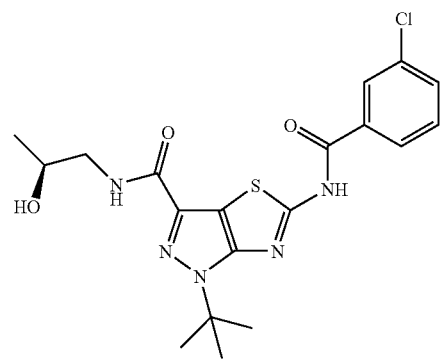
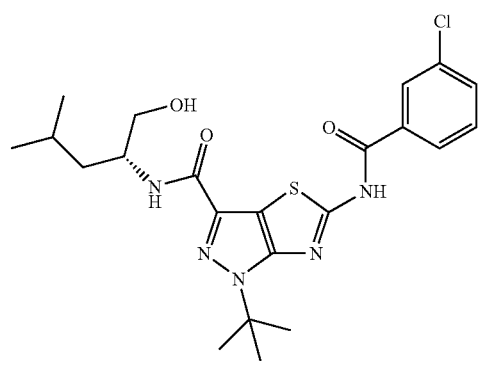

TABLE 2-continued
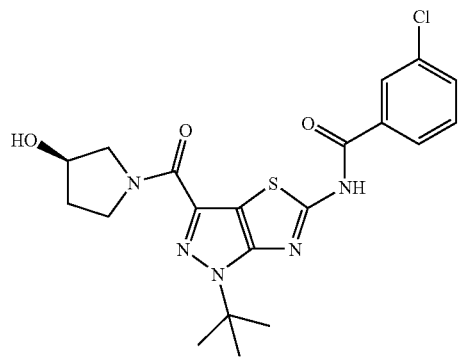
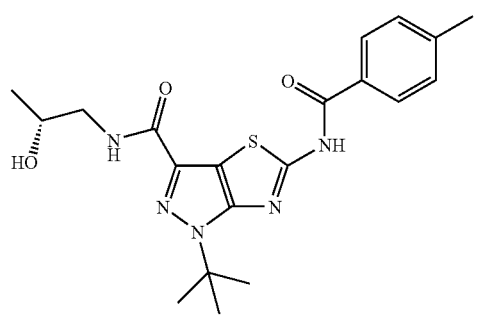
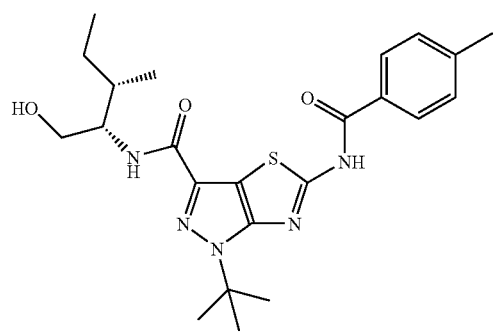
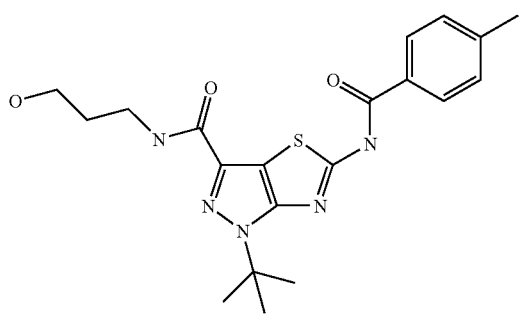

TABLE 2-continued
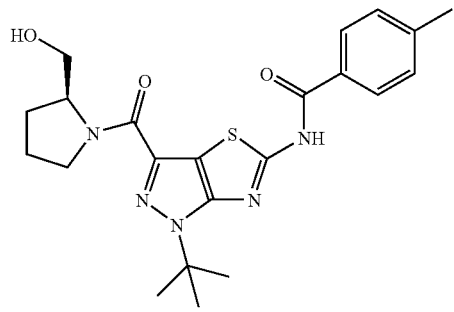
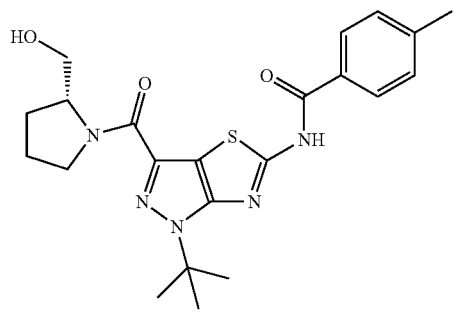
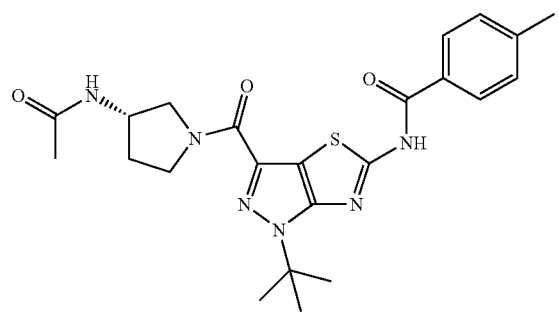
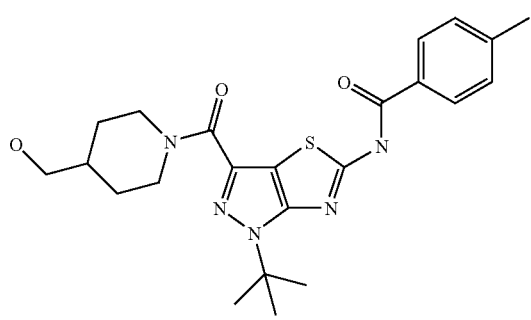
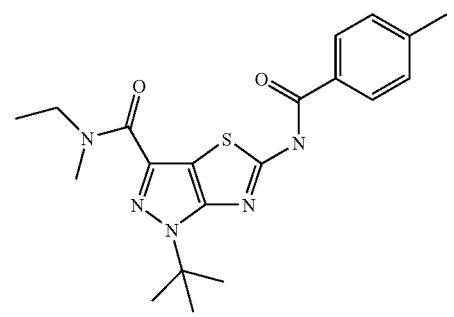

TABLE 2-continued
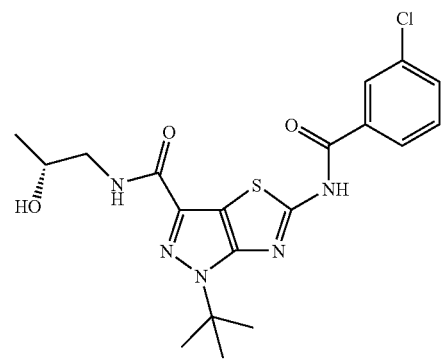
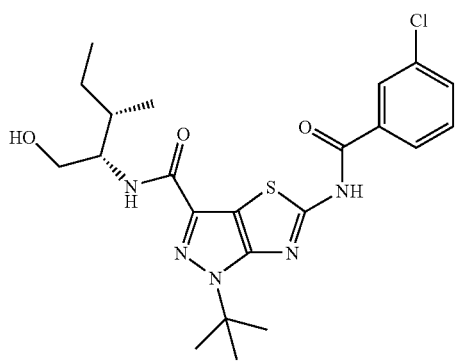
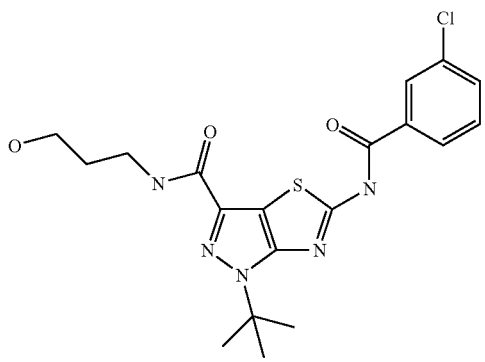
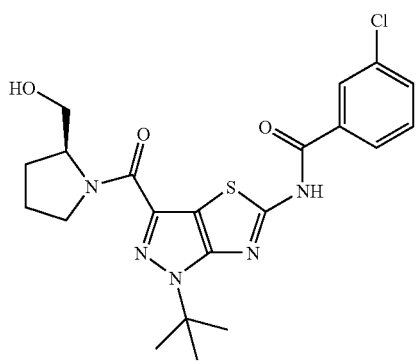

TABLE 2-continued
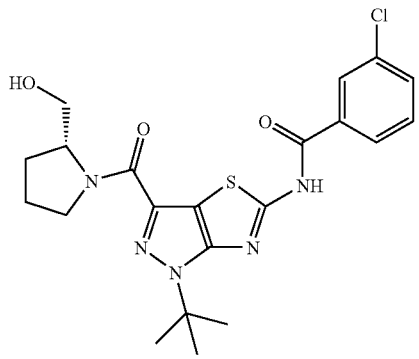
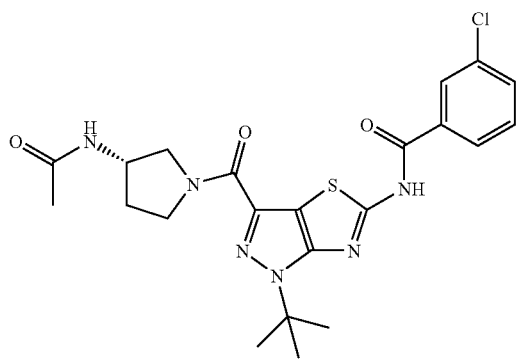
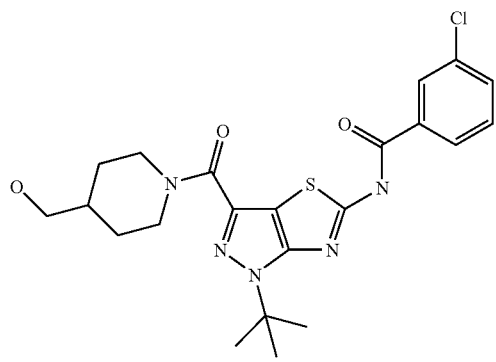
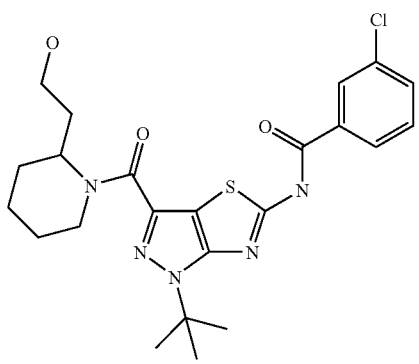

TABLE 2-continued
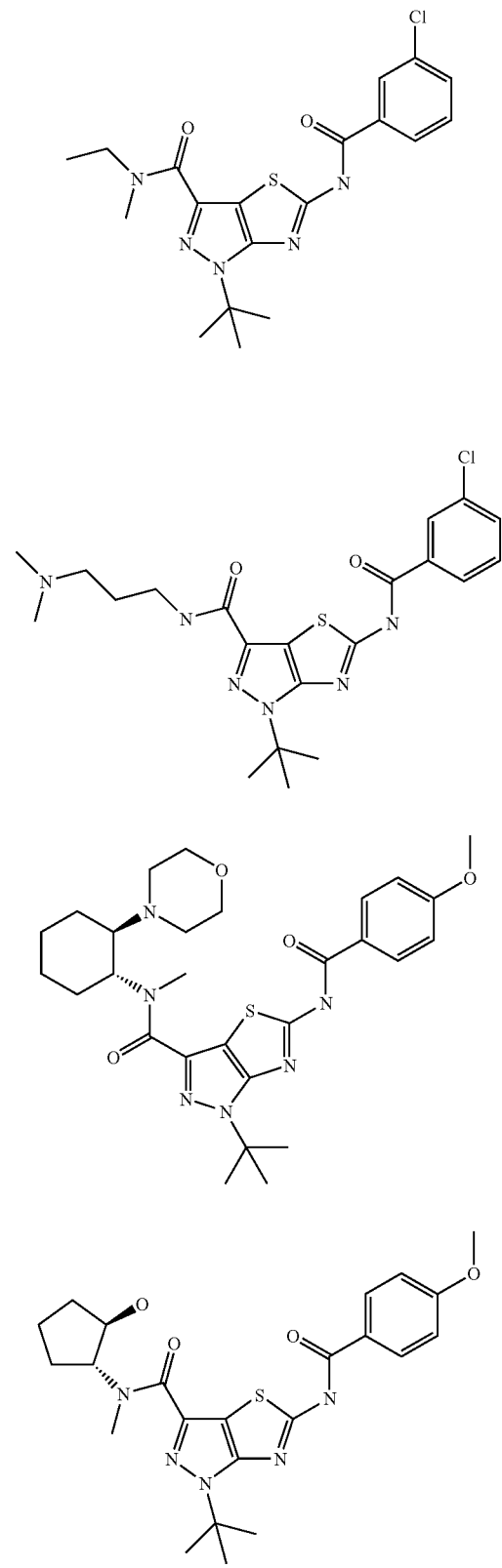

TABLE 2-continued
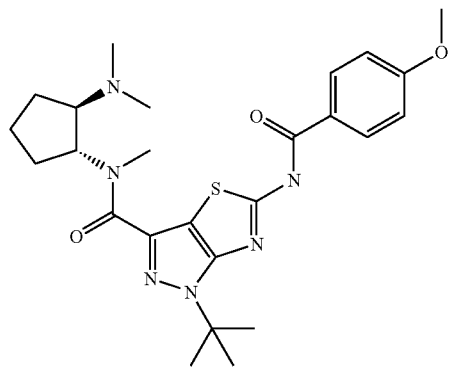
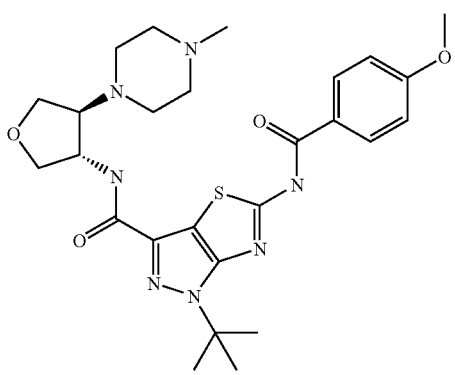
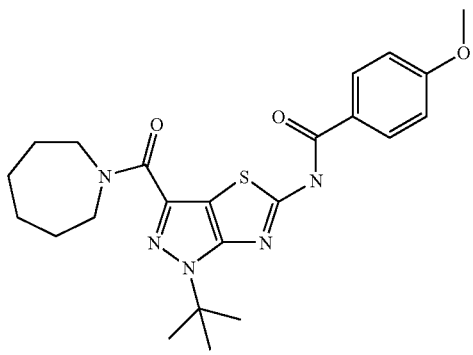
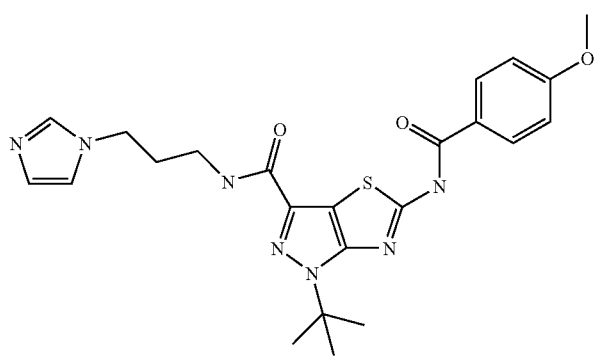

TABLE 2-continued
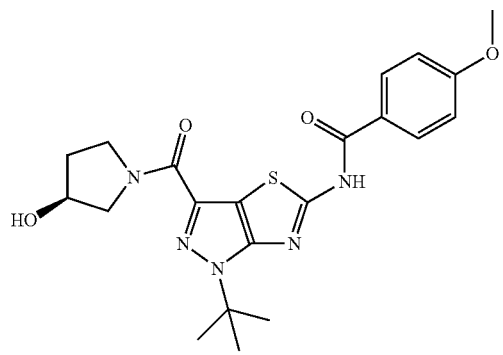
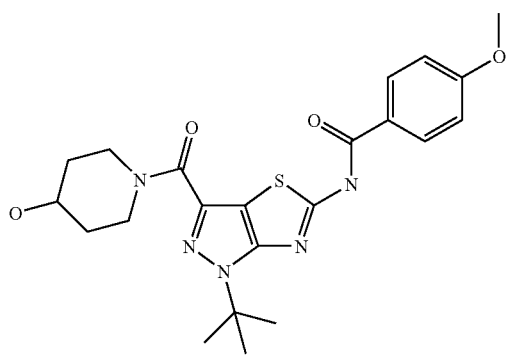
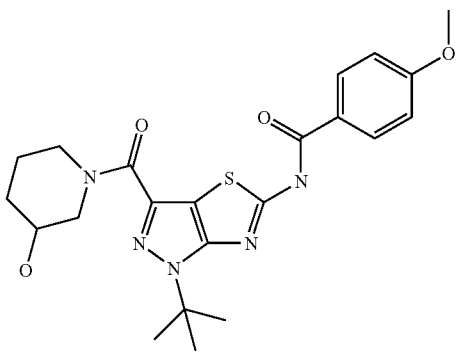
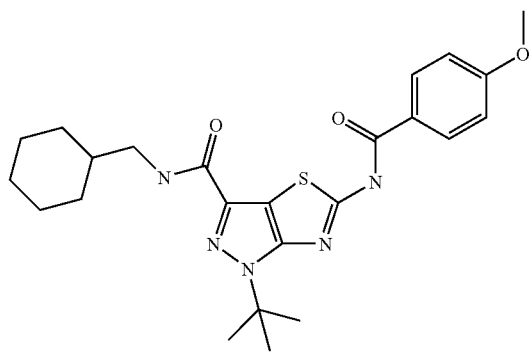

TABLE 2-continued
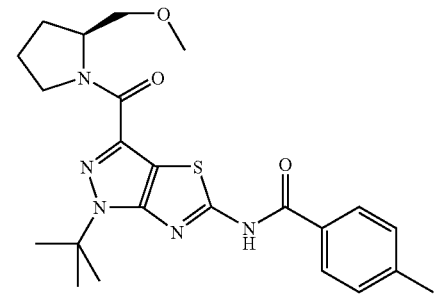
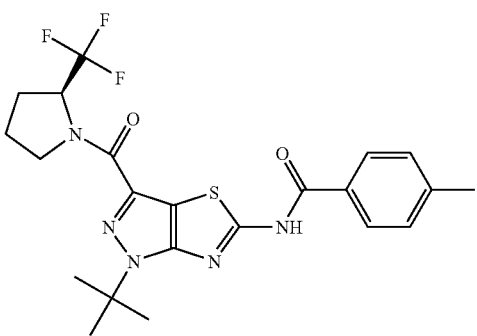
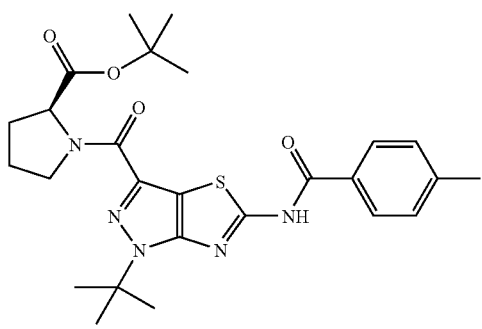
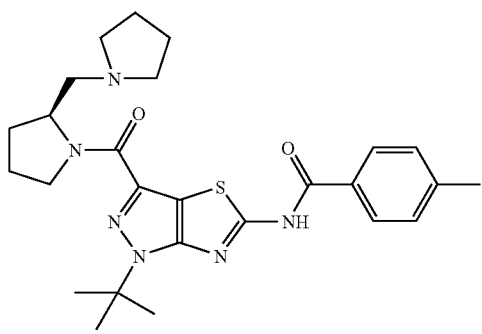
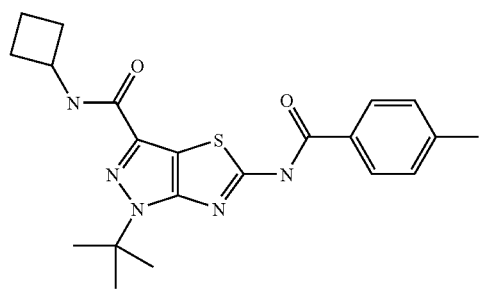

TABLE 2-continued
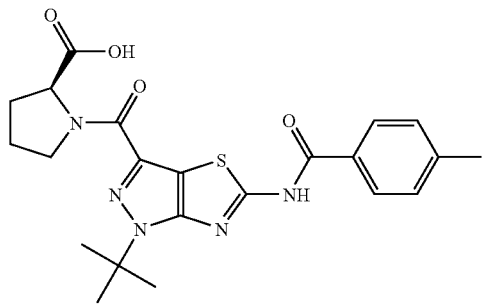
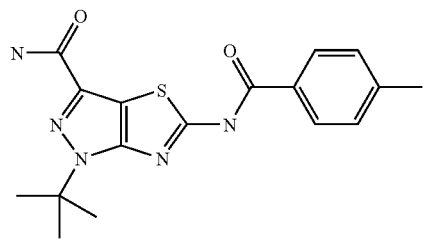
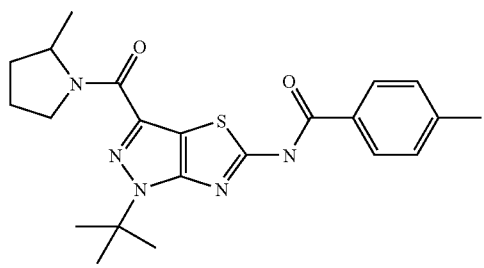
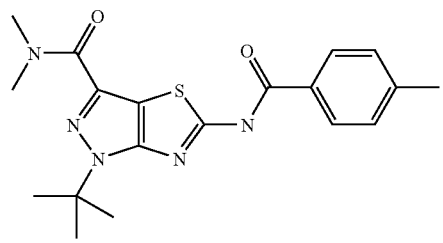
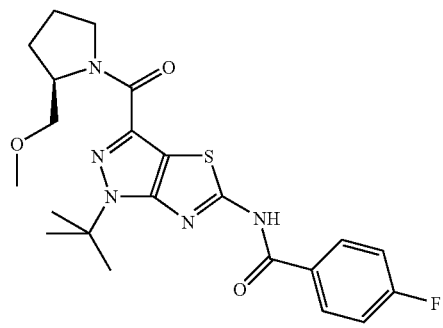

TABLE 2-continued
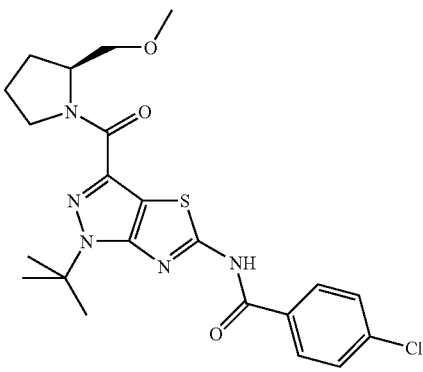
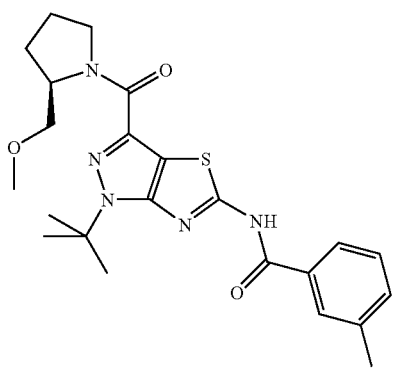
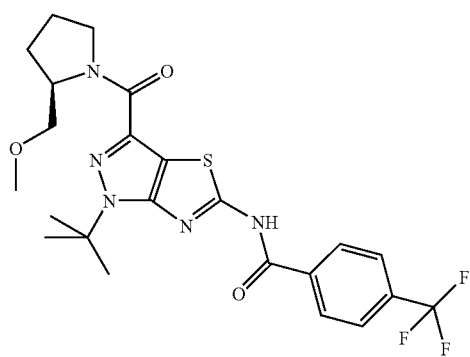
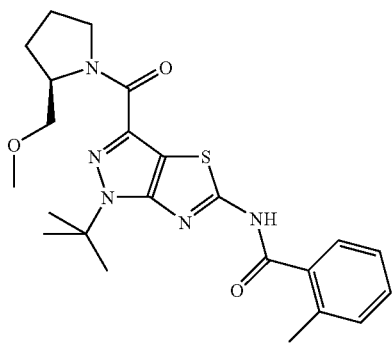

TABLE 2-continued
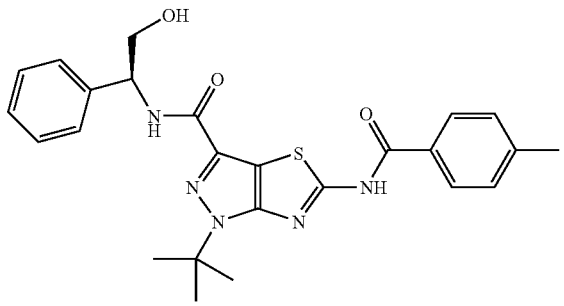
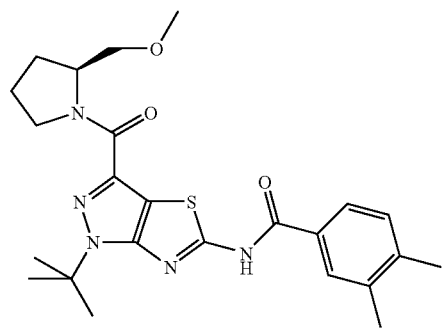
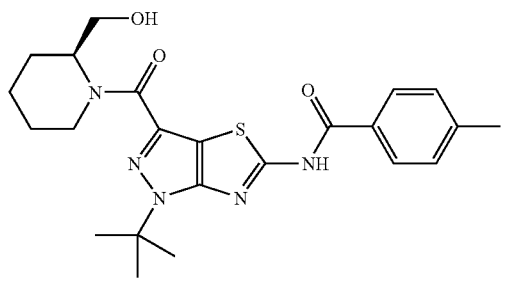
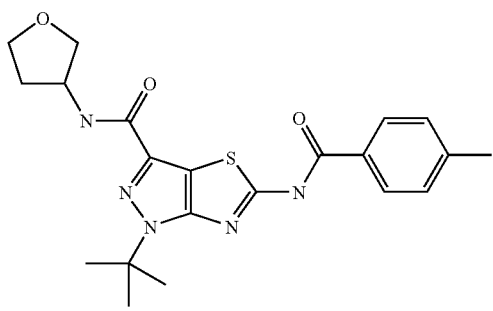
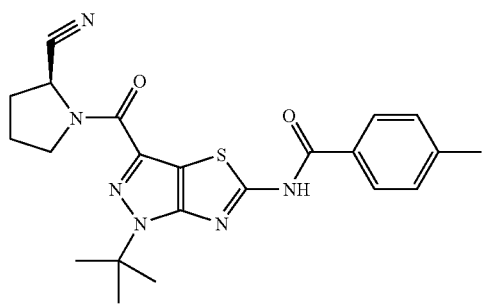

TABLE 2-continued
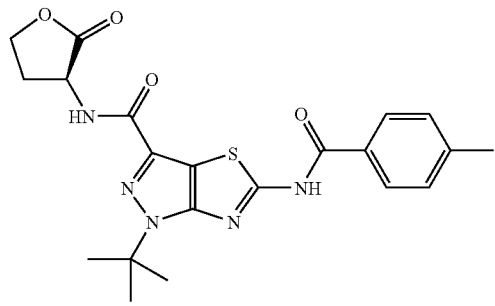
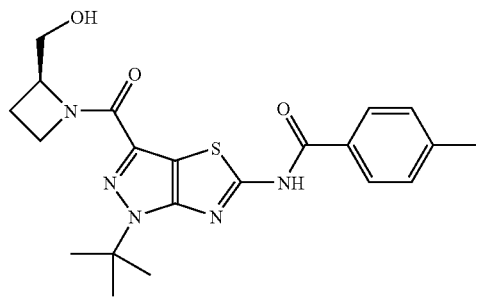
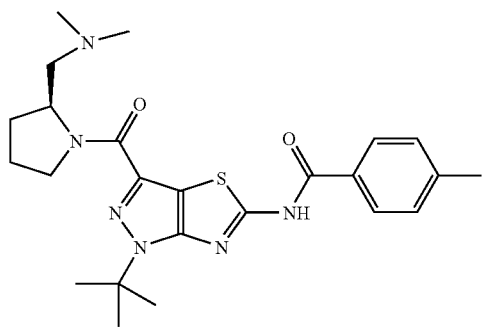
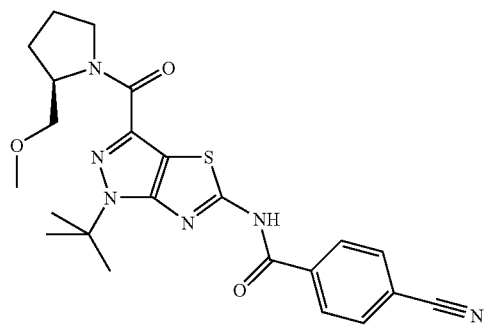

TABLE 2-continued
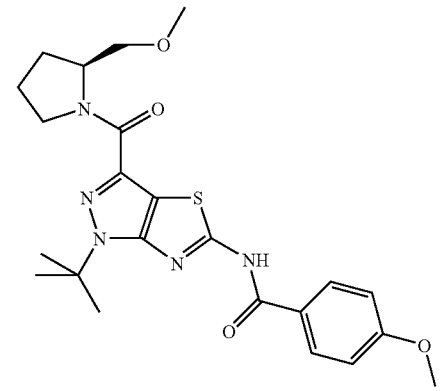
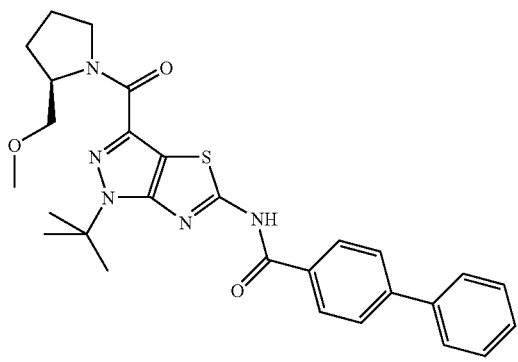
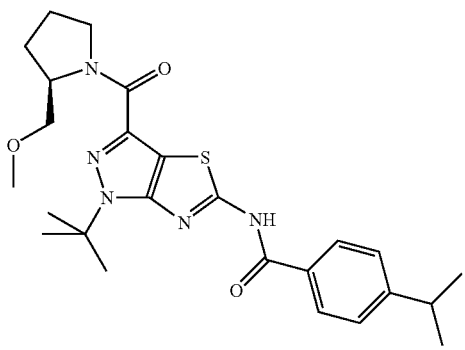
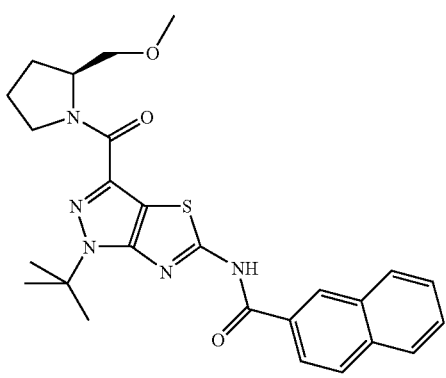

TABLE 2-continued
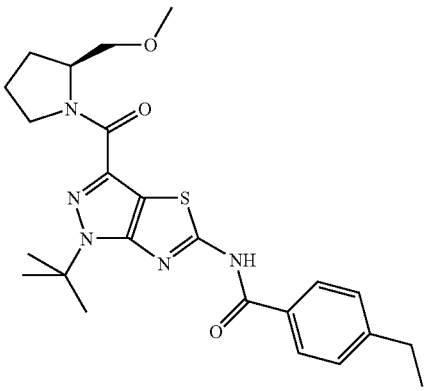
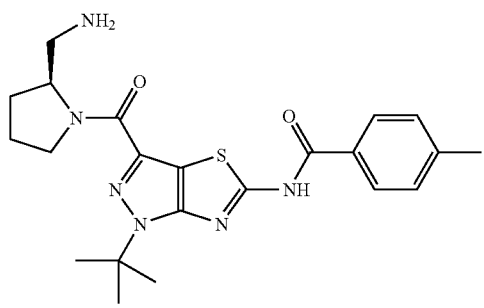
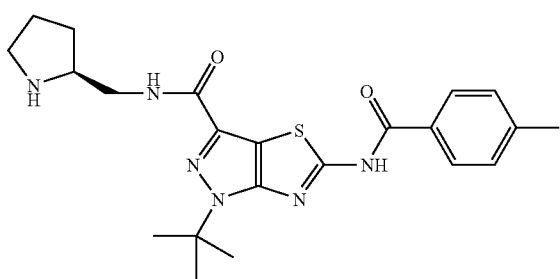
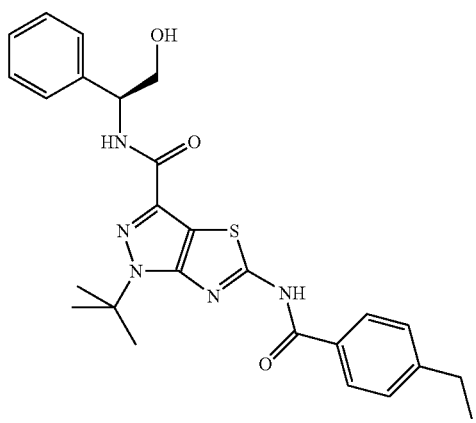

TABLE 2-continued
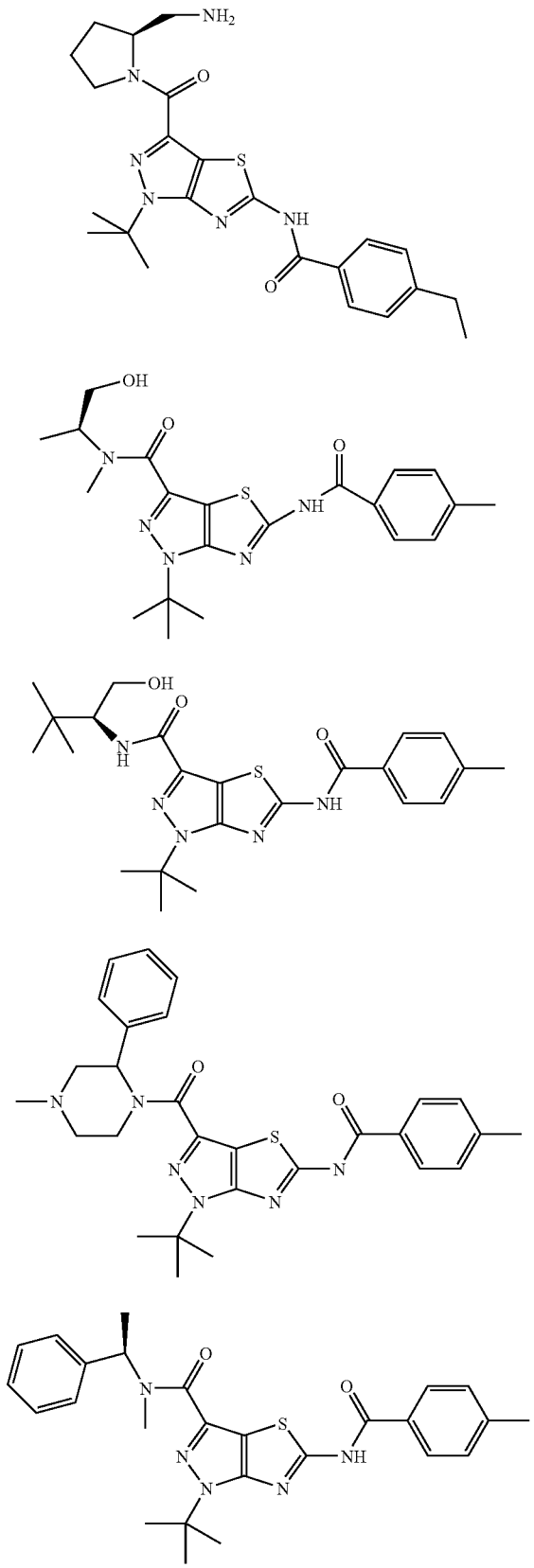

TABLE 2-continued
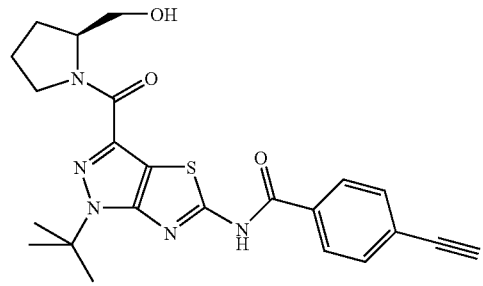
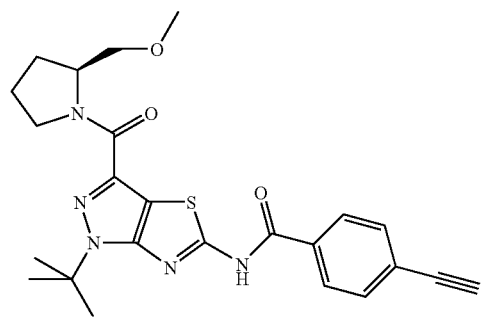
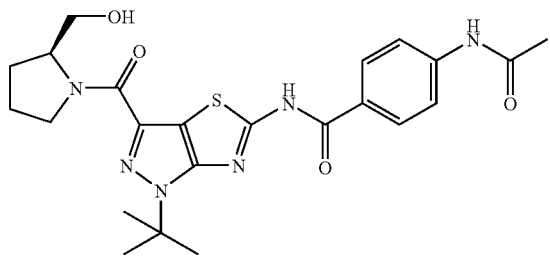
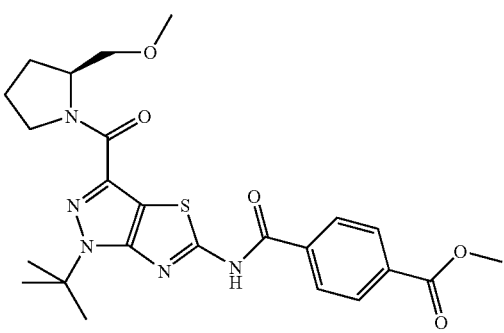
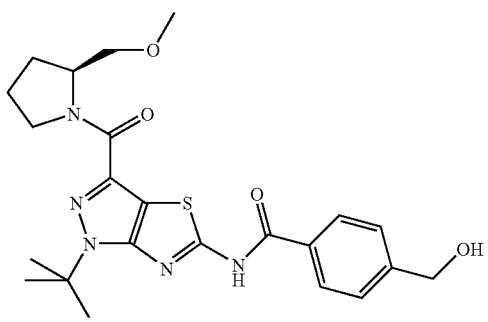

TABLE 2-continued
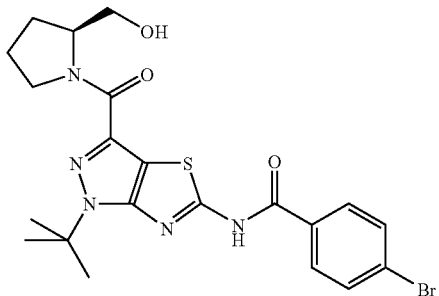
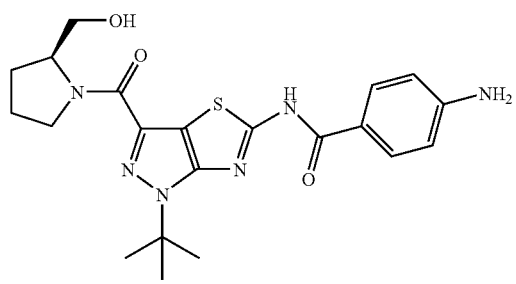
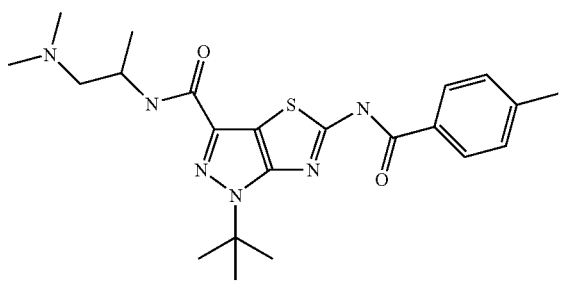
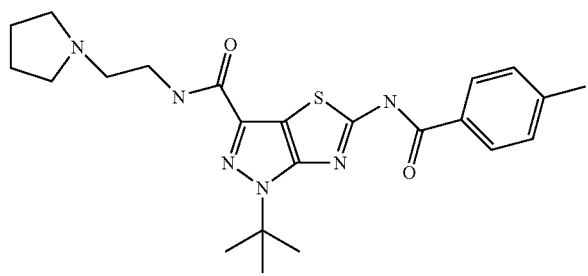
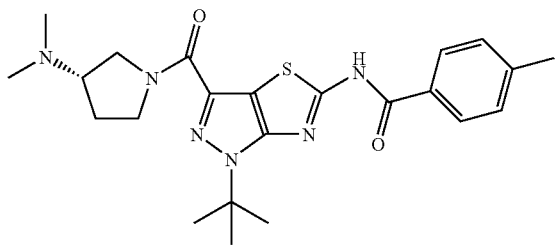

TABLE 2-continued
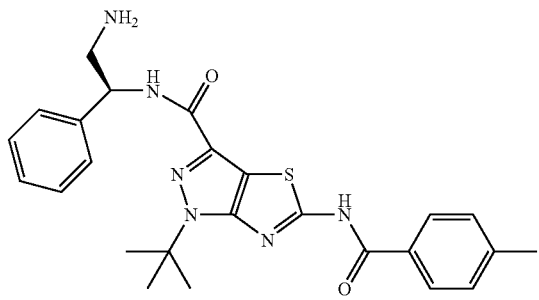
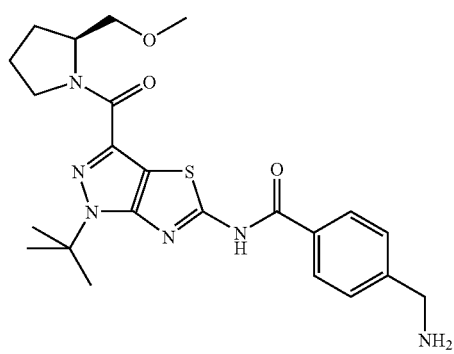
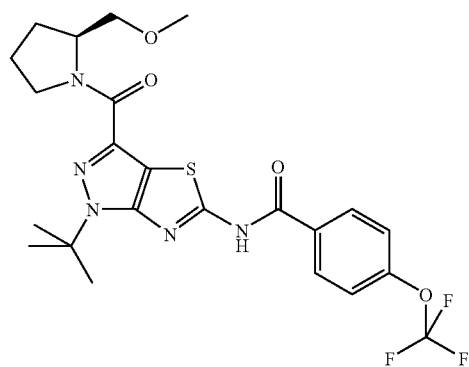
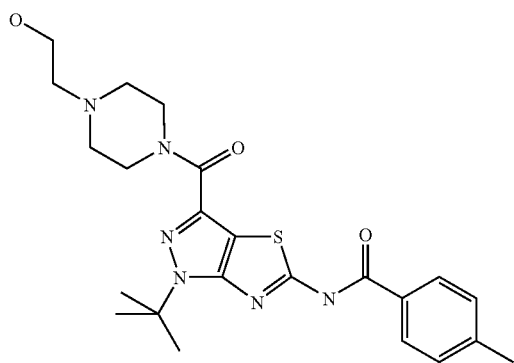

TABLE 2-continued
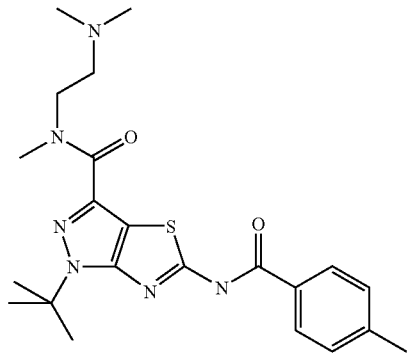
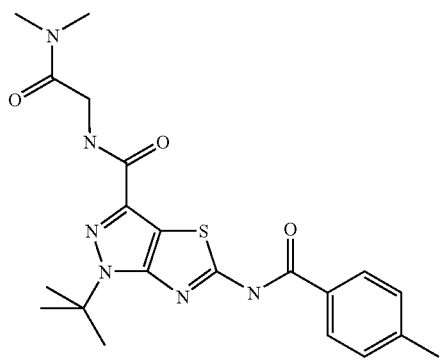
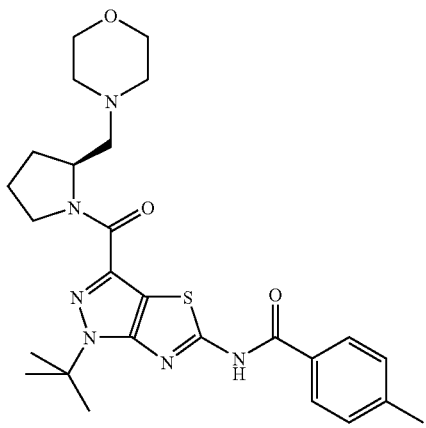
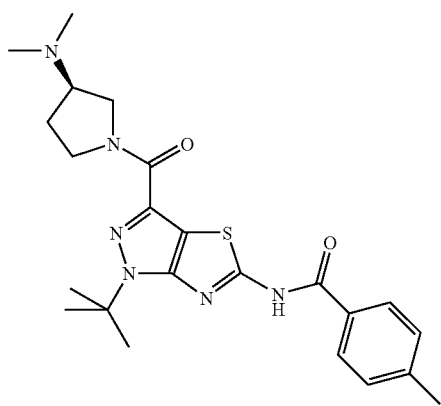

TABLE 2-continued
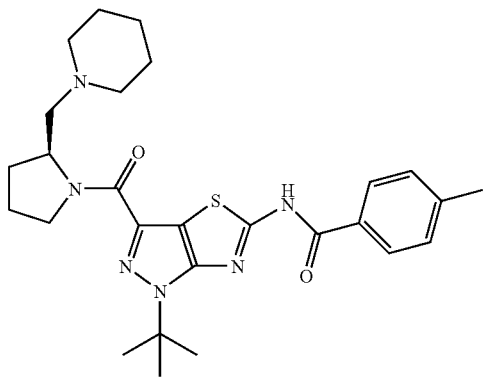
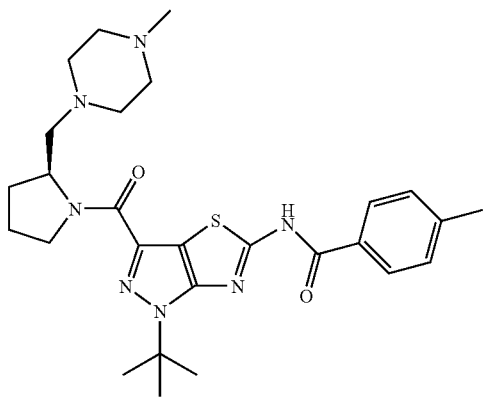
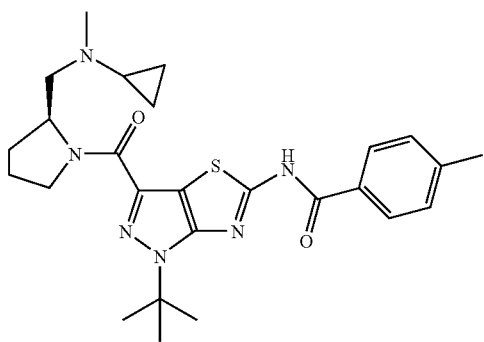
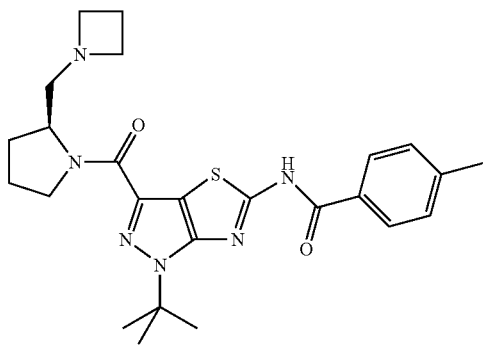

TABLE 2-continued
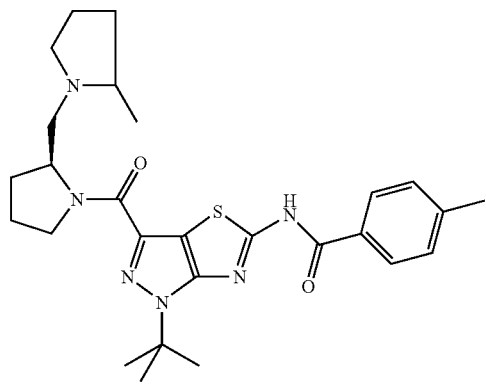
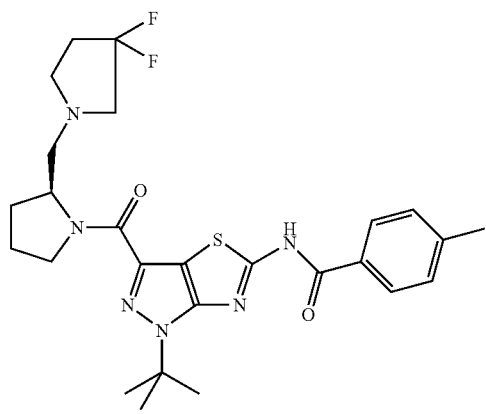
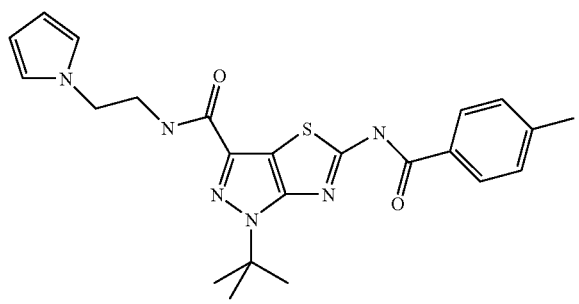
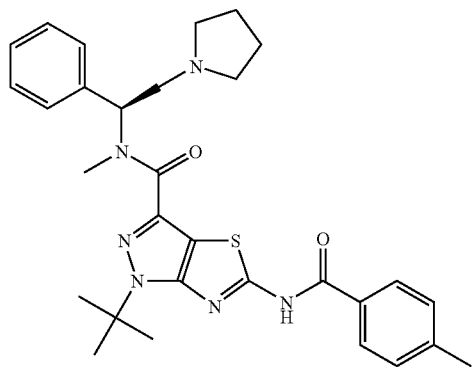

TABLE 2-continued
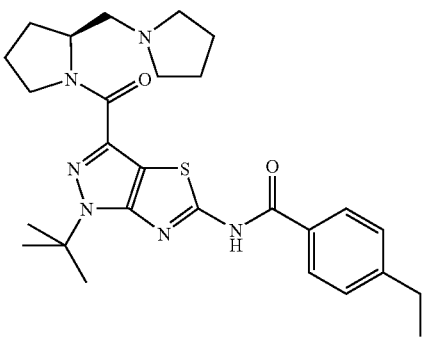
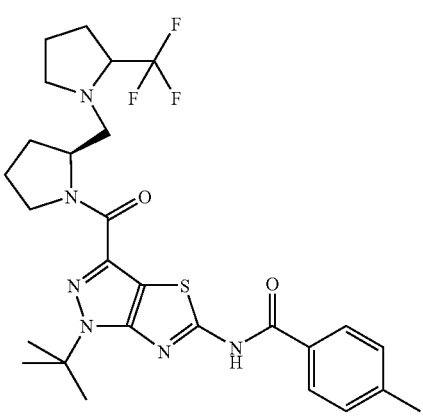
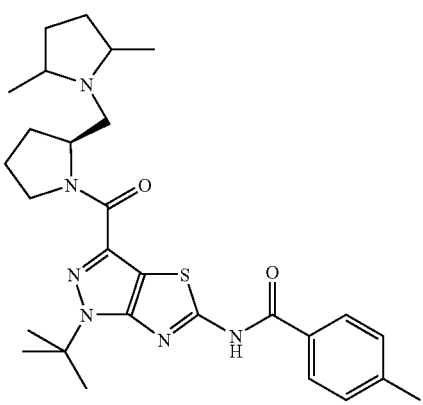
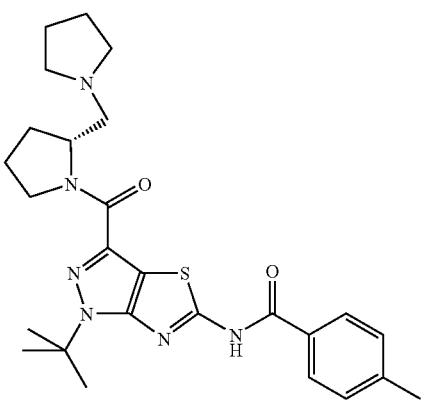

TABLE 2-continued
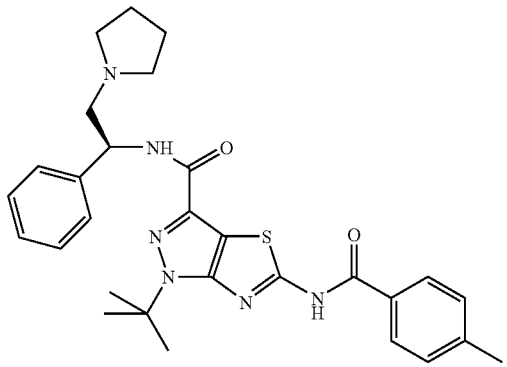
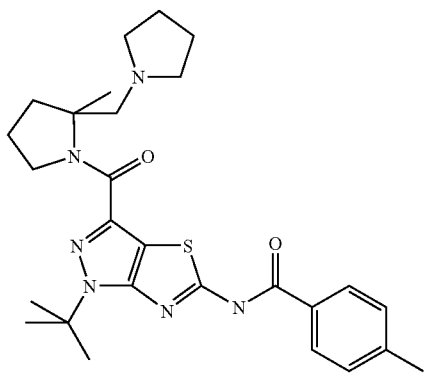
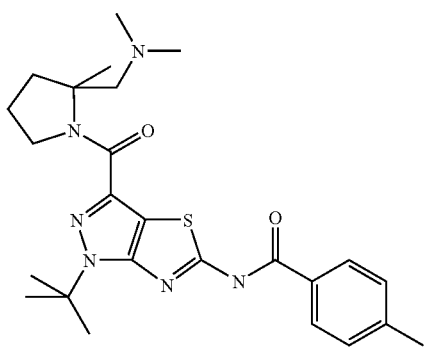
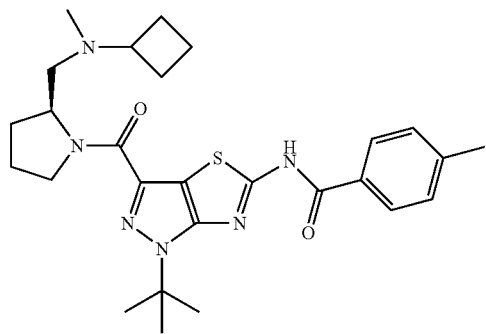

TABLE 2-continued
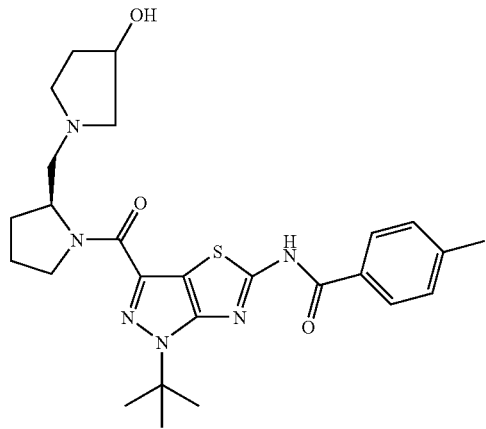
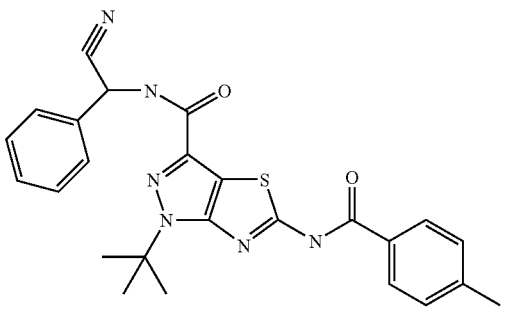
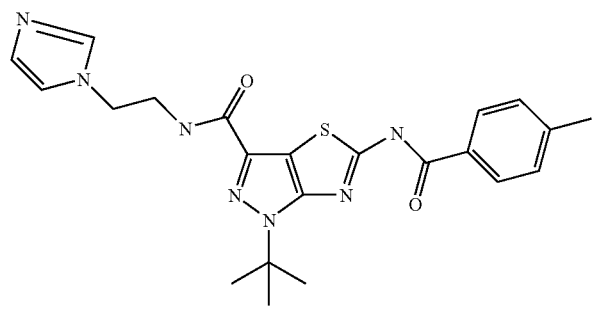
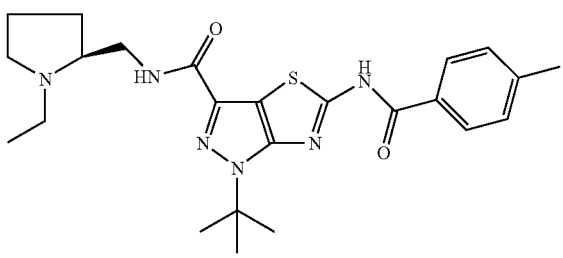
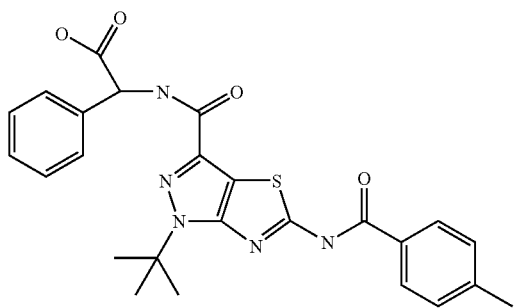

TABLE 2-continued
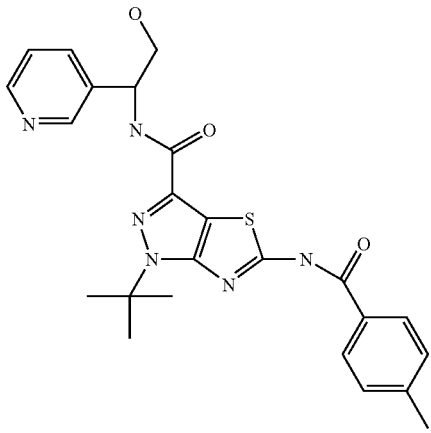
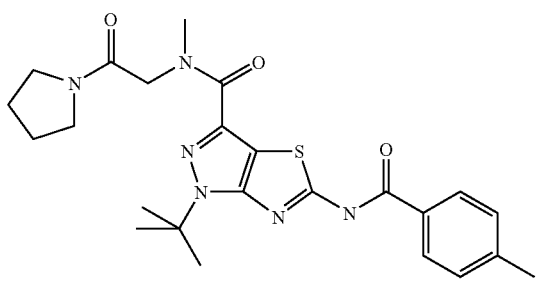
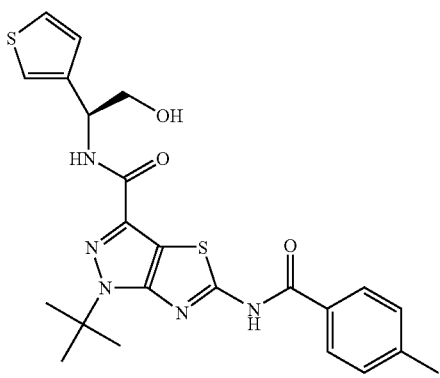
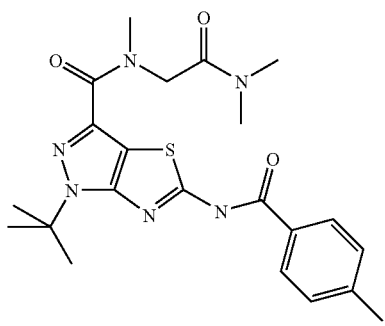

TABLE 2-continued
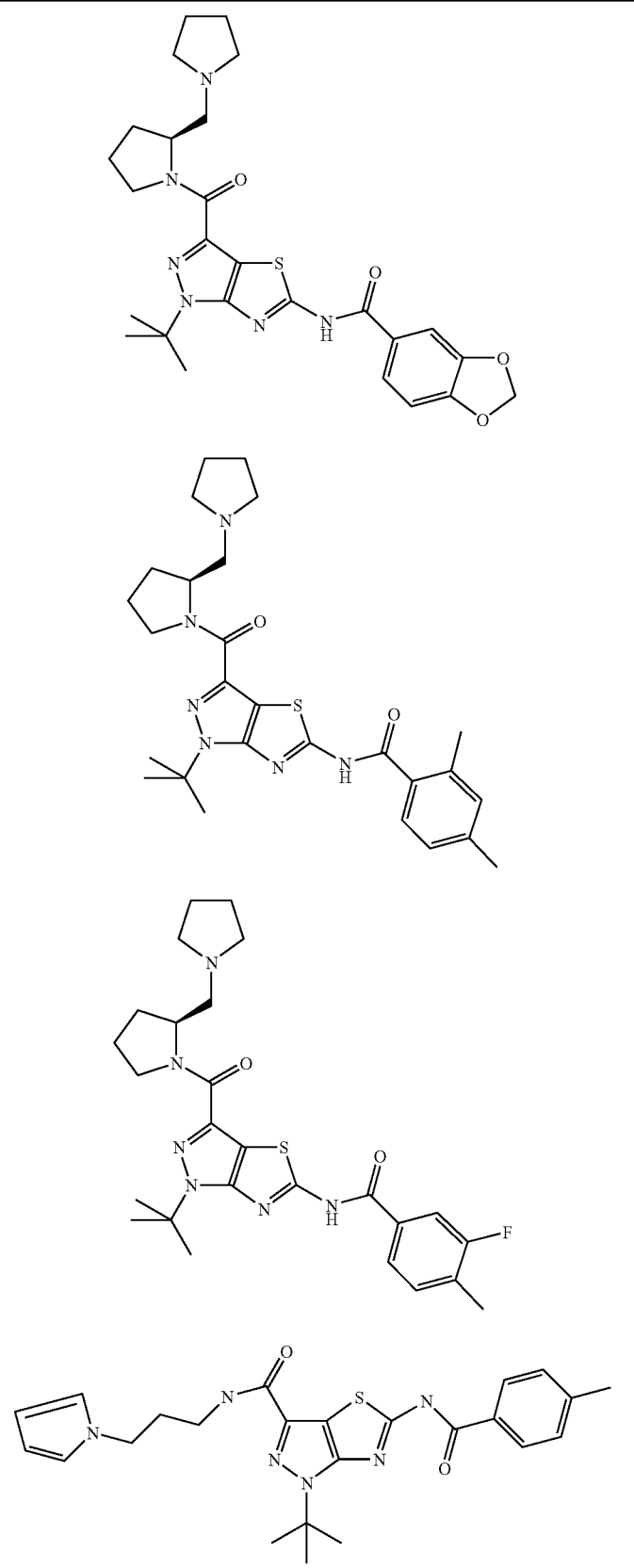

TABLE 2-continued
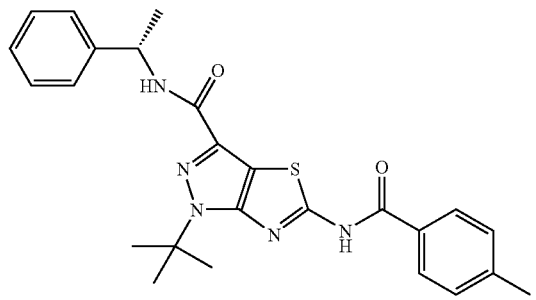
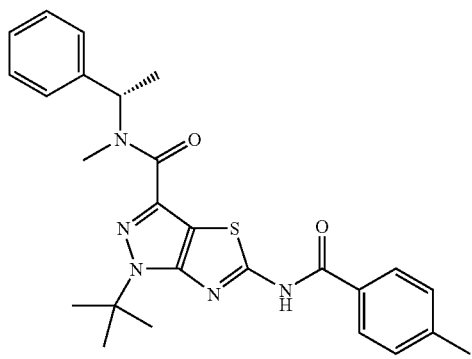
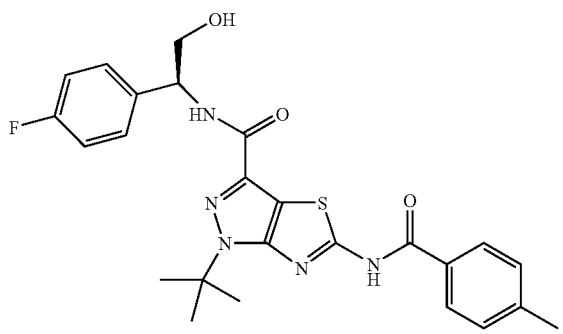
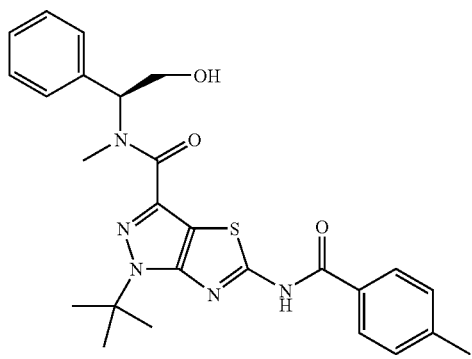
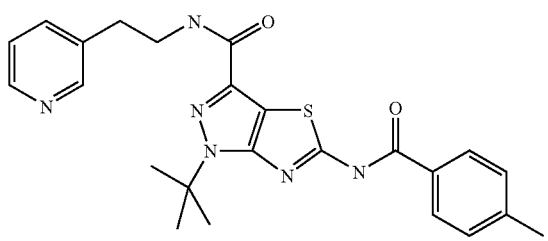

TABLE 2-continued
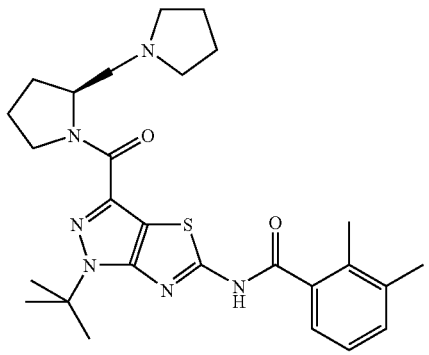
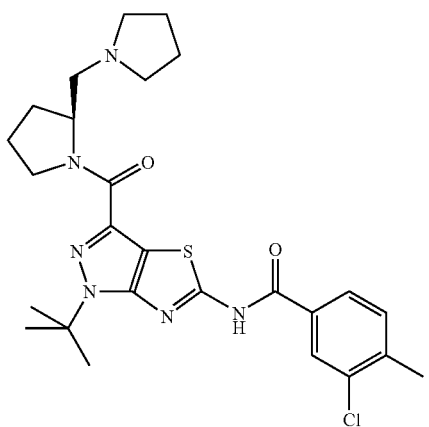
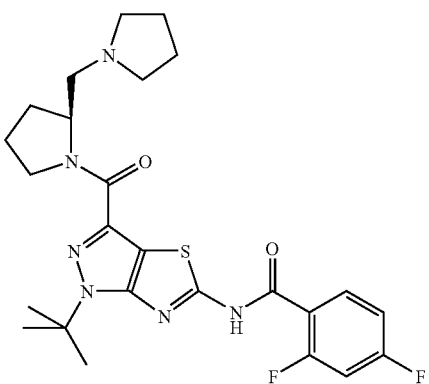
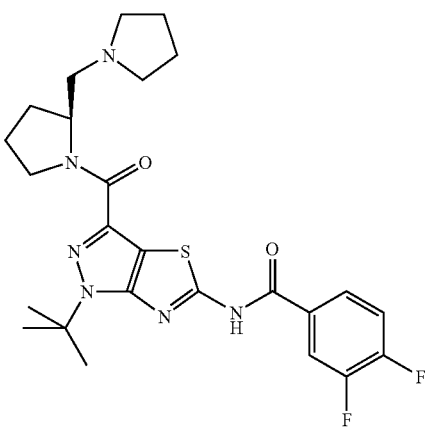

TABLE 2-continued
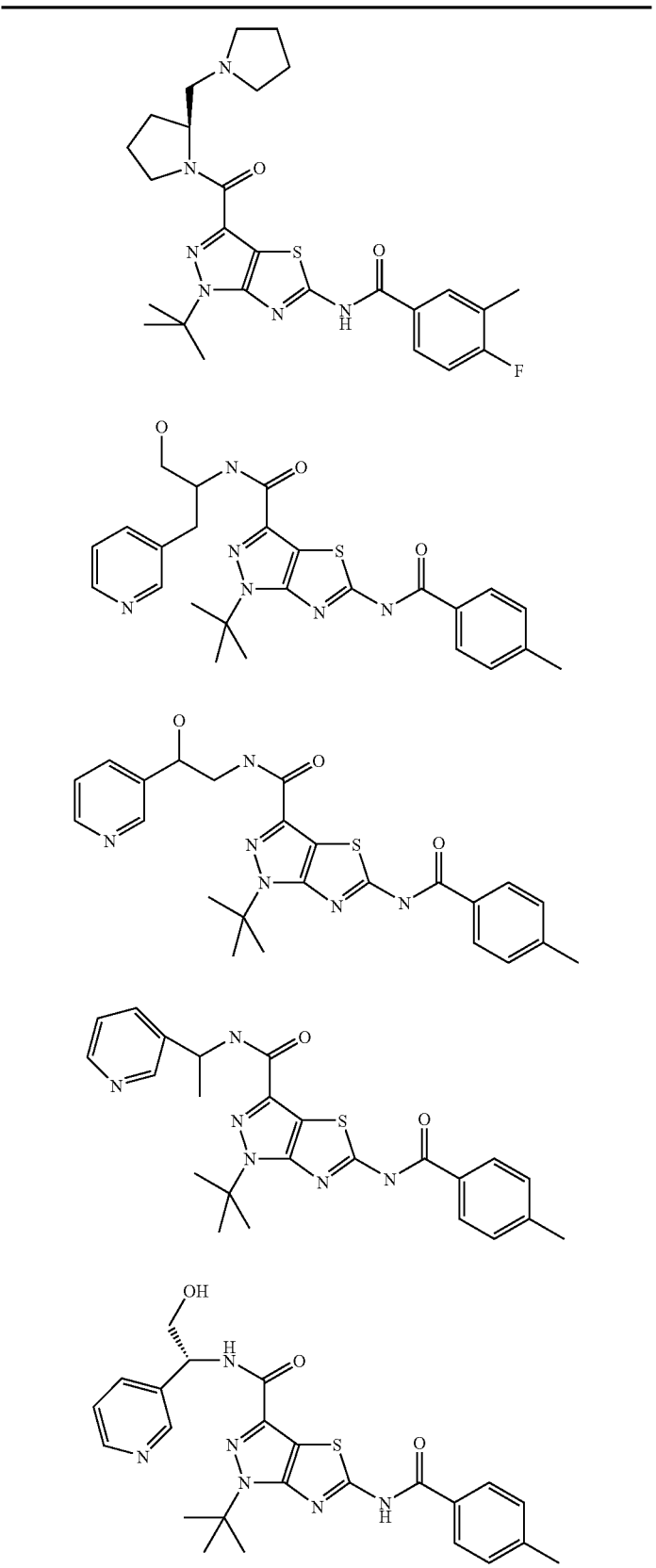

TABLE 2-continued
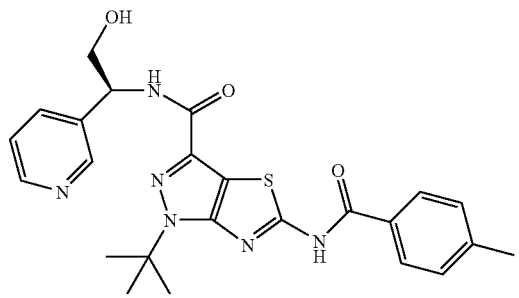
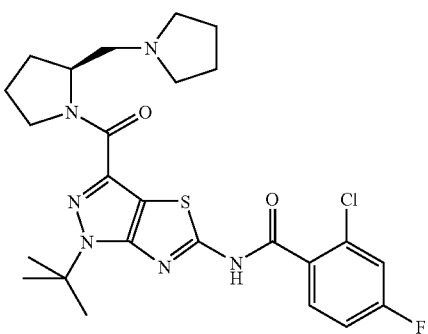
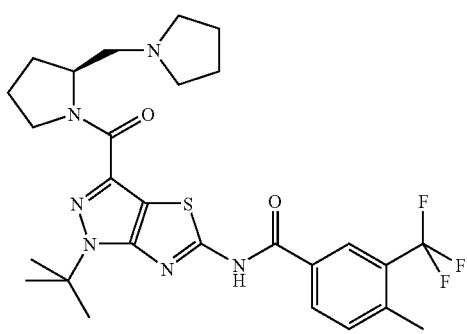
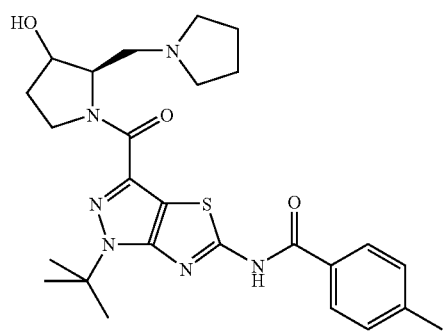

TABLE 2-continued
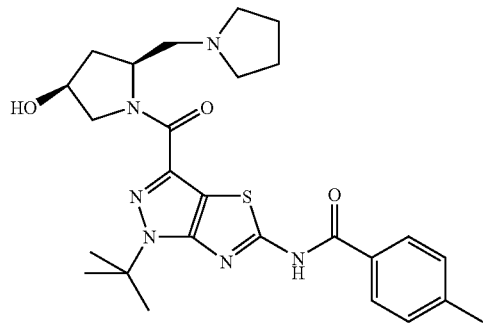
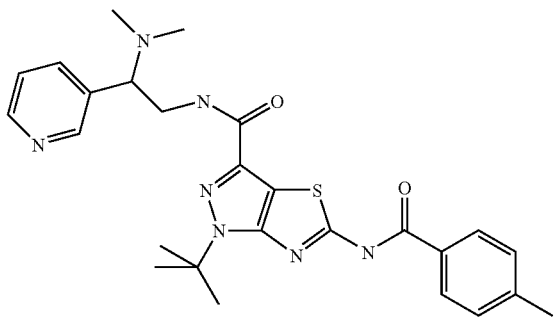
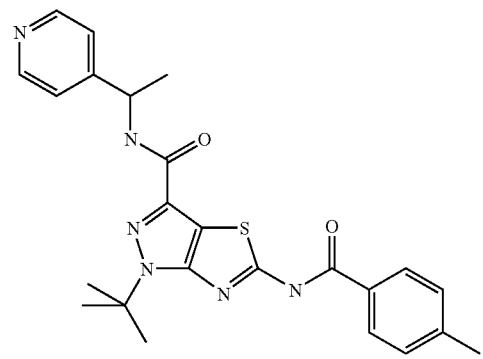
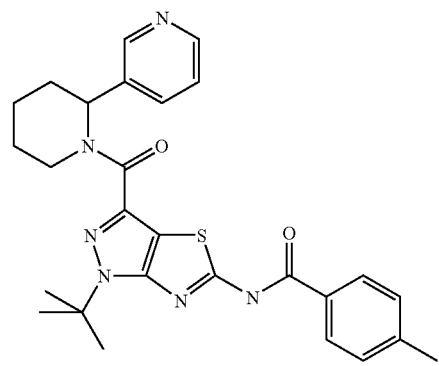
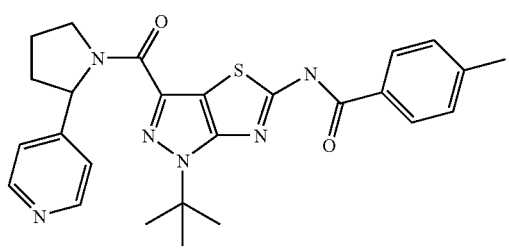

TABLE 2-continued
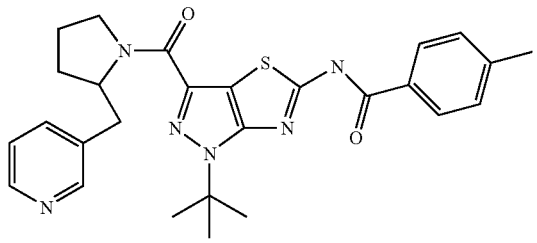
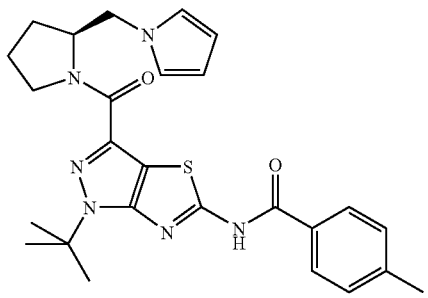
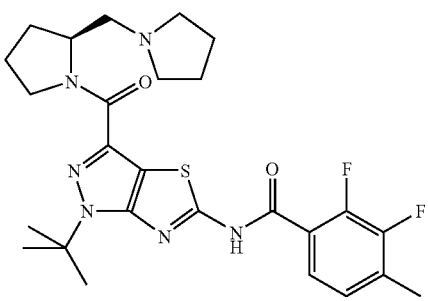
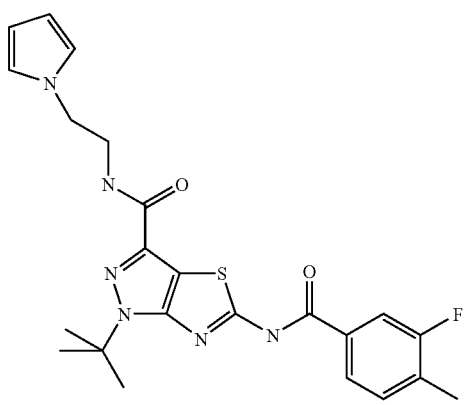
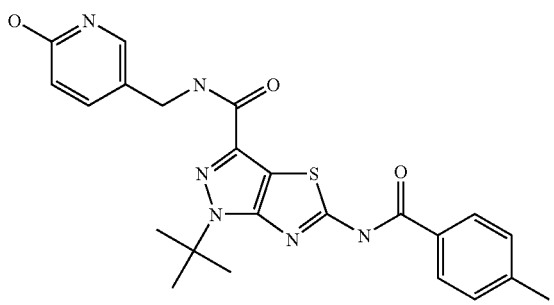

TABLE 2-continued
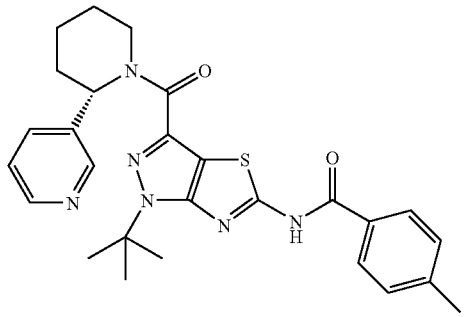
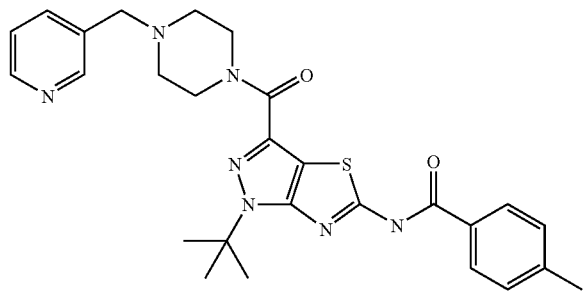
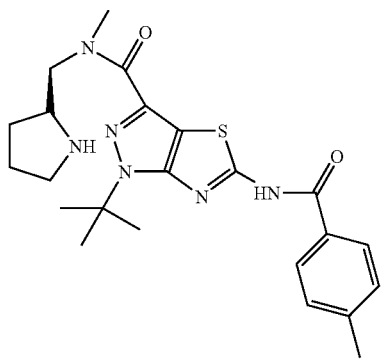
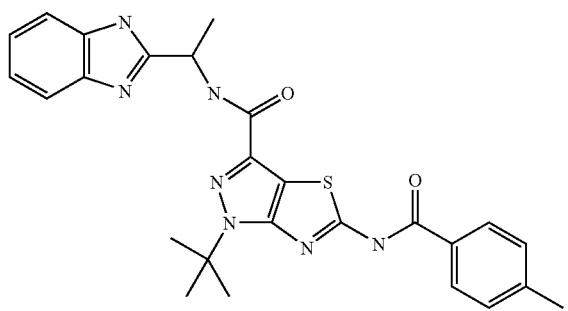
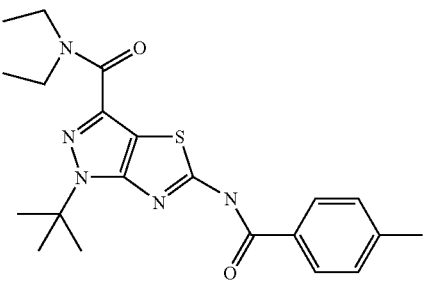

TABLE 2-continued
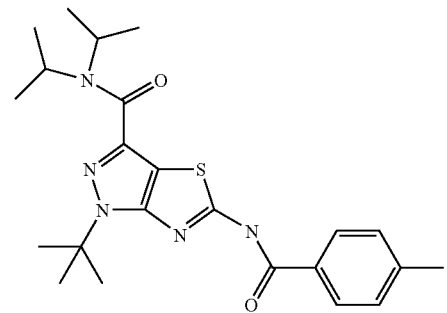
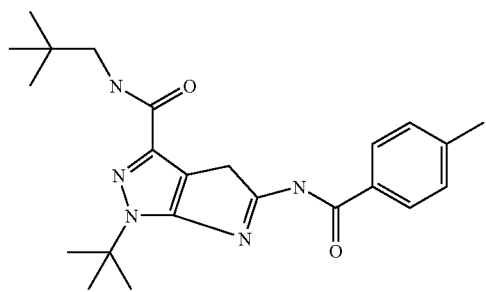
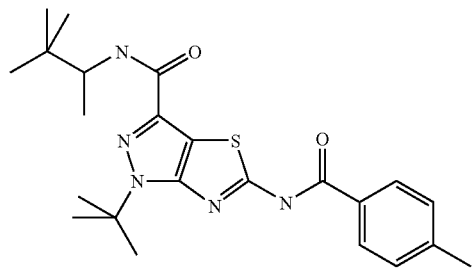
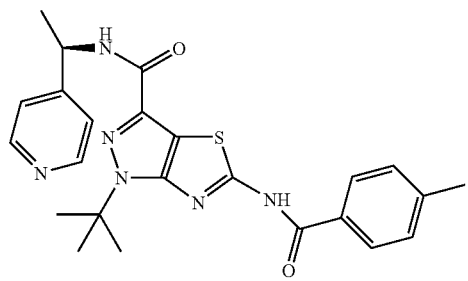
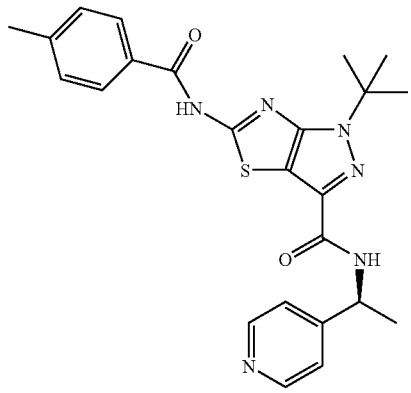

TABLE 2-continued
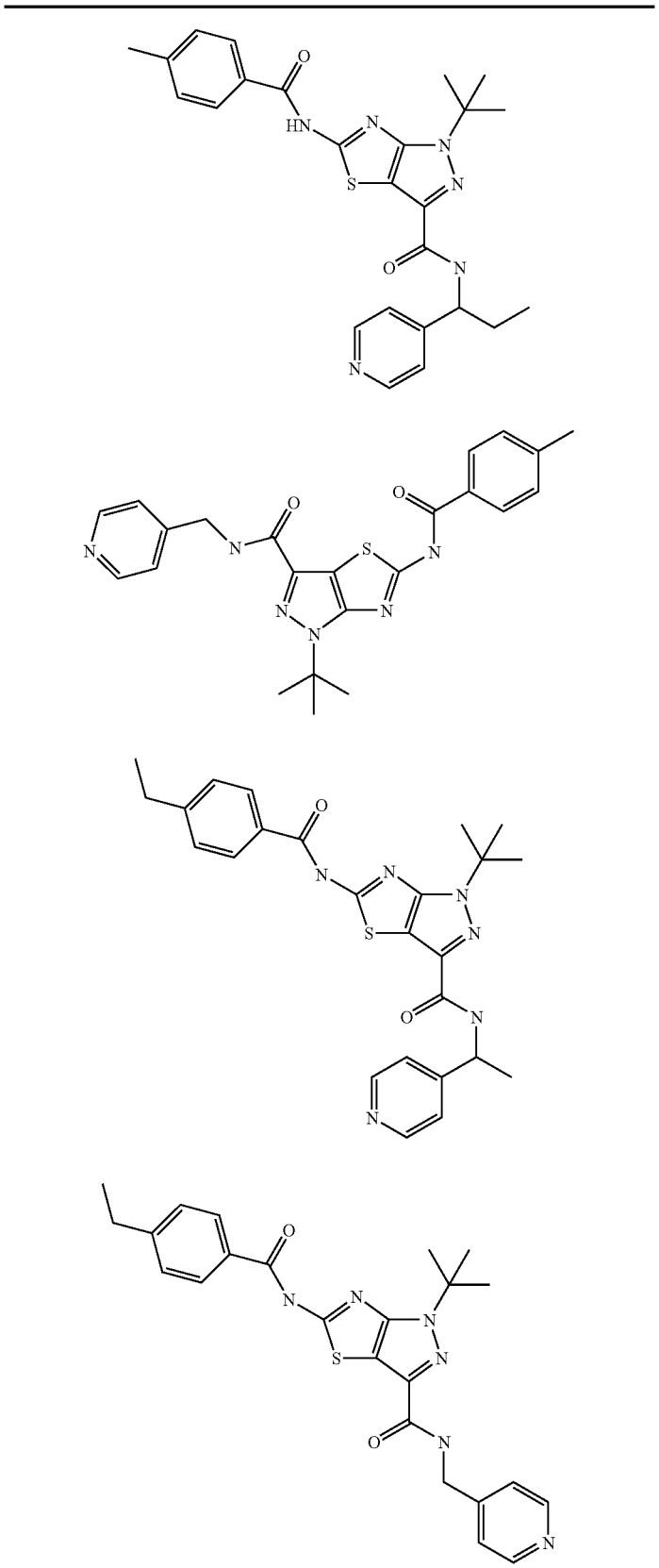

TABLE 2-continued

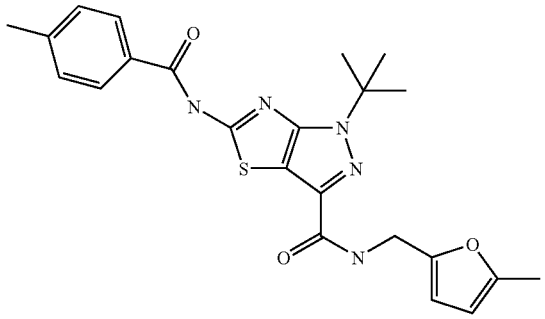

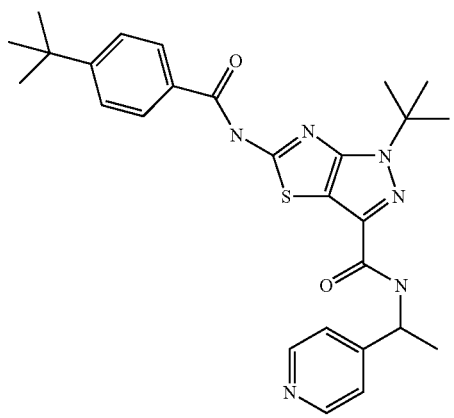

This invention also encompasses compounds of formula (3):

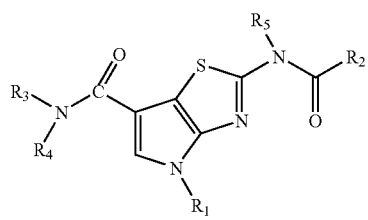

(3)

wherein:

$R_1$, $R_3$ and $R_4$ are each independently H, optionally substituted alkyl, optionally substituted alkenyl, optionally substituted alkynyl, optionally substituted aryl, optionally substituted heteroaryl, optionally substituted heterocycloalkyl, optionally substituted heterocycle, optionally substituted arylalkyl, optionally substituted heterocycloalkylalkyl, optionally substituted heteroarylalkyl, optionally substituted alkoxycarbonyl, optionally substituted aminocarbonyl, optionally substituted carbonyl, or optionally substituted sulfonyl; or $R_3$ and $R_4$, with the nitrogen to which they are attached, form an optionally substituted heterocycle;

$R_2$ is H, optionally substituted alkyl, optionally substituted alkenyl, optionally substituted alkynyl, optionally substituted aryl, optionally substituted heteroaryl, optionally substituted heterocycloalkyl, optionally substituted heterocycle, optionally substituted arylalkyl, optionally substituted heterocycloalkylalkyl, or optionally substituted heteroarylalkyl;

$R_5$ is H, alkyl, heteroalkyl, heterocycloalkyl, alkyl or aryl carbonyl, or optionally substituted alkyl or aryl sulfonyl;

and pharmaceutically acceptable salts, solvates, stereoisomers and prodrugs thereof.

In one specific embodiment, $R_1$ is branched alkyl (e.g., t-butyl).

In another embodiment, $R_2$ is optionally substituted aryl (e.g., optionally substituted phenyl).

In another embodiment, $R_1$ is t-butyl, and $R_2$ is p-methylphenyl.

In another embodiment, $R_3$ is H, and $R_4$ is optionally substituted alkyl (e.g., optionally substituted branched alkyl).

In another embodiment, $R_3$ is H, and $R_4$ is straight or branched alkyl, substituted with heteroaryl, heterocycle, or alkoxy.

Specific examples include, but are not limited to, the compounds listed in Table 3, and pharmaceutically acceptable salts, solvates, stereoisomers, racemic mixtures, stereomerically enriched mixtures, and prodrugs thereof:

TABLE 3
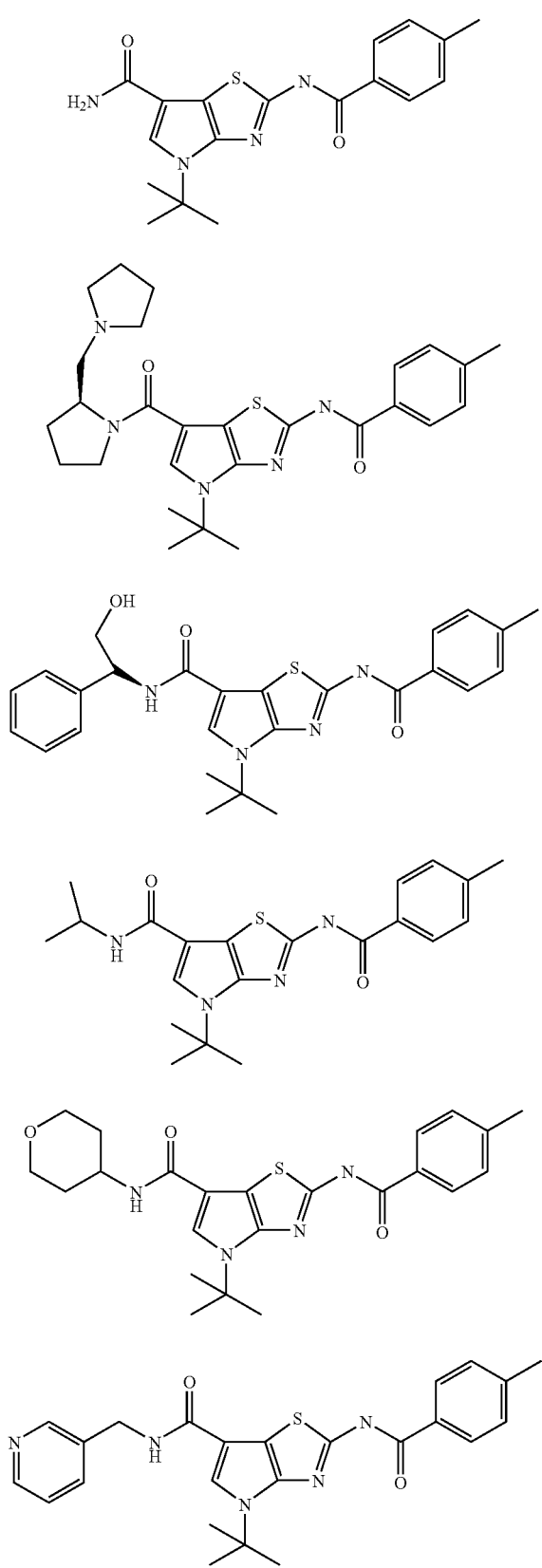
TABLE 3-continued
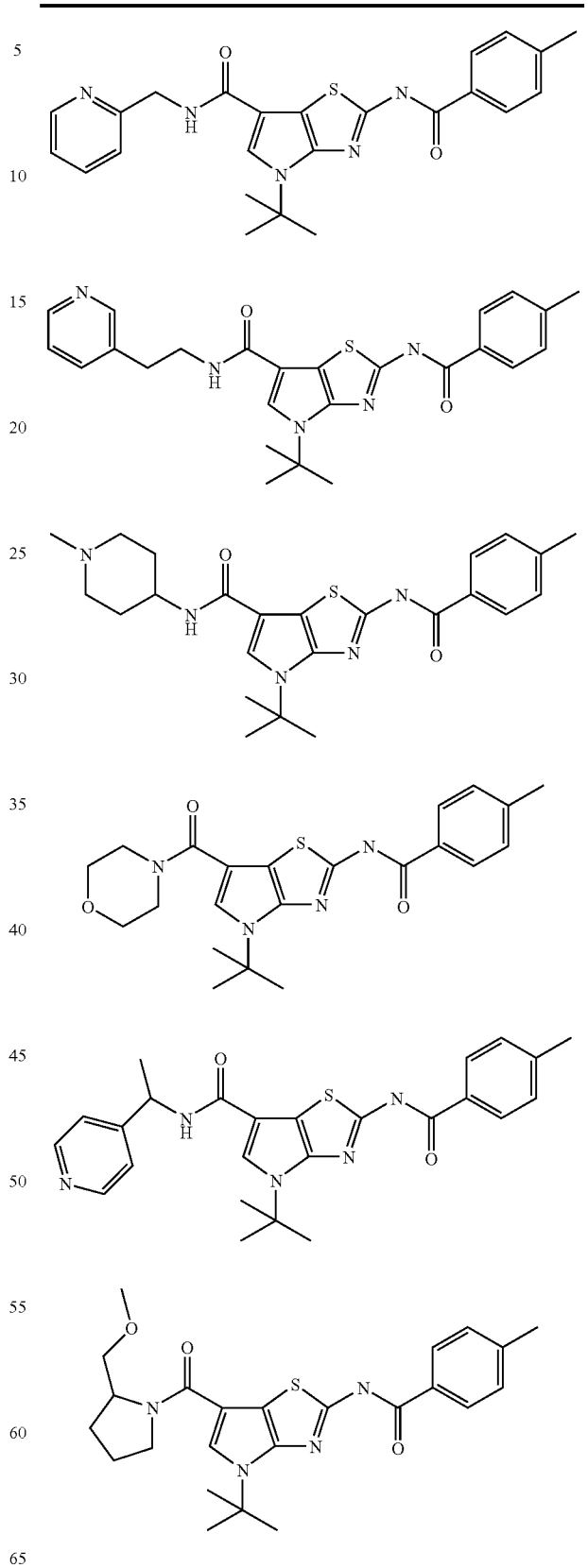

TABLE 3-continued
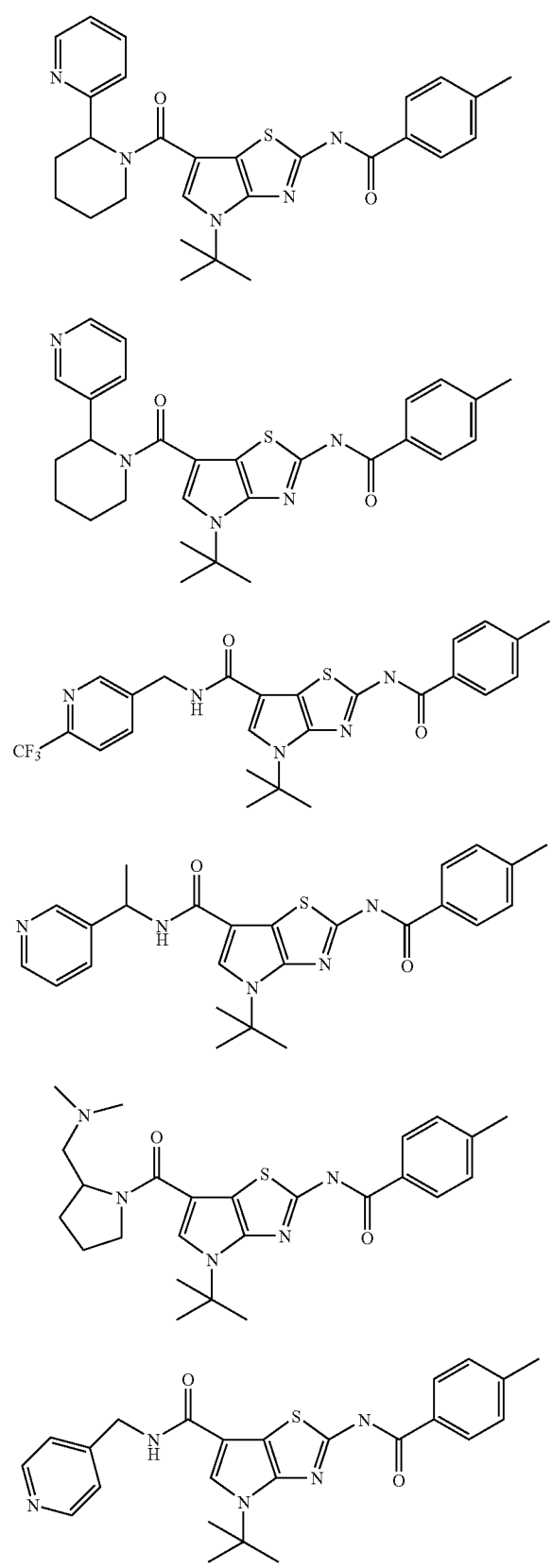
TABLE 3-continued
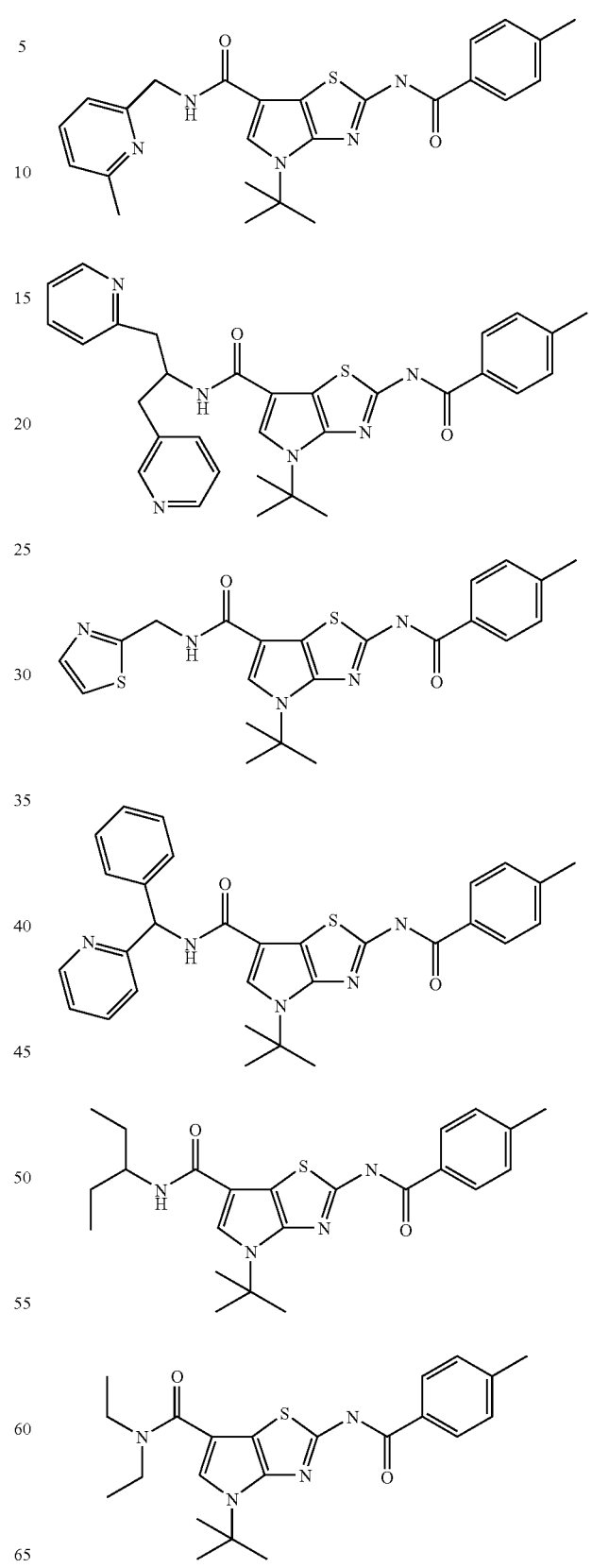

TABLE 3-continued
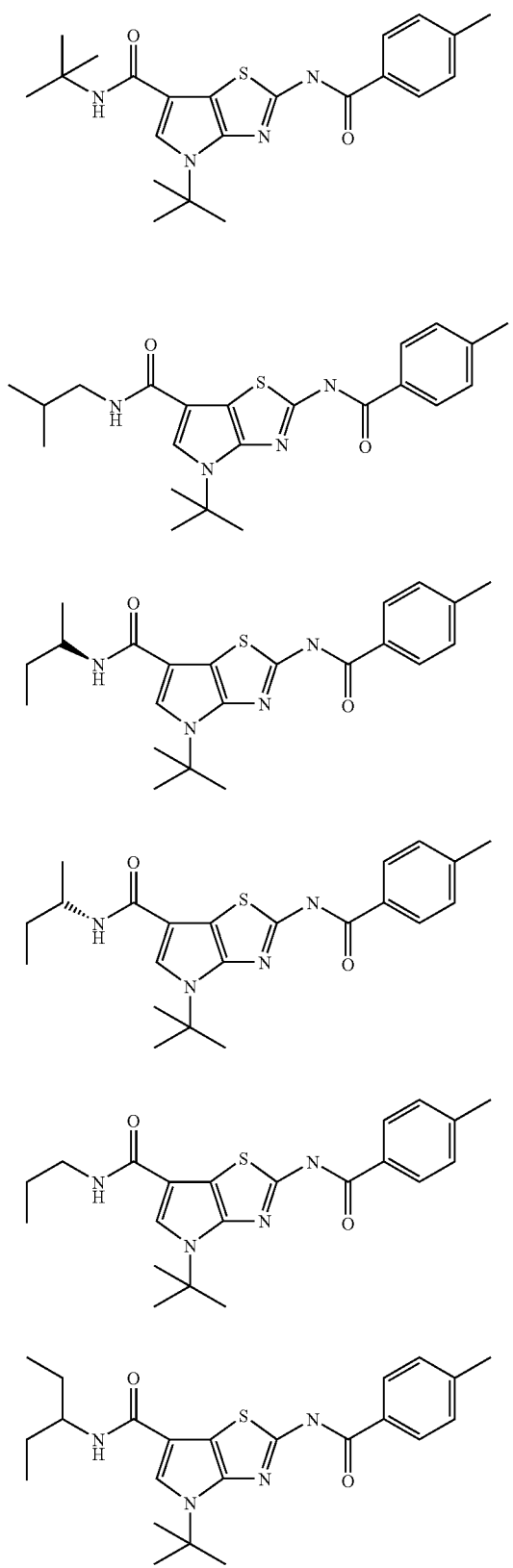
TABLE 3-continued
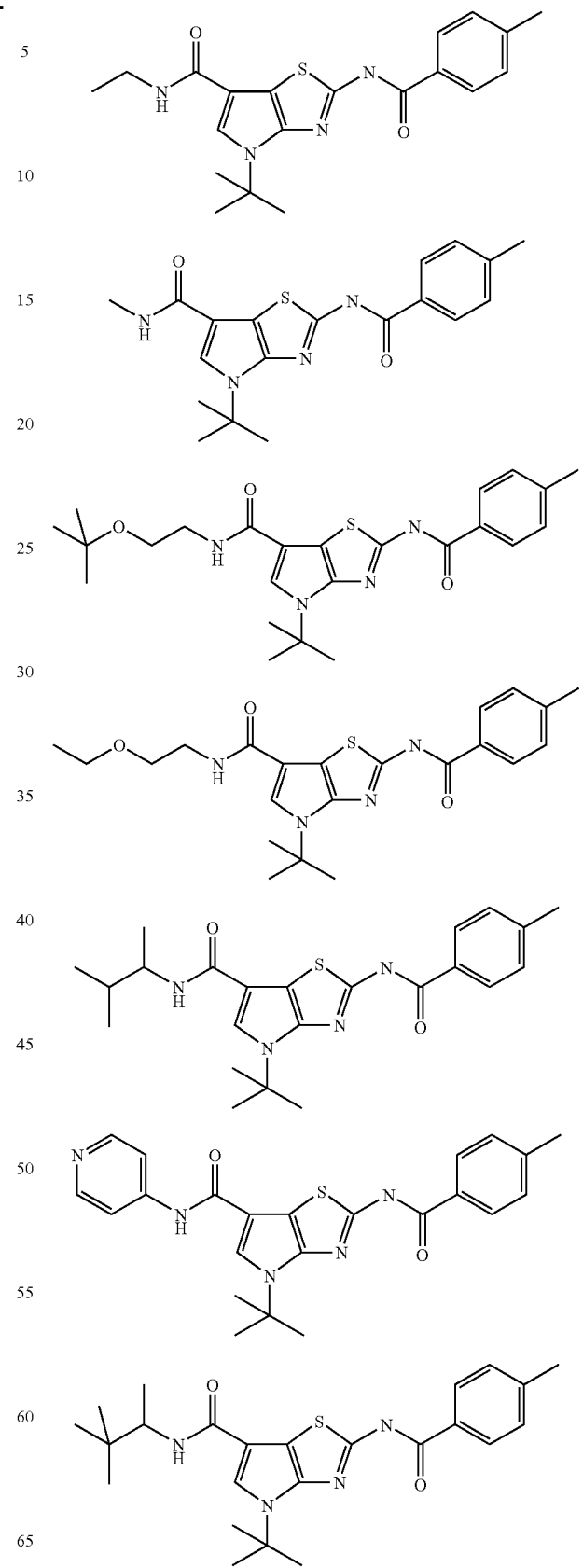

TABLE 3-continued

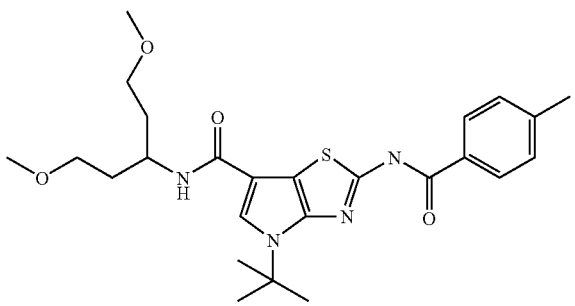

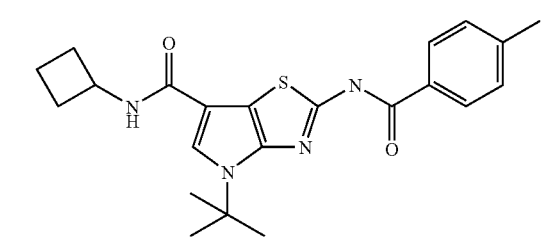

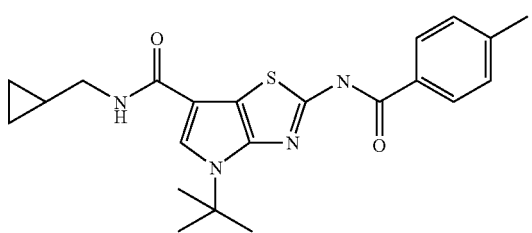

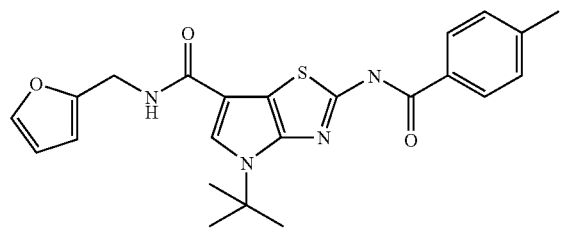

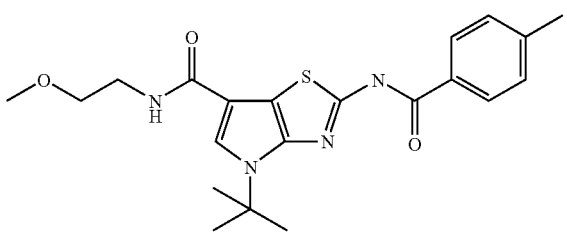

TABLE 3-continued

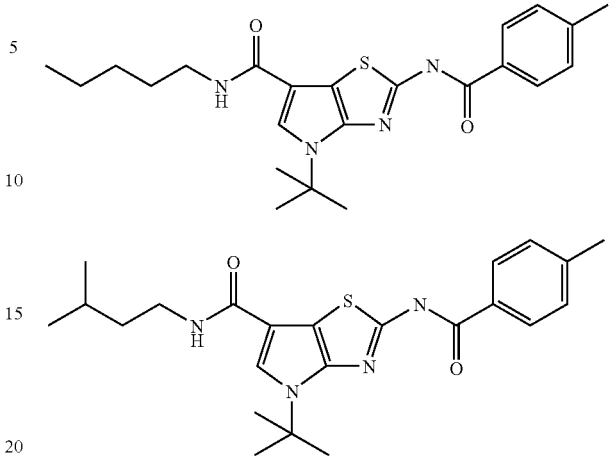

Various compounds of the invention may contain one or more stereocenters, and can exist as racemic mixtures of enantiomers or mixtures of diastereomers. This invention encompasses the use of stereomerically pure forms of such compounds, as well as the use of mixtures of those forms. For example, mixtures comprising equal or unequal amounts of the enantiomers of a particular compound of the invention may be used in methods and compositions of the invention. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions*, p. 268 (E. L. Eliel, Ed., Univ. of Notre Dame Press, Notre Dame, Ind., 1972).

Compounds of this invention may exist as amorphous or crystalline solids. Crystalline compounds of the invention may exist in one or more polymorphic forms, all of which are encompassed by this invention.

4.3 Preparation of Compounds of the Invention

Compounds of the invention can be prepared using methods known in the art, as well as methods described herein. For example, some compounds may be prepared as shown below:

Scheme 1

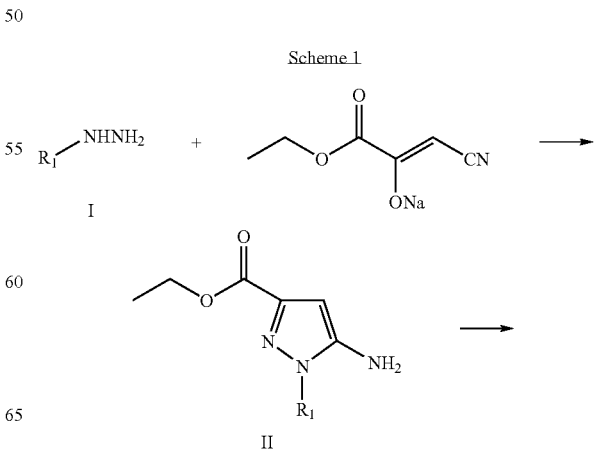

-continued

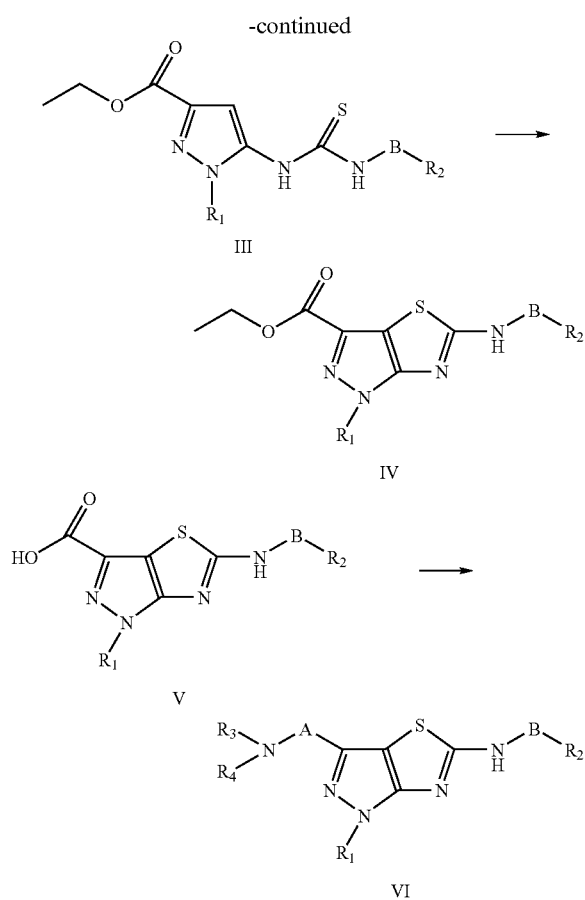

According to the method, the compounds of formula II, wherein $R_1$ is hydrogen, alkyl, aryl or heteroaryl, are prepared by reaction of compounds of formula I with sodium ethyl cyanopyruvate. A solution of a compound of formula I in water and one equivalent of acid, such as sulfuric acid, TFA, acetic acid or nitric acid, is added slowly to sodium ethyl cyanopyruvate solution in dry THF, toluene, methylene chloride or chloroform, preferably chloroform. The reaction is carried out at a temperature of about −10° C. to about 200° C., preferably at room temperature, for about 12 hours to 5 days. The resulting crude product is then dissolved in 1-butanol, ethanol, methanol or isopropanol in a sealed tube. The mixture is incubated at a temperature of about 25° C. to about 200° C., preferably about 10° C. to about 150° C., for about 12 to 48 hours. The crude product is then purified by $SiO_2$ column chromatography using hexanes and ethyl acetate mixture, or purified by recrystallization using mixtures of organic solvents, such as hexanes and ether.

Compounds of formula III may be prepared by reaction of a compound of formula II with thioisocyanate. Thioisocyanates are commercially available, or may be prepared by reaction of corresponding acid chlorides with potassium thiocyanate following the procedures disclosed in *Org. Syn.*, 28: 98 (1948) and *J. Am. Chem. Soc.*, 77: 5440 (1955). A solution of a compound of formula II in anhydrous THF, toluene, chloroform, methylene chloride, 1-butanol, ethanol or ether with one equivalent of thioisocyanate is incubated at a temperature of about 25° C. to about 200° C., preferably about 80° C. to about 150° C. In the cases where B is carbonyl, the preferable temperature is about 80° C. to about 100° C. In other cases where B is nothing, the preferred temperature is about 120° C. to about 150° C.

Compounds of formula IV may be prepared by reaction of a compound of formula III with a halogenating reagent, such as N-bromosuccinimide or N-iodosuccinimide in a solvent at a temperature of about 0° C. to about 150° C., preferably about 0° C. to about 60° C. Suitable solvents are organic solvents such as chloroform, methylene chloride, THF, acetonitrile, benzene, toluene or ether. The reaction is monitored by LCMS and/or TLC and typically takes about 1 to 12 hrs.

Compounds of formula V may be prepared by reaction of a compound of formula IV with a base in a solvent at a temperature of about 0° C. to about 100° C., conveniently at room temperature. Suitable bases include lithium hydroxide monohydrate, sodium hydroxide and potassium hydroxide. Suitable solvents are mixture of alkyl alcohol and water such as methanol and water, or the mixture of THF and water. After the completion of reaction, the pH of the mixture is adjusted to 5-6 by addition of an acid, such as sulfuric acid, TFA, acetic acid or hydrochloric acid. The product generally precipitates out and can be filtered off to give pure product.

Compounds of formula VI wherein A is carbonyl may be prepared by coupling reaction of a compound of formula V with an amine in an organic solvent at a temperature of about 0° C. to about 100° C., preferably at room temperature to about 50° C. Excess of a coupling reagent, such as N-cyclohexylcarbodiimide N'-methyl polystyrene (200-400 mesh, NovaBio, Catalog number: A28141, loading: 1.8 mmoles/g) is used as coupling reagent, and 1-hydroxy benzotriazole is used to activate the compound of formula V. Suitable solvents include chloroform, THF, acetonitrile, toluene, DMF and 1,4-dioxane. After the completion of the reaction, the excess of N-cyclohexylcarbodiimide N'-methyl polystyrene, 1-hydroxy benzotriazole and excess of compound of formula V are scavenged by addition of polystyrene-supported amine such as PS-Trisamine (Argonaut Technology Inc. Catalog number: 800230, loading: 4.11 mmoles/g) at a temperature of room temperature to about 100° C. The product is purified by $SiO_2$ column chromatography or preparative HPLC using methanol/$H_2O$/TFA as the solvent.

Preparation of compounds of formula VIA is shown below in Scheme 2. A compound of formula VIA may be prepared from a reaction of a compound of formula VI with alkyl halides, acid chlorides, sulfonyl chlorides in the presences of a base at a temperature of about 0-200° C. in an organic solvent such as DMF, 1,4-dioxane, THF, ethanol or methylene chloride.

Scheme 2

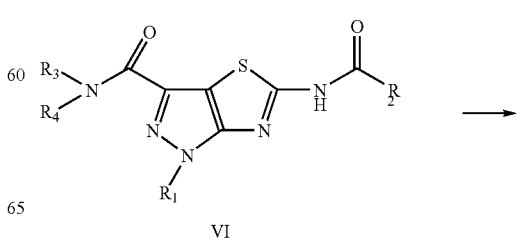

VI

-continued

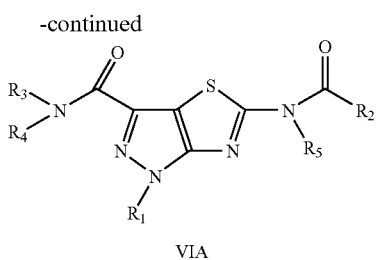

VIA

4.4 Pharmaceutical Compositions

This invention encompasses pharmaceutical compositions and dosage forms comprising compounds of the invention as their active ingredients. Pharmaceutical compositions and dosage forms of this invention may optionally contain one or more pharmaceutically acceptable carriers or excipients. Certain pharmaceutical compositions are single unit dosage forms suitable for oral, topical, mucosal (e.g., nasal, pulmonary, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, oral administration may require enteric coatings to protect the active ingredient from degradation within the gastrointestinal tract. In another example, the active ingredient may be administered in a liposomal formulation to shield it from degradative enzymes, facilitate transport in circulatory system, and/or effect delivery across cell membranes to intracellular sites.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

4.4.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants or lubricants can be used in pharmaceutical compositions and dosage forms of the invention.

The dosage forms of the invention may optionally comprise an enteric coating to provide release in parts other than gastrointestinal region. The enteric coating material may be used in addition to, or instead of, other suitable coating materials. Examples of suitable enteric polymers include, but are not limited to, cellulose acetate phthalate, hydroxypropylmethylcellulose phthalate, polyvinylacetate phthalate, methacrylic acid copolymer, shellac, hydroxypropylmethylcellulose succinate, cellulose acetate trimellitate, and mixtures thereof. Enteric coatings may be provided using any suitable methods known in the art, including, but not limited to, spray-application of enteric polymers over a sub-coat.

4.4.2 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; and water-miscible vehicles such as, but not limited to, ethyl alcohol, polyethylene glycol, and polypropylene glycol.

Compounds that increase the solubility of one or more of the active ingredients (i.e., the compounds of this invention) disclosed herein can also be incorporated into the parenteral dosage forms of the invention.

4.4.3 Transdermal, Topical and Mucosal Dosage Forms

Transdermal, topical, and mucosal dosage forms of the invention include, but are not limited to, ophthalmic solutions, sprays, aerosols, creams, lotions, ointments, gels, solutions, emulsions, suspensions, or other forms known to one of skill in the art. See, e.g., *Remington's Pharmaceutical Sciences*, 16th and 18th eds., Mack Publishing, Easton Pa. (1980 & 1990); and *Introduction to Pharmaceutical Dosage Forms*, 4th ed., Lea & Febiger, Philadelphia (1985). Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal, topical, and mucosal dosage forms encompassed by this invention are well known to those skilled in the pharmaceutical arts, and depend on the particular tissue to which a given pharmaceutical composition or dosage form will be applied.

Depending on the specific tissue to be treated, additional components may be used prior to, in conjunction with, or subsequent to treatment with active ingredients of the invention. For example, additional penetration enhancers can be used to assist in delivering the active ingredients to the tissue.

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, prodrugs, clathrates, hydrates or solvates of the active ingredients can be used to further adjust the properties of the resulting composition.

4.4.4 Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the compounds of this invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.4.5 Kits

In some cases, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit comprises a single unit dosage form of the compounds of this invention, or a pharmaceutically acceptable salt, prodrug, solvate, hydrate, or stereoisomer thereof, and a single unit dosage form of another agent that may be used in combination with the compounds of this invention. Kits of the invention can further comprise devices that are used to administer the active ingredients. Examples of such devices include, but are not limited to, syringes, drip bags, patches, and inhalers.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. However, in specific embodiments, the formulations of the invention do not contain any alcohols or other co-solvents, oils or proteins.

The invention is further defined by reference to the following non-limiting examples. It will be apparent to those skilled in the art that many modifications, both to materials and methods, can be practiced without departing from the spirit and scope of this invention.

4.5 Methods of Treatment, Prevention and Management

This invention encompasses methods of treating, preventing, and/or managing various diseases and disorders using the compounds described herein. Examples of diseases and disorders include, but are not limited to: allergic disorders (e.g., immunodeficiency diseases and hypersensitivity); cardiovascular disorders (e.g., hypertension and arteriosclerosis); dental and oral disorders (e.g., inflammation of the oral mucosa); dermatologic disorders (e.g., dermatitis and skin infections); disorders due to physical agents (e.g., altitude or motion sickness); endocrine and metabolic disorders (e.g., hypopituitarism and hyperthyroism); gastrointestinal disorders (e.g., inflammatory bowel disease and pancreatitis); gentourinary disorders (e.g., urinary incontinence and myoneurogenic disorders); gynecologic and obstetrics disorders (e.g., sexual dysfunction and gynecologic inflammations); hematological and oncologic disorders (e.g., anemias, myeloproliferative disorder and cancer); hepatic and biliary disorders (e.g., fatty liver and hepatitis); infectious diseases (e.g., diseases caused by bacterial, viral or fungal infections); musculoskeletal and connective tissue disorders (e.g., rheumatoid arthritis and systemic sclerosis); neurologic disorders (e.g., pain and sleep disorders); nutritional disorders (e.g., protein-energy malnutrition); ophthalmologic disorders (e.g., conjunctivitis and keratitis); psychiatric disorders (e.g., anxiety and mood disorders); and pulrmonary disorders (e.g., asthma and bronchitis). All of these disorders are well-known in the art. See, Merck Manual of Diagnosis and Therapy, $17^{th}$ Ed. (1999), which is incorporated herein by reference.

Doses of compounds of the invention vary depending on factors such as: specific indication to be treated, prevented, or managed; age and condition of a patient; and amount of second active agent used, if any. Generally, the compounds may be used in an amount of from about 0.01 mg to about 2000 mg per day, and can be adjusted in a conventional fashion (e.g., the same amount administered each day of the treatment, prevention or management period), in cycles (e.g., one week on, one week off), or in an amount that increases or decreases over the course of treatment, prevention, or management. In other embodiments, the dose can be from about 0.1 mg to about 1000 mg, from about 0.1 mg to about 500 mg, from about 0.1 mg to about 100 mg, from about 0.1 mg to about 50 mg, from about 0.1 mg to 10 mg, from about 1 mg to about 1000 mg, from about 1 mg to about 500 mg, from about 1 mg to about 100 mg, from about 1 mg to about 50 mg, from about 1 mg to about 10 mg, from about 10 mg to about 1000 mg, from about 10 mg to about 500 mg, from about 10 mg to 100 mg, from about 10 mg to 50 mg, from about 50 mg to about 500 mg, from about 50 mg to 200 mg, or from about 100 mg to 300 mg per day.

This invention also encompasses the use of compounds of the invention in combination with one or more second active agents. Second active agents can be large molecules (e.g., proteins) or small molecules (e.g., synthetic inorganic, organometallic, or organic molecules). Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetlyase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransrerase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); P13K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Specific second active compounds that can be combined with compounds of this invention vary depending on the specific indication to be treated, prevented or managed.

Administration of compounds of the invention, or pharmaceutically acceptable salts, solvates, stereoisomers, or prodrugs thereof, and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for compounds of this invention is oral. Preferred routes of administration for the second active agents or ingredients of the invention are known to those of ordinary skill in the art. See, e.g., Physicians'Desk Reference, 1755-1760 ($56^{th}$ ed., 2002).

In one embodiment of the invention, the second active agent is administered once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of compounds of the invention and any optional additional active agents concurrently administered to the patient.

5. EXAMPLES 5.1 Purification and Identification of Synthesized Compounds

The following procedures using High Performance Liquid Chromatography (HPLC) were performed to purify and identify following the syntheses of compounds of the invention.

Method A: Shimadzu HPLC YMC ODS-A 4.6×33 mm column, solvent A-MeOH/H$_2$O/TFA=10/90/0.1 by volume, solvent B-MeOH/H$_2$O/TFA=90/10/0.1 by volume, gradient 0-100% B in 4 minutes, detection at 220 nM, 3 ml/min flow rate;

Method B: Shimadzu HPLC YMC ODS-A 4.6×33 mm column, solvent A-MeOH/H$_2$O/TFA=10/90/0.1 by volume, solvent B-MeOH/H$_2$O/TFA=90/10/0.1 by volume, gradient 0-100% B in 6 minutes, detection at 220 nM, 2 ml/min flow rate;

Method C: Agilent Qc1.m, Polaris C18 5μ4.6×30 mm column, solvent A-methanol/water/TFA=10/90/0.1 by volume, solvent B-methanol/water/TFA=90/10/0.1 by volume, gradient 0-100% B in 2 minutes, 2.5 min run time, detection at 220 nM;

Method D: YMC Pack ODS-A 3.0×50 mm column, solvent A-MeOH/H$_2$O/TFA=10/90/0.1 by volume, solvent B-MeOH/H$_2$O/TFA=90/10/0.1 by volume, gradient 0-100% B in 4 min, detection at 220 rdM, 2 m/min flow rate;

5.2 5-Amino-1-phenyl-1H-pyrazole-3-carboxylic acid ethyl ester

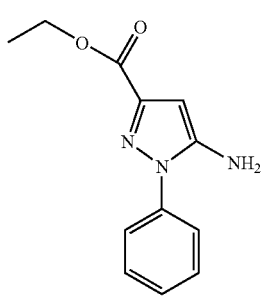

Phenyl hydrazine (2.94 ml, 0.03 moles) was dissolved in water (50 ml) in a 500 ml beaker. Concentrated $H_2SO_4$ (1.63 ml, 0.03 mole) was added drop-wise using a pipette while cooling with ice water bath. This phenyl hydrazine solution was then added to a stirred solution of sodium ethyl cyanopyruvate (5.37 g, 0.03 mole) in 70 ml of chloroform in a 500 ml round bottom flask at room temperature. Stirring was maintained for about 24 hrs and the reaction was monitored by LCMS. After the completion of reaction, the organic layer was separated and the aqueous layer was extracted with $CHCl_3$ (2×150 ml). The combined organic layer was then washed with saturated $NaHCO_3$ (1×100 ml), dried over sodium sulfate. Removal of solvent provided a viscous oil which was mainly non-cyclized hydrazone. The crude product was dissolved in minimum amount of dry EtOH (15 ml) and the mixture was heated in sealed tube at 120-150° C. for overnight. After the completion of reaction, ethanol was evaporated in vacuo to give crude product, which was purified by column chromatography eluting with Hexanes/Ethyl Acetate=9/1 to 1/1 to give 5.54 g of 5-Amino-1-phenyl-1H-pyrazole-3-carboxylic acid ethyl ester (yield: 80%).

Compounds shown in Table 4, which are encompasssed by the generic structure provided below, were prepared starting with the appropriate hydrazine and sodium ethyl cyanopyruvate, using similar procedures:

TABLE 4

| Structure | Analytical LC | MS |
|---|---|---|
| (pyrazole, R = H) | Method C RT = 0.47 min | M + 1 = 156 |
| (pyrazole, R = CH$_2$CF$_3$) | Method C RT = 1.12 min | M + 1 = 238 |
| (pyrazole, R = 4-methylphenyl) | Method C RT = 1.43 min | M + 1 = 246 |
| (pyrazole, R = CH$_3$) | Method C RT = 0.65 min. | M + 1 = 170 |
| (pyrazole, R = cyclohexyl) | Method C RT = 1.09 min. | M + 1 = 238 |
| (pyrazole, R = 2-chlorophenyl) | Method C RT = 1.26 min. | M + 1 = 266 |

TABLE 4-continued

[Structure with R group on pyrazole-carboxylate core]

| Structure | Analytical LC | MS |
|---|---|---|
| [ethyl 5-amino-1-tert-butyl-pyrazole-3-carboxylate] | Method C RT = 1.16 min. | M + 1 = 212 |
| [ethyl 5-amino-1-(4-sulfamoylphenyl)-pyrazole-3-carboxylate] | Method C RT = 1.05 min. | M + 1 = 311 |
| [ethyl 5-amino-1-benzyl-pyrazole-3-carboxylate] | Method C RT = 1.36 min. | M + 1 = 246 |
| [ethyl 5-amino-1-(pyridin-2-yl)-pyrazole-3-carboxylate] | Method C RT = 1.50 min. | M + 1 = 233 |

TABLE 4-continued

[Structure with R group on pyrazole-carboxylate core]

| Structure | Analytical LC | MS |
|---|---|---|
| [ethyl 5-amino-1-(4-trifluoromethylphenyl)-pyrazole-3-carboxylate] | Method C RT = 1.77 min. | M + 1 = 300 |
| [ethyl 5-amino-1-(2-trifluoromethylphenyl)-pyrazole-3-carboxylate] | Method C RT = 1.44 min. | M + 1 = 300 |
| [ethyl 5-amino-1-(3,4-dimethylphenyl)-pyrazole-3-carboxylate] | Method C RT = 1.68 min. | M + 1 = 260 |
| [ethyl 5-amino-1-(4-methoxyphenyl)-pyrazole-3-carboxylate] | Method C RT = 1.48 min. | M + 1 = 262 |

TABLE 4-continued

[Structure with R group: ethyl pyrazole-3-carboxylate with 5-NH₂ and N1-R]

| Structure | Analytical LC | MS |
|---|---|---|
| [ethyl 5-amino-1-(4-nitrophenyl)-1H-pyrazole-3-carboxylate] | Method C RT = 1.34 min | M + 1 = 277 |
| [ethyl 5-amino-1-(4-cyanophenyl)-1H-pyrazole-3-carboxylate] | Method C RT = 1.26 min. | M + 1 = 257 |
| [ethyl 5-amino-1-(4-carboxyphenyl)-1H-pyrazole-3-carboxylate] | Method C RT = 1.25 min | M + 1 = 276 |

5.3  1-Phenyl-5-[3-benzoyl-thioureido]-1H-pyrazole-3-carboxylic acid ethyl ester

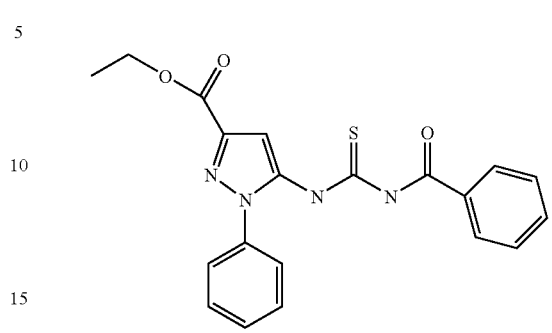

5-Amino-1-phenyl-1H-pyrazole-3-carboxylic acid ethyl ester (0.63 g, 2.72 mmoles) was dissolved in 10 ml of anhydrous tetrahydrofuran. Then, 442 mg of benzoyl thio-isocyante (2.72 mmoles) was added. The mixture was heated at 90° C. for 2 hours and the reaction was monitored by LCMS. After the completion of reaction, the THF was removed in vacuo to give 1.02 g of desired product (yield: 96%), which was dried under high vacuum. The product was used for the next step without further purification.

5.4  5-Benzoylamino-1-phenyl-1H-pyrazolo[3,4-d]thiazole-3-carboxylic acid ethyl ester

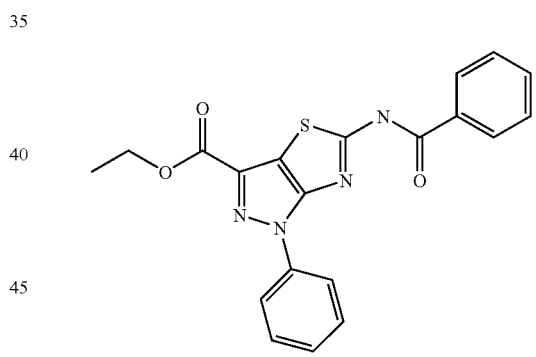

1-Phenyl-5-[3-benzoyl-thioureido]-1H-pyrazole-3-carboxylic acid ethyl ester (500 mg, 1.26 mmol) was dissolved in 25 ml anhydrous CHCl₃. N-Bromosuccinimide (225 mg, 1.26 mmol) was added portion wise in 5-10 minutes at 0° C. The reaction mixture was stirred at room temperature for 2 hours. After the completion of reaction, 100 ml of CHCl₃ was added to the reaction flask and the organic layer was washed with NaHCO₃ (2×30 ml), followed by brine, and dried over Na₂SO₄. Removal of the solvent gave product, which was sufficiently pure (>95%) for use in the following step. The crude product was further purified by SiO₂ column to give 450 mg of title compound (Yield: 91%).

The following compounds listed in Table 5, which are encompassed by the generic structure provided below, were prepared using the procedures described in Examples 5.3-5.4:

TABLE 5

| Structure | LC | MS |
|---|---|---|
| (ethyl ester pyrazolo-thiazole with N-(3-chlorobenzoyl), N1-cyclohexyl) | Method C RT = 1.91 min | M + 1 = 433 |
| (ethyl ester pyrazolo-thiazole with N-acetyl, N1-cyclohexyl) | Method C RT = 1.41 min | M + 1 = 337 |
| (ethyl ester pyrazolo-thiazole with N-acetyl, N1-CH2CF3) | Method C RT = 1.23 min | M + 1 = 337 |
| (ethyl ester pyrazolo-thiazole with N-(cyclohexanecarbonyl), N1-(4-fluorophenyl)) | Method C RT = 1.92 min | M + 1 = 417 |
| (ethyl ester pyrazolo-thiazole with N-acetyl, N1-methyl) | Method C RT = 0.95 min | M + 1 = 271 |

TABLE 5-continued
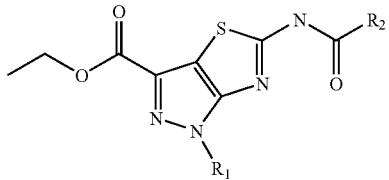
| Structure | LC | MS |
|---|---|---|
| 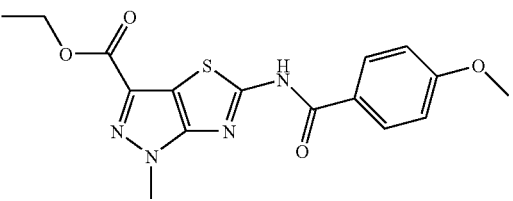 | Method C<br>RT = 1.37 min | M + 1 = 363 |
| 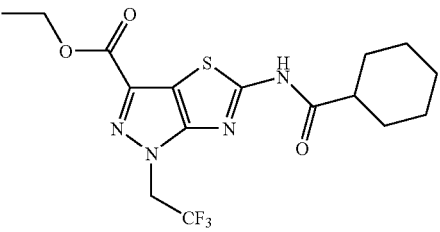 | Method C<br>RT = 1.69 min | M + 1 = 405 |
| 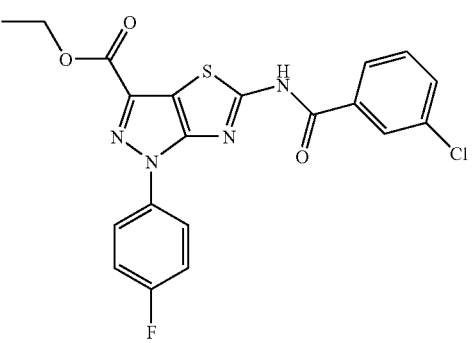 | Method C<br>RT = 1.99 min | M + 1 = 445 |
| 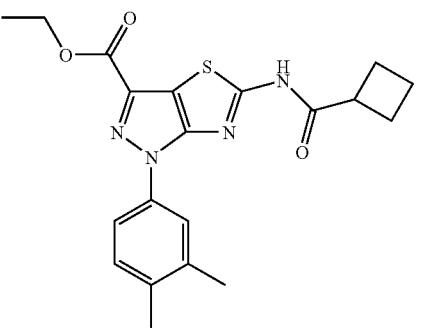 | Method C<br>RT = 1.89 min | M + 1 = 399 |

TABLE 5-continued

[Structure of ethyl pyrazolo-thiazole core with R1 on pyrazole N and NHC(O)R2 on thiazole]

| Structure | LC | MS |
|---|---|---|
| [ethyl ester pyrazolo-thiazole with cyclobutyl amide and 4-fluorophenyl N-substituent] | Method C<br>RT = 1.75 min | M + 1 = 389 |
| [ethyl ester pyrazolo-thiazole with 4-methoxybenzamide and 2-pyridyl N-substituent] | Method C<br>RT = 1.55 min | M + 1 = 424 |
| [ethyl ester pyrazolo-thiazole with 2-furoyl amide and benzyl N-substituent] | Method C<br>RT = 1.48 min | M + 1 = 399 |
| [ethyl ester pyrazolo-thiazole with 4-methylbenzamide and benzyl N-substituent] | Method C<br>RT = 1.73 min | M + 1 = 421 |

TABLE 5-continued

| Structure | LC | MS |
|---|---|---|
| (ethyl 5-(furan-2-carboxamido)-1-(4-methoxyphenyl)-1H-pyrazolo[3,4-d]thiazole-3-carboxylate) | Method C RT = 1.62 min | M + 1 = 413 |
| (ethyl 5-(cyclohexanecarboxamido)-1-(4-methoxyphenyl)-1H-pyrazolo[3,4-d]thiazole-3-carboxylate) | Method C RT = 1.87 min | M + 1 = 429 |
| (ethyl 1-(3,4-dimethylphenyl)-5-(4-methylbenzamido)-1H-pyrazolo[3,4-d]thiazole-3-carboxylate) | Method C RT = 1.77 min | M + 1 = 387 |
| (ethyl 5-(3-chlorobenzamido)-1-phenyl-1H-pyrazolo[3,4-d]thiazole-3-carboxylate) | Method C RT = 1.95 min | M + 1 = 427 |

TABLE 5-continued
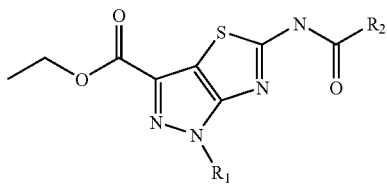
| Structure | LC | MS |
|---|---|---|
| 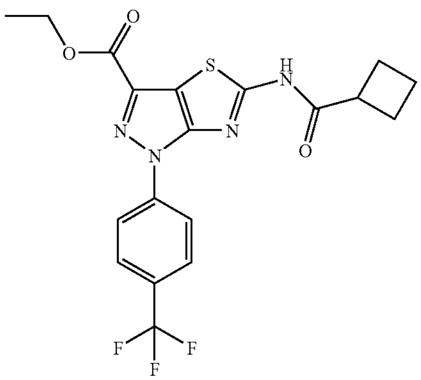 | Method C<br>RT = 1.91 min | M + 1 = 439 |
| 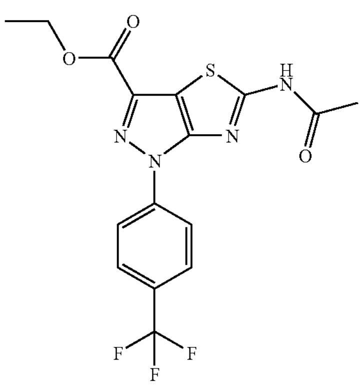 | Method C<br>RT = 1.68 min | M + 1 = 399 |
| 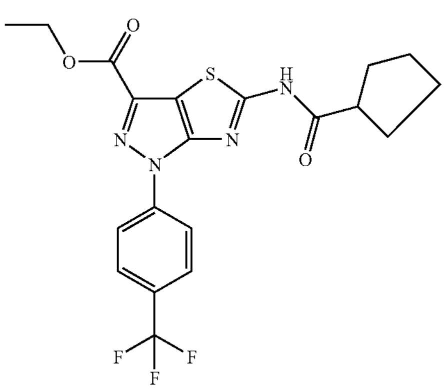 | Method C<br>RT = 1.97 min | M + 1 = 453 |

TABLE 5-continued

| Structure | LC | MS |
|---|---|---|
| (ethyl pyrazolo-thiazole carboxylate with cyclopropanecarboxamide, N-(4-trifluoromethylphenyl)) | Method C RT = 1.83 min | M + 1 = 425 |
| (ethyl pyrazolo-thiazole carboxylate with 3-chlorobenzamide, N-tert-butyl) | Method C RT = 1.85 min | M + 1 = 407 |
| (ethyl pyrazolo-thiazole carboxylate with 4-methylbenzamide, N-(4-methoxyphenyl)) | Method C RT = 1.88 min | M + 1 = 437 |
| (ethyl pyrazolo-thiazole carboxylate with 3-chlorobenzamide, N-benzyl) | Method C RT = 1.81 min | M + 1 = 441 |

5.5 5-Benzoylamino-1-phenyl-1H-pyrazolo[3,4-d]thiazole-3-carboxylic acid

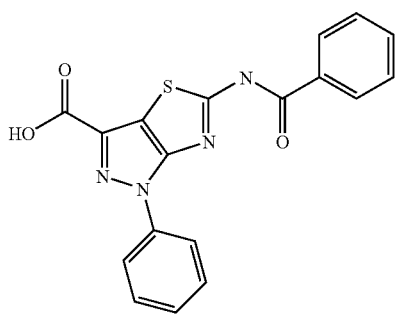

A mixture of 5-benzoylamino-1-phenyl-1H-pyrazolo[3,4-d]thiazole-3-carboxylic acid (230 mg, 0.58 mmol) and lithium hydroxide monohydrate (73 mg, 1.75 mmol) in 8 ml of MeOH: $H_2O$ (3:1) was stirred at room temperature for overnight. After the completion of reaction (monitored by LCMS), methanol was removed and the reaction mixture was neutralized with 1N HCl to pH=5-6 while cooling by ice bath. The product precipitates out as white solid. The solid was then filtered and washed with cold methanol, and was dried over $P_2O_5$ under high vacuum to provide 196 mg of title compound (yield: 92%).

The compounds listed in Table 6, which are encompassed by the generic structure provided below, were prepared using a similar procedure:

TABLE 6

| Structure | LC | MS |
|---|---|---|
| 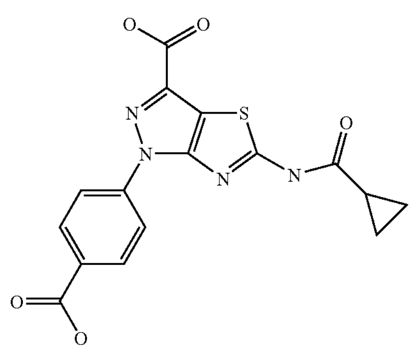 | Method C<br>RT = 1.737 min | M + 1 = 373 |
| 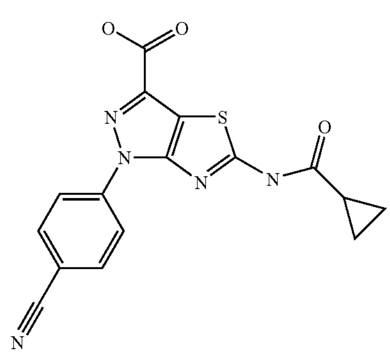 | Method C<br>RT = 1.708 min | M + 1 = 354 |

TABLE 6-continued

[Core structure: HO-C(=O)-pyrazolo-thiazole-NH-C(=O)-R₂, with R₁ on pyrazole N]

| Structure | LC | MS |
|---|---|---|
| 1-(4-nitrophenyl), R₂ = cyclopropyl | Method C RT = 1.813 min | M + 1 = 374 |
| 1-(3-chlorophenyl), R₂ = cyclopropyl | Method C RT = 1.884 min | M + 1 = 363 |
| 1-tert-butyl, R₂ = 4-methylphenyl | Method B RT = 3.540 min | M + 1 = 359 |
| 1-(2,5-dichlorophenyl), R₂ = cyclopropyl | Method C RT = 1.675 min | M + 1 = 397 |

TABLE 6-continued
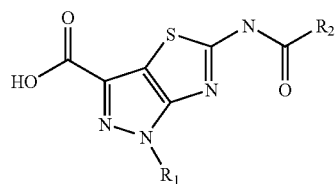
| Structure | LC | MS |
|---|---|---|
| 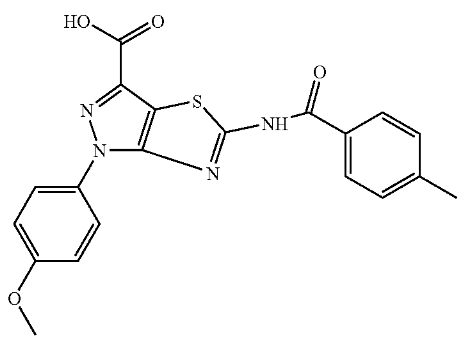 | Method C<br>RT = 2.24 min | M + 1 = 409 |
| 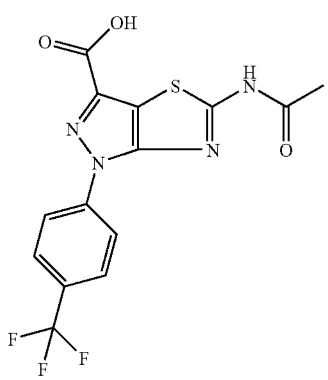 | Method C<br>RT = 2.07 min | M + 1 = 371 |
| 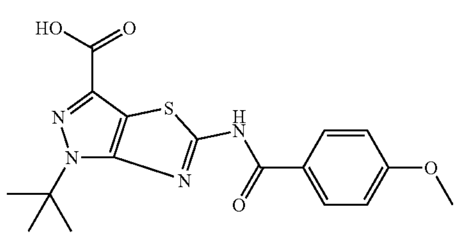 | Method C<br>RT = 2.0 min | M + 1 = 375 |
| 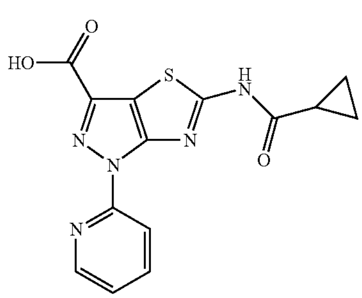 | Method C<br>RT = 1.71 min | M + 1 = 330 |

TABLE 6-continued
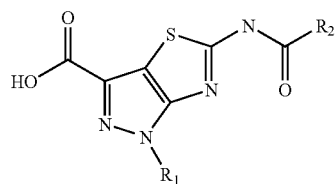
| Structure | LC | MS |
|---|---|---|
| | Method C<br>RT = 2.33 min | M + 1 = 399 |
| | Method C<br>RT = 2.30 min | M + 1 = 425 |
| | Method C<br>RT = 2.33 min | M + 1 = 371 |
| | Method C<br>RT = 2.1 min | M + 1 = 385 |

TABLE 6-continued
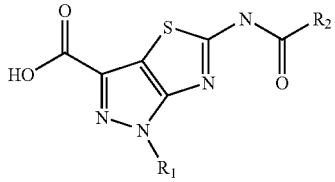
| Structure | LC | MS |
|---|---|---|
| 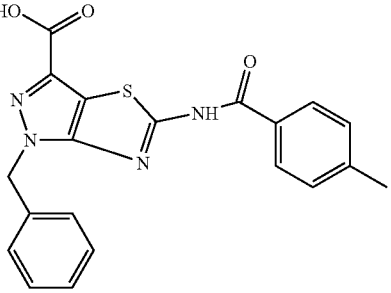 | Method C<br>RT = 2.24 min | M + 1 = 393 |
| 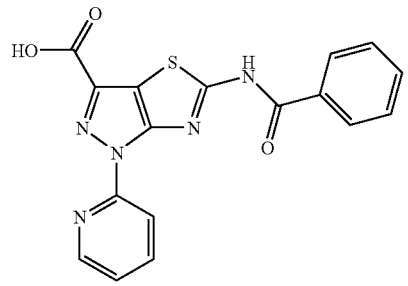 | Method C<br>RT = 1.98 min | M + 1 = 366 |
| 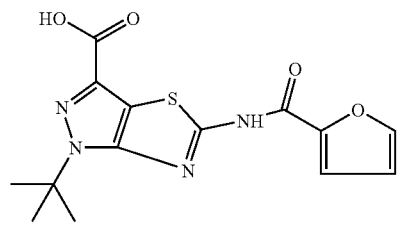 | Method C<br>RT = 1.84 min | M + 1 = 335 |
| 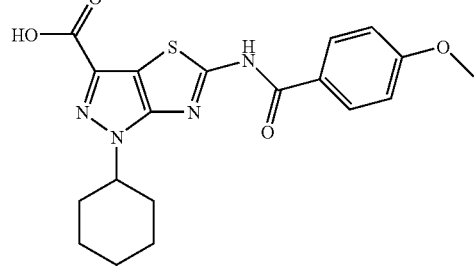 | Method C<br>RT = 2.2 min | M + 1 = 401 |
| 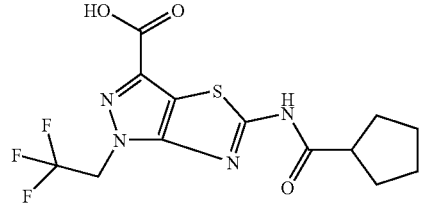 | Method C<br>RT = 1.88 min | M + 1 = 363 |

TABLE 6-continued
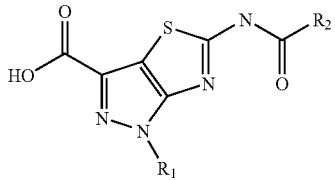
| Structure | LC | MS |
|---|---|---|
| 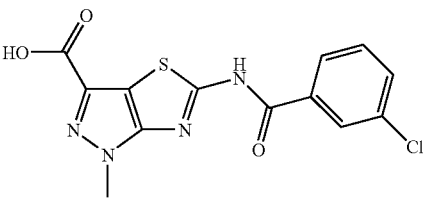 | Method C RT = 1.98 min | M + 1 = 337 |
| 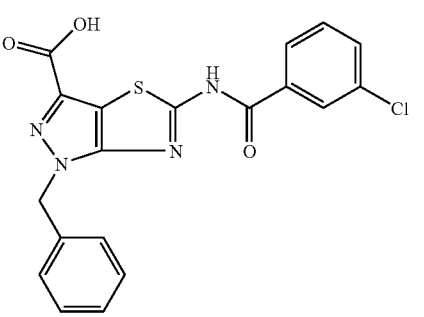 | Method C RT = 2.36 min | M + 1 = 413 |
| 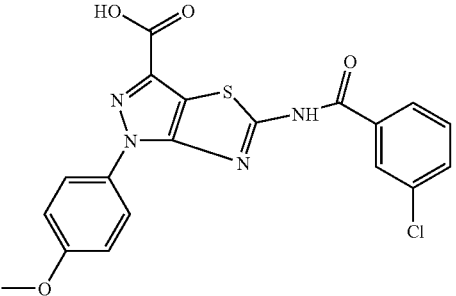 | Method C RT = 2.36 min | M + 1 = 429 |
| 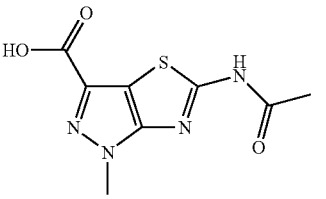 | Method C RT = 1.15 min | M + 1 = 241 |
| 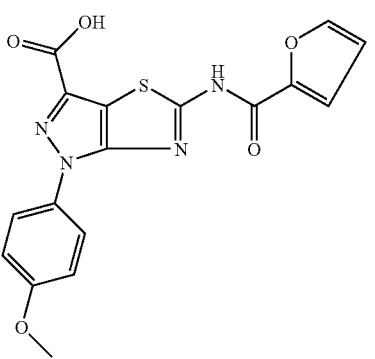 | Method C RT = 2.03 min | M + 1 = 385 |

TABLE 6-continued
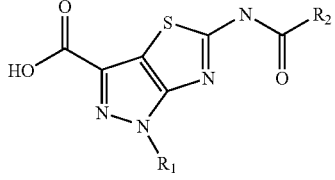
| Structure | LC | MS |
|---|---|---|
| 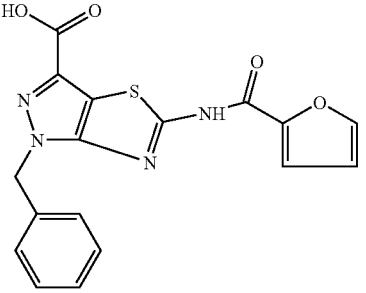 | Method C<br>RT = 2.01 min | M + 1 = 369 |
| 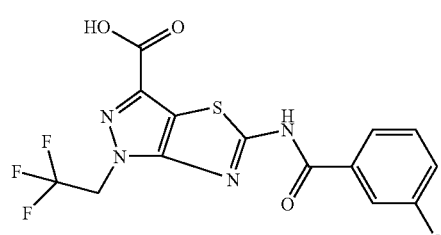 | Method C<br>RT = 2.16 min | M + 1 = 405 |
| 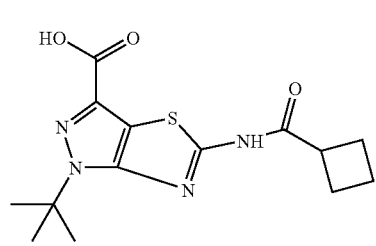 | Method C<br>RT = 1.19 min | M + 1 = 324 |
| 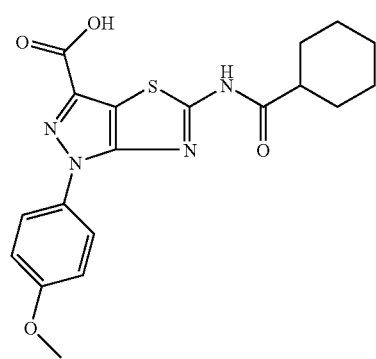 | Method C<br>RT = 2.21 min | M + 1 = 401 |

TABLE 6-continued
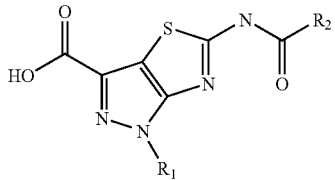
| Structure | LC | MS |
|---|---|---|
| 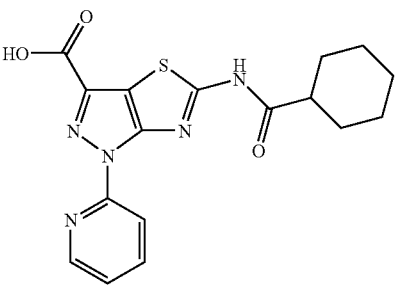 | Method C<br>RT = 2.23 min | M + 1 = 372 |
| 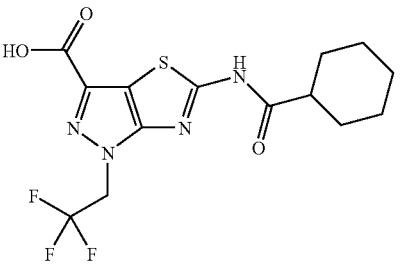 | Method C<br>RT = 1.94 min | M + 1 = 377 |
| 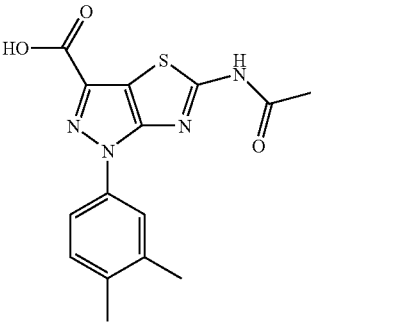 | Method C<br>RT = 1.99 min | M + 1 = 331 |
| 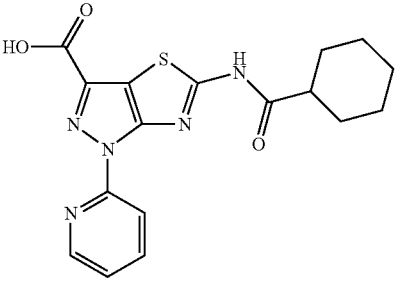 | Method C<br>RT = 2.23 | M + 1 = 372 |

TABLE 6-continued
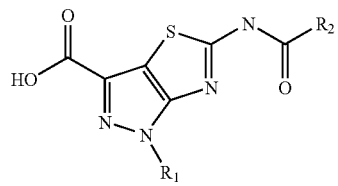
| Structure | LC | MS |
|---|---|---|
| | Method C RT = 2.12 min | M + 1 = 365 |
| | Method C RT = 1.69 min | M + 1 = 309 |
| | Method C RT = 1.73 min | M + 1 = 349 |
| | Method C RT = 1.93 min | M + 1 = 329 |
| | Method C RT = 2.14 min | M + 1 = 375 |

TABLE 6-continued
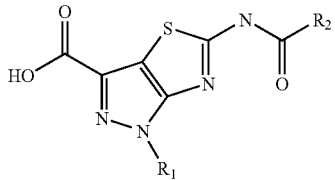
| Structure | LC | MS |
| --- | --- | --- |
| 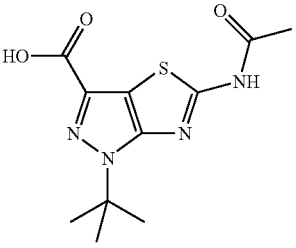 | Method C<br>RT = 1.54 min | M + 1 = 283 |
| 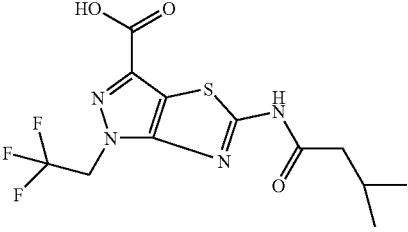 | Method C<br>RT = 1.79 min | M + 1 = 351 |
| 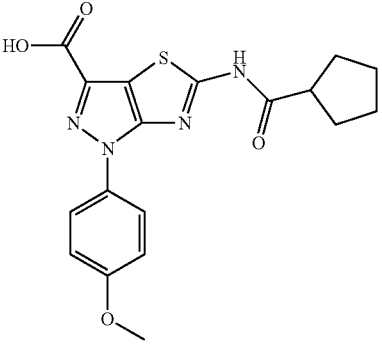 | Method C<br>RT = 2.09 min | M + 1 = 387 |
| 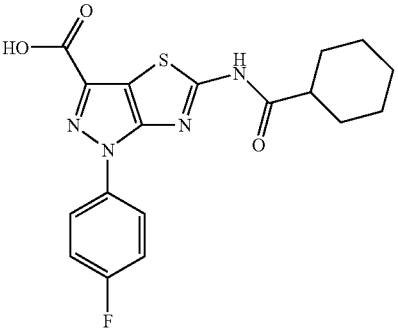 | Method C<br>RT = 2.23 min | M + 1 = 389 |

TABLE 6-continued
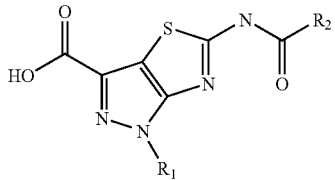
| Structure | LC | MS |
|---|---|---|
| 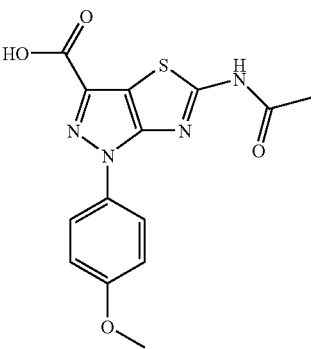 | Method C<br>RT = 1.76 min | M + 1 = 331 |
| 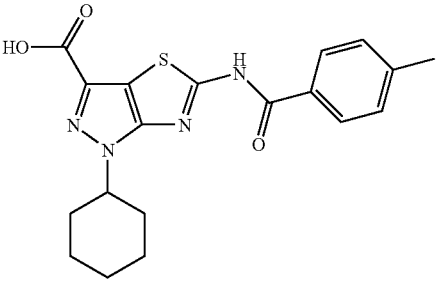 | Method C<br>RT = 2.17 min | M + 1 = 385 |
| 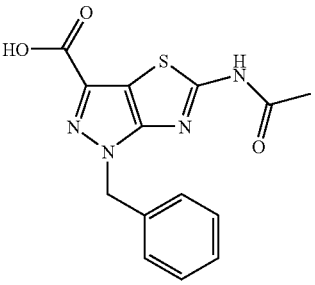 | Method C<br>RT = 1.58 min | M + 1 = 317 |
| 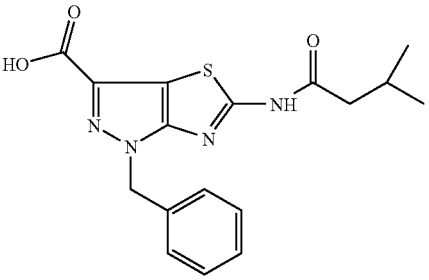 | Method C<br>RT = 1.93 min | M + 1 = 359 |

TABLE 6-continued

| Structure | LC | MS |
|---|---|---|
| 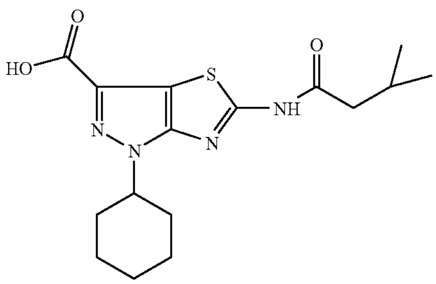 | Method C<br>RT = 2.0 min | M + 1 = 351 |
| 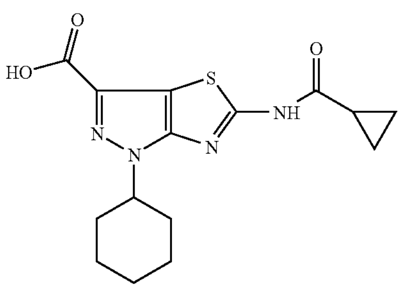 | Method C<br>RT = 1.85 min | M + 1 = 335 |
| 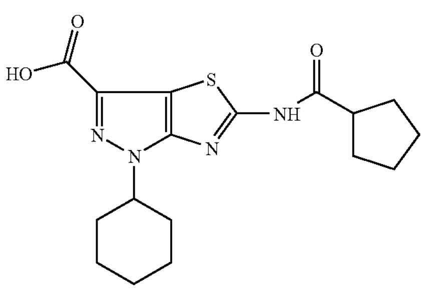 | Method C<br>RT = 2.03 min | M + 1 = 363 |
| 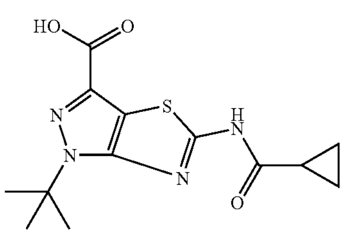 | Method C<br>RT = 1.73 min | M + 1 = 309 |

TABLE 6-continued
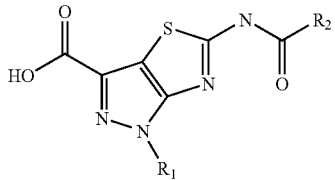
| Structure | LC | MS |
|---|---|---|
| 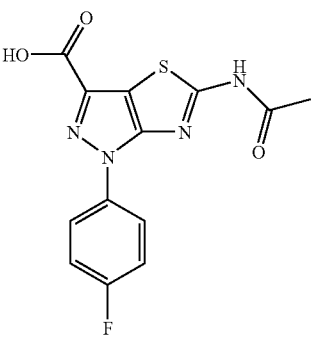 | Method C<br>RT = 1.81 min | M + 1 = 321 |
| 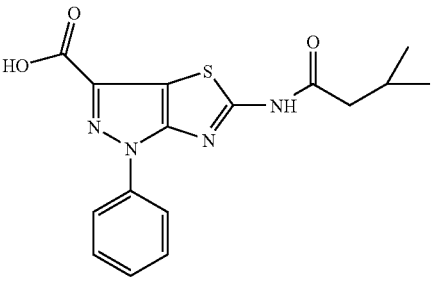 | Method C<br>RT = 2.04 min | M + 1 = 345 |
| 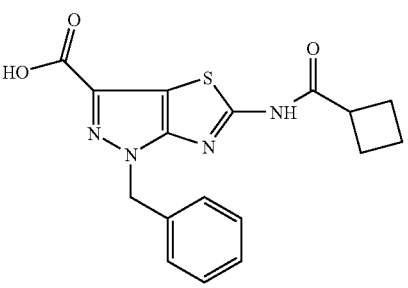 | Method C<br>RT = 1.88 min | M + 1 = 357 |
| 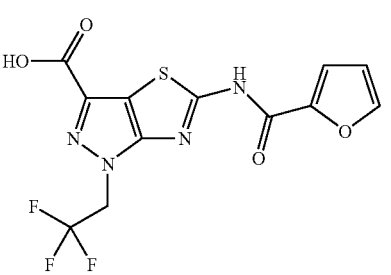 | Method C<br>RT = 1.69 min | M + 1 = 361 |

TABLE 6-continued
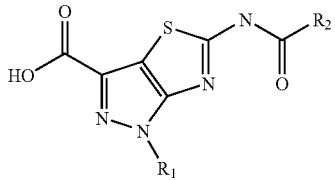
| Structure | LC | MS |
|---|---|---|
| 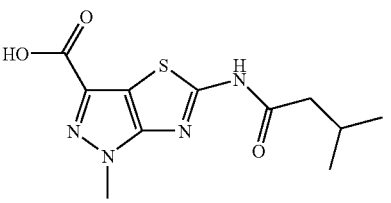 | Method C RT = 1.58 min | M + 1 = 283 |
| 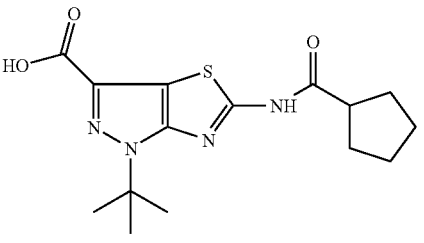 | Method C RT = 1.93 min | M + 1 = 337 |
| 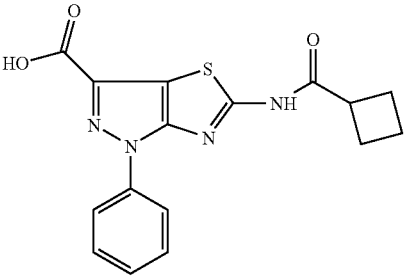 | Method C RT = 2.01 min | M + 1 = 343 |
| 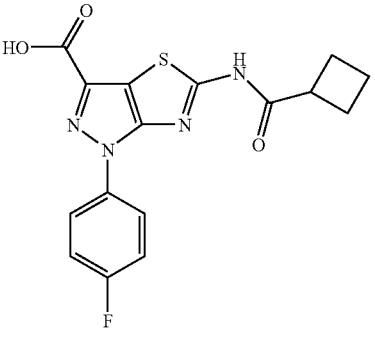 | Method C RT = 2.05 min | M + 1 = 361 |
| 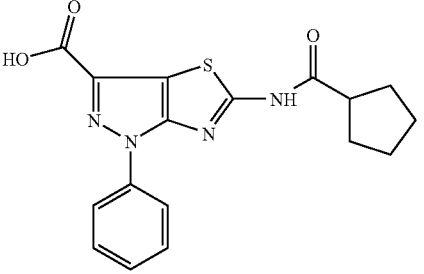 | Method C RT = 2.11 min | M + 1 = 357 |

TABLE 6-continued
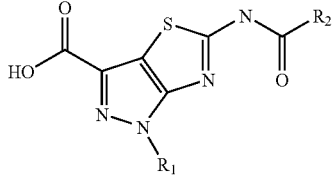
| Structure | LC | MS |
|---|---|---|
| 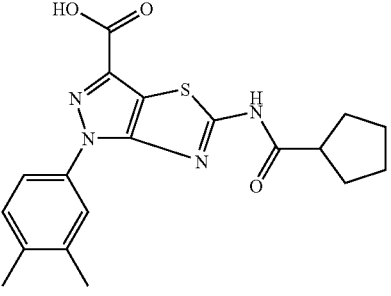 | Method C<br>RT = 2.28 min | M + 1 = 385 |
| 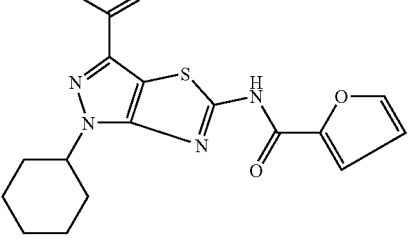 | Method C<br>RT = 1.92 min | M + 1 = 361 |
| 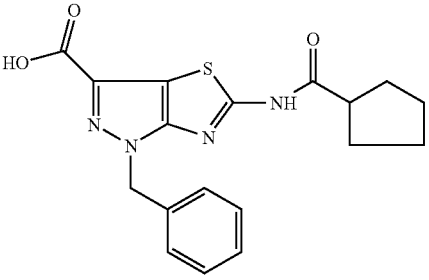 | Method C<br>RT = 1.98 min | M + 1 = 371 |
| 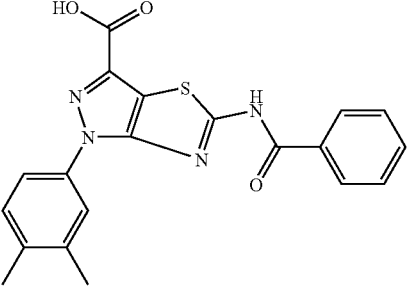 | Method C<br>RT = 2.18 min | M + 1 = 394 |

TABLE 6-continued

| Structure | LC | MS |
|---|---|---|
| | Method C RT = 2.33 min | M + 1 = 399 |
| | Method C RT = 2.09 min | M + 1 = 363 |
| | Method C RT = 2.40 | M + 1 = 447 |
| | Method C RT = 1.60 min | M + 1 = 335 |

TABLE 6-continued
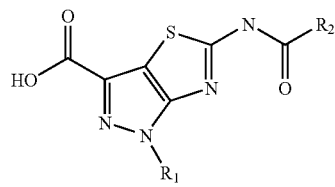
| Structure | LC | MS |
|---|---|---|
| | Method C RT = 2.01 min | M + 1 = 347 |
| | Method C RT = 2.17 min | M + 1 = 377 |
| | Method C RT = 2.26 min | M + 1 = 331 |
| | Method C RT = 2.22 min | M + 1 = 345 |
| | Method C RT = 1.42 min | M + 1 = 309 |

5.6 N-tert-Butyly-3-(2-methoxymethyl-pyrrolidine-1-carbonyl)-1H-pyrazolo[3,4-d]thiazol-5-yl]4-methyl-benzamide

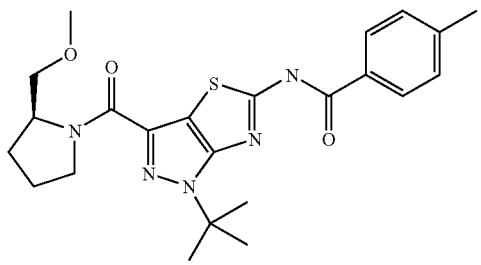

1-Tert-Butyl-5-(4-methyl-benzoylamino)-1H-pyrazolo[3,4-d]thiazole-3-carboxylic acid (50 mg, 0.14 mmoles) was dissolved in 10 ml of anhydrous tetrahydrofuran. Then, 1-hydroxybenzotriazole (23 mg, 0.168 mmoles) was added followed by addition of N-cyclohexylcarbodiimide N'-methyl polystyrene (155 mg, 0.28 mmoles, loading: 1.8 mmoles/g) and S-2-methoxymethylpyrrolidine (22 mg, 0.14 mmoles). The mixture was heated at 50° C. for overnight. Polymer supported trisamine (100 mg, 0.417 mmoles, loading: 4.17 mmoles/g) was added and shaken for 4 hours at 50° C. The resin was filtered off and washed with tetrahydrofuran (2×5 ml). The filtrate was evaporated in vacuo to give crude product, which was purified by preparative HPLC using MeOH/H$_2$O/TFA solvent system. The combined pure fractions were evaporated in vacuo and further dried on lyophilizer (yield: 36%, LC: Method A, RT=4.020 min, MS: M+1=456).

The compounds listed in Table 7, as well as those listed in Table 2, which are encompassed by the generic structure provided below, were prepared using similar procedures:

TABLE 7

| Structure | Analytical HPLC | LC-MS |
|---|---|---|
| 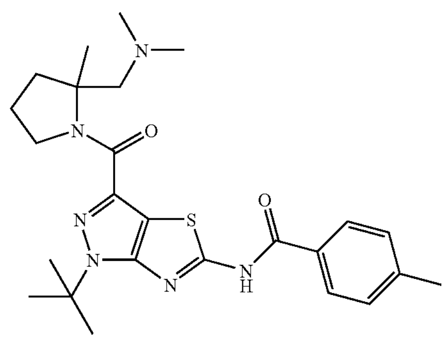 | Method A<br>RT = 3.566 min<br>Wavelength = 254 nm | M + 1 = 483 |
| 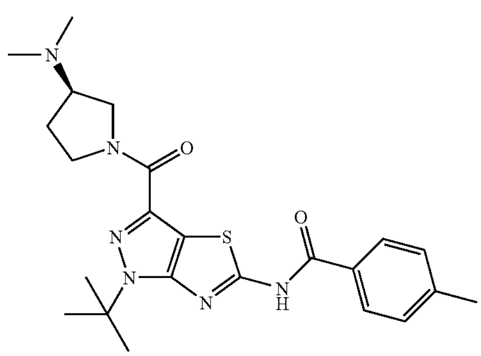 | Method A<br>RT = 3.143 min | M + 1 = 455 |

TABLE 7-continued

| Structure | Analytical HPLC | LC-MS |
|---|---|---|
| 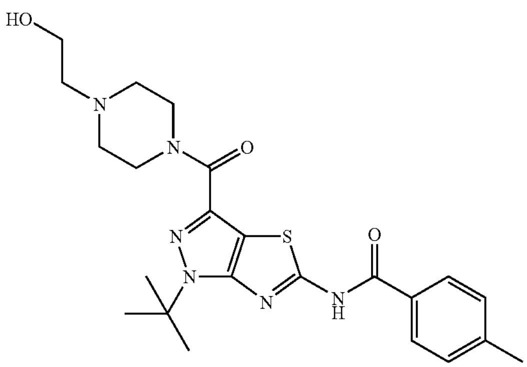 | Method A<br>RT = 3.040 min | M + 1 = 471 |
| 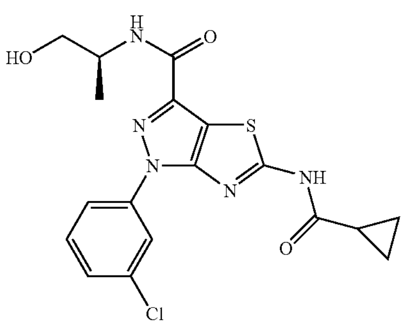 | Method C<br>RT = 1.856 min | M + 1 = 420 |
| 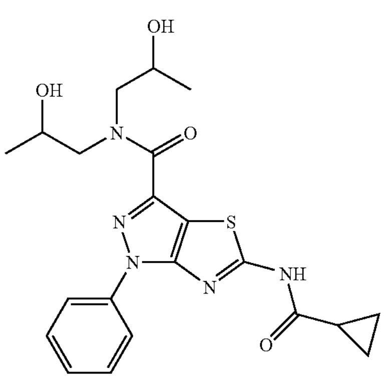 | Method C<br>RT = 1.719 min | M + 1 = 444 |

TABLE 7-continued

| Structure | Analytical HPLC | LC-MS |
|---|---|---|
| [structure] | Method C<br>RT = 1.585 min | M + 1 = 416 |
| [structure] | Method C<br>RT = 1.808 min | M + 1 = 414 |
| [structure] | Method C<br>RT = 1.751 min | M + 1 = 400 |

TABLE 7-continued

| Structure | Analytical HPLC | LC-MS |
|---|---|---|
| 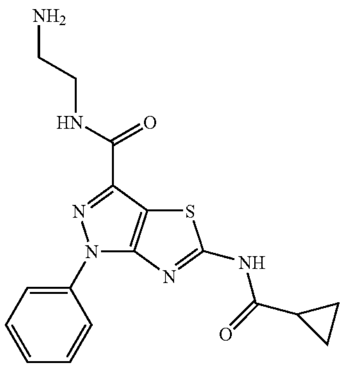 | Method C<br>RT = 1.452 min | M + 1 = 371 |
| 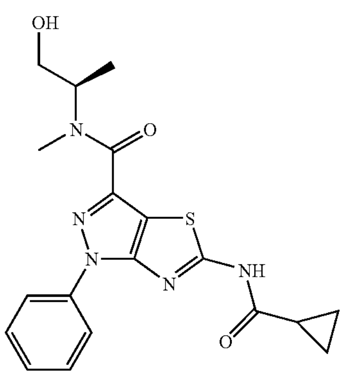 | Method C<br>RT = 1.712 min | M + 1 = 400 |
| 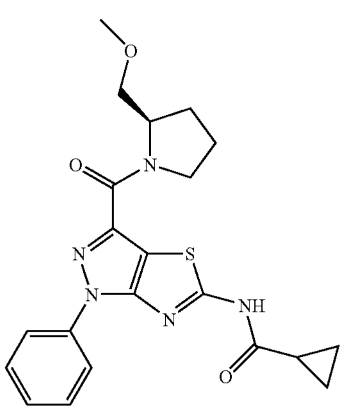 | Method B<br>RT = 5.560 min | M + 1 = 426 |

TABLE 7-continued

| Structure | Analytical HPLC | LC-MS |
|---|---|---|
| | Method B RT = 3.870 min | M + 1 = 460 |
| | Method B RT = 5.546 min | M + 1 = 385 |
| | Method B RT = 5.720 min | M + 1 = 440 |

TABLE 7-continued

| Structure | Analytical HPLC | LC-MS |
|---|---|---|
| | Method B<br>RT = 4.873 min | M + 1 = 431 |
| | Method B<br>RT = 4.610 min | M + 1 = 411 |
| | Method A<br>RT = 4.910 min | M + 1 = 442.1 |

TABLE 7-continued

| Structure | Analytical HPLC | LC-MS |
|---|---|---|
| CHIRAL (methoxy-methylpropyl pyrazolo-thiazole tert-butyl tolyl) | Method D RT = 3.890 min | M + 1 = 430.1 |
| (pyrrolidinyl-carbonyl pyrazolo-thiazole tert-butyl tolyl) | Method D RT = 4.106 min | M + 1 = 412.15 |
| CHIRAL (hydroxymethyl-pyrrolidinyl-carbonyl, trifluoroethyl-N pyrazolo-thiazole tolyl) | Method D RT = 3.643 min | M + 1 = 468.10 |
| CHIRAL (hydroxymethyl-pyrrolidinyl-carbonyl pyrazolo-thiazole tert-butyl phenyl) | Method D RT = 3.710 min | M + 1 = 428.20 |

TABLE 7-continued
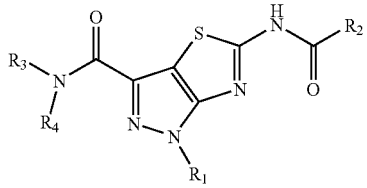
| Structure | Analytical HPLC | LC-MS |
|---|---|---|
| CHIRAL 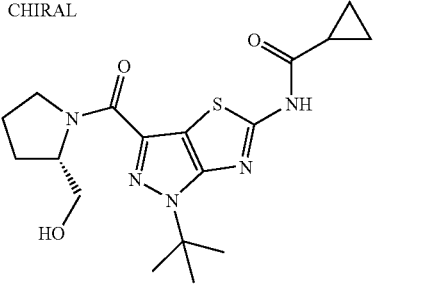 | Method D RT = 3.396 min | M + 1 = 392.20 |
| CHIRAL 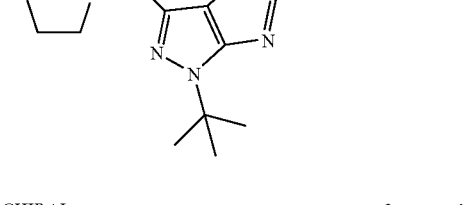 | Method D RT = 3.840 min | M + 1 = 434.20 |
| CHIRAL  | Method D RT = 3.900 min | M + 1 = 442.15 |
| CHIRAL | Method D RT = 3.643 min | M + 1 = 416.20 |

TABLE 7-continued
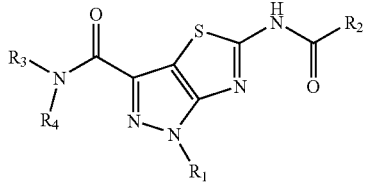
| Structure | Analytical HPLC | LC-MS |
|---|---|---|
| CHIRAL 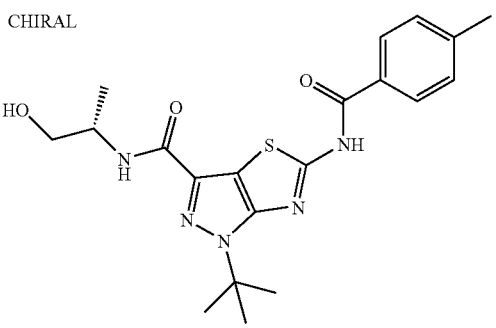 | Method D RT = 3.666 min | M + 1 = 416.20 |
| CHIRAL 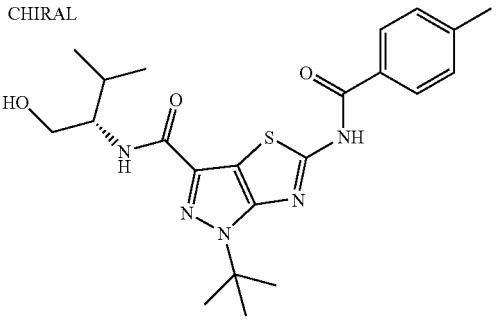 | Method A RT = 4.930 min | M + 1 = 444.1 |
| CHIRAL 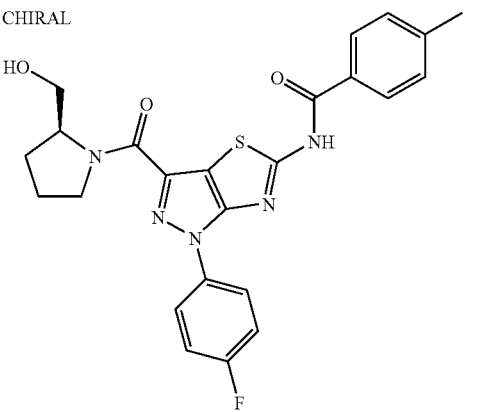 | Method A RT = 5.223 min | M + 1 = 480 |

TABLE 7-continued

| Structure | Analytical HPLC | LC-MS |
|---|---|---|
| 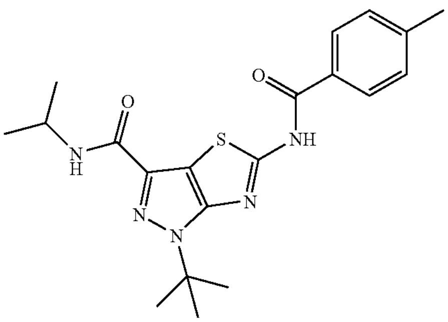 | Method A<br>RT = 5.026 min | M + 1 = 400.15 |
| CHIRAL | Method A<br>RT = 4.250 min | M + 1 = 400.1 |
| CHIRAL | Method A<br>RT = 4.910 min | M + 1 = 442.1 |
| 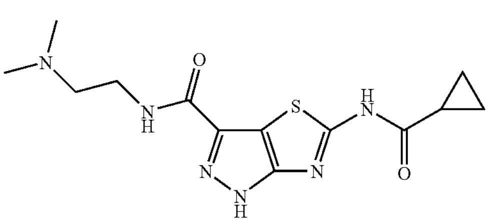 | Method C<br>RT = 1.24 min | M + 1 = 323 |
| 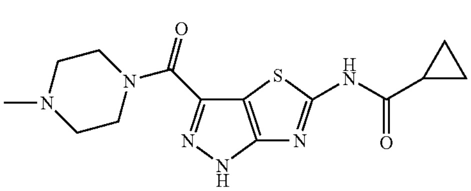 | Method C<br>RT = 1.20 min | M + 1 = 335 |

TABLE 7-continued

| Structure | Analytical HPLC | LC-MS |
|---|---|---|
| | Method C RT = 1.30 min | M + 1 = 343 |
| | Method C RT = 1.93 min | M + 1 = 338 |
| | Method C RT = 1.95 min | M + 1 = 335 |
| | Method C RT = 1.33 min | M + 1 = 296 |
| | Method C RT = 1.79 min | M + 1 = 292 |
| | Method C RT = 1.81 min | M + 1 = 336 |
| | Method C RT = 1.64 min | M + 1 = 280 |

TABLE 7-continued

| Structure | Analytical HPLC | LC-MS |
|---|---|---|
| (benzyl-NH-C(O)- pyrazolo-thiazole-NH-C(O)-cyclopropyl) | Method C RT = 2.38 min | M + 1 = 342 |
| (cyclohexyl-NH-C(O)- pyrazolo-thiazole-NH-C(O)-cyclopropyl) | Method C RT = 2.21 min | M + 1 = 334 |
| (H₂N-C(O)- pyrazolo-thiazole-NH-C(O)-cyclopropyl) | Method C RT = 1.43 min | M + 1 = 252 |
| (MeNH-C(O)- pyrazolo-thiazole-NH-C(O)-cyclopropyl) | Method C RT = 1.56 min | M + 1 = 266 |
| (pyrrolidine-C(O)- pyrazolo-thiazole-NH-C(O)-cyclopropyl) | Method C RT = 1.93 min | M + 1 = 306 |
| (piperidine-C(O)- pyrazolo-thiazole-NH-C(O)-cyclopropyl) | Method C RT = 1.80 min | M + 1 = 320 |
| (4-methylpiperazine-C(O)- pyrazolo-thiazole-NH-C(O)-methyl) | Method C RT = 0.88 min | M + 1 = 309 |

TABLE 7-continued
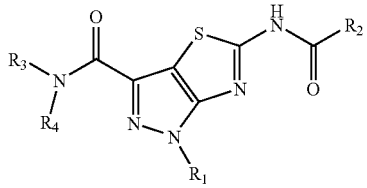
| Structure | Analytical HPLC | LC-MS |
|---|---|---|
| 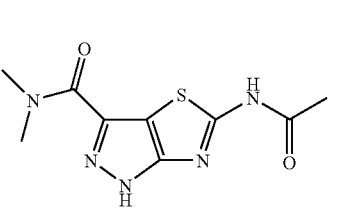 | Method C<br>RT = 1.02 min | M + 1 = 317 |
| 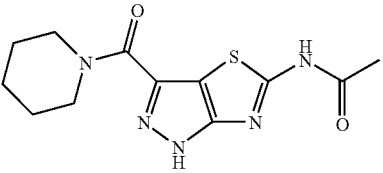 | Method C<br>RT = 1.33 min | M + 1 = 254 |
| 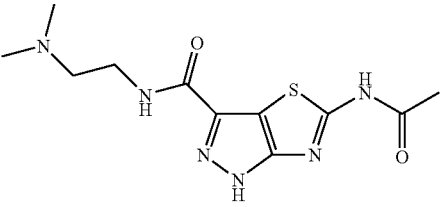 | Method C<br>RT = 1.57 min | M + 1 = 294 |
| 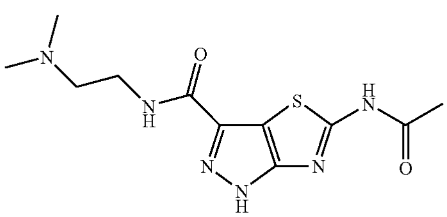 | Method C<br>RT = 0.95 min | M + 1 = 297 |
| 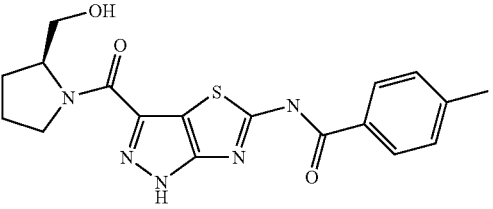 | Method C<br>RT = 1.84 min | M + 1 = 316 |
| 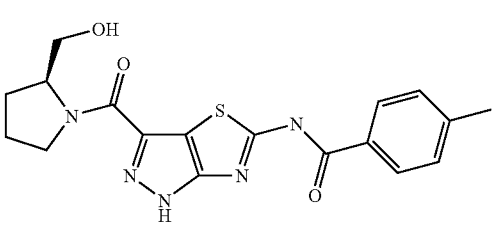 | Method C<br>RT = 1.68 min | M + 1 = 386 |

TABLE 7-continued

| Structure | Analytical HPLC | LC-MS |
|---|---|---|
| (structure) | Method C RT = 1.92 min | M + 1 = 400 |
| (structure) | Method C RT = 1.86 min | M + 1 = 328 |
| (structure) | Method C RT = 1.74 min | M + 1 = 342 |
| (structure) | Method C RT = 1.85 min | M + 1 = 356 |

TABLE 7-continued

| Structure | Analytical HPLC | LC-MS |
|---|---|---|
| (structure with 2-chlorophenyl and cyclopropanecarboxamide) | Method C<br>RT = 1.59 min | M + 1 = 420 |
| (structure with 4-sulfamoylphenyl and cyclopropanecarboxamide) | Method C<br>RT = 1.51 min | M + 1 = 465 |

5.7 4-Tert-Butyl-2-(4-methyl-benzoylamino)-4H-pyrrolo[2,3-d]thiazole-6-carboxylic acid(thiazol-2-ylmethyl)-amide A specific compound of the invention was prepared using the method described below:

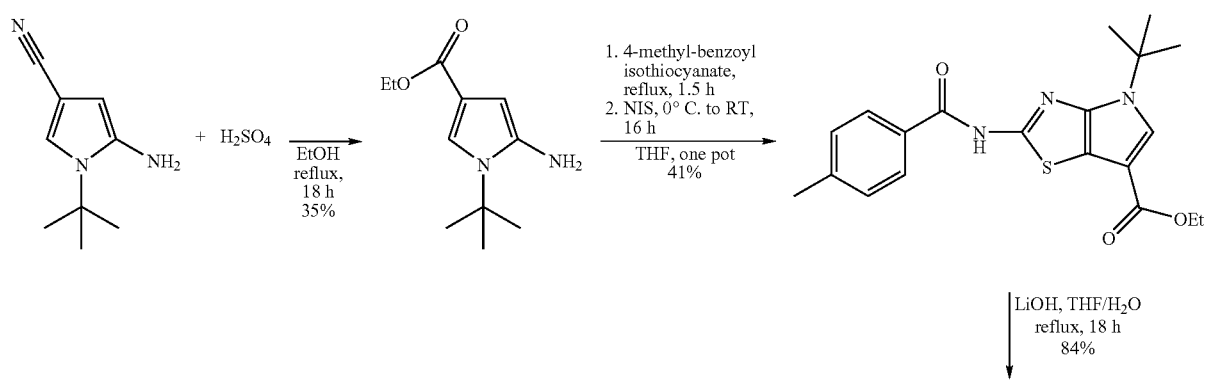

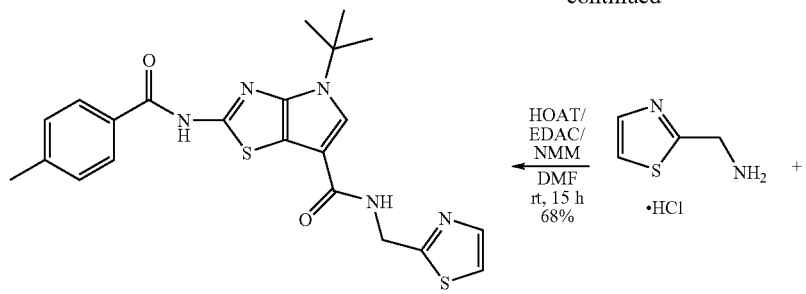

5.7.1 5-Amino-1-tert-butyl-1H-pyrrole-3-carboxylic acid ethyl ester

Surlfuric acid (conc., 61.0 mL) was slowly added to a well stirred, ambient temperature solution of 5-amino-v-tert-butyl-H-pyrrole-3-carbonitrile (12.2 g, 75.0 mmol) in ethanol (250 mL, HPLC grade, denatured), while spontaneously refluxed. When the reaction cooled below its boiling point, external heating was applied, and reaction was refluxed overnight for 18 hours. The solution was cooled, cautiously poured into a stirred aqueous 10% (w/v) sodium bicarbonate solution (1 L), and pH further adjusted to ca. 8 by addition of solid sodium bicarbonate. Crude product was extracted into ethyl acetate, dried $MgSO_4$), evaporated, and flash chromatographed (silica gel, 25% (v/v) EtOAc/hexanes) to obtain 5.6 g (35%) of the product as clear red oil. MS: M+H=211.

5.7.2 4-Tert-Butyl-2-(4-methyl-benzoylamino)-4H-pyrrolo[2,3-d]thiazole-6-carboxylic acid ethyl ester 4-Methyl-benzoyl isothiocyanate (4.5 ml, 29.5 mmol) was added neat, via syringe under $N_2$ blanket, to a stirred solution of 5-amino-1-tert-butyl-1H-pyrrole-3-carboxylic acid ethyl ester (5.6 g, 26.6 mmol) in anhydrous THF (270 ml), and brought to reflux for 1.5 hours. The solution was chilled to 0° C., then neat N-iodosuccinimide (6.6 g, 29.3 mmol) was added, and the solution was allowed to stir and warm to ambient temperature overnight for 16 hours. Reaction was slowly poured into a stirred 10% (w/v) sodium metabisulfite aqueous solution (200 ml), then extracted with ethyl acetate, dried ($MgSO_4$), and flash chromatographed (silica gel, 25% (v/v) EtOAc/hexanes). Isolated product was crystallized from ethyl acetate/hexanes to afford 4.2 g (41%) of white powder, mp. 200-201° C. MS:M+H=386.

5.7.4 4-Tert-Butyl-2-(4-methyl-benzoylamino)-4H-pyrrolo[2,3-d]thiazole-6-carboxylic acid Water (50 ml) was added to a stirred suspension of 4-tert-butyl-2-(4-methyl-benzoylamino)-4H-pyrrolo[2,3-d]thiazole-6-carboxylic acid ethyl ester (4.0 g, 10.5 mmol) and lithium hydroxide (1.0 g, 42.6 mmol) in THF (105 ml). The mixture was held at reflux for 18 hours, cooled, diluted with water (200 ml), and washed with ethyl acetate. The aqueous phase was chilled, then acidified (6M HCl), with stirring, to precipitate product. The solid was filtered and dried to yield 3.14 g (84%) of the product. MS: M+H=358.

5.7.5 4-Tert-Butyl-2-(4-methyl-benzoylamino)-4H-pyrrolo[2,3-d]thiazole-6-carboxylic acid(thiazol-2-ylmethyl)-amide Anhydrous N,N-dimethylformamide (30 ml) was added to a mixture of 4-tert-butyl-2-(4-methyl-benzoylamino)-4H-pyrrolo[2,3-d]thiazole-6-carboxylic acid (1.1g, 2.9 mmol), C-thiazol-2-yl-methylamine hydrochloride (0.5 g, 3.3 mmol), 1-hydroxy-7-azabenzotriazole (HOAt, 0.4 g, 2.9 mmol), N-(3-dimethylaminopropyl)-N'-ethylcarbodiimide hydrochloride (EDAC, 0.9 g, 4.4 mmol), and 4-methylmorpholine (NMM, 0.8 ml, 7.2 mmol). The resulting solution was stirred at ambient temperature, under $N_2$ blanket, for 15 hours, then slowly poured into 300 ml of rapidly stirred water. Precipitated solid was isolated by filtration, flash chromatographed (silica gel, 100% EtOAc), and then crystallized from ethyl acetate/hexanes to afford 0.9 g (68%) of the product as fine white crystalline powder, mp. 245-246° C. (decomp.). $^1$H NMR ($d_6$-DMSO): δ 1.72 ppm, s, 9H, 2.40 ppm, s, 3H, 4.73 ppm, d, j=6.0 Hz, 2H, 7.35 ppm, d, j=7.8 Hz, 2H; 7.63 ppm, d, j=3.3 Hz, 1H, 7.74 ppm, d, j=3.3 Hz, 1H, 7.85 ppm, s, 1H, 8.03 ppm, d, j=8.1 Hz, 2H, 8.92 ppm, t, j=6.0 Hz, 1H, 12.49 ppm, s, 1H. MS: M+H=454.

The compounds listed in Table 3 were synthesized using procedures similar to those described in Sections 5.7.1-5.7.5.

All of the patents, patent applications and publications referred to in this application are incorporated herein in their entireties. However, citation or identification of any reference in this application is not an admission that such reference is available as prior art to this invention. The full scope of the invention is better understood with reference to the appended claims.

What is claimed is:

1. A compound of formula:

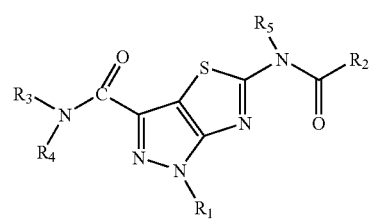

or a pharmaceutically acceptable salt, solvate, or stereoisomer thereof, wherein:

$R_1$, $R_3$ and $R_4$ are each independently H, optionally substituted alkyl, optionally substituted alkenyl, optionally substituted alkynyl, optionally substituted aryl, optionally substituted heteroaryl, optionally substituted heterocycloalkyl, optionally substituted heterocycle, optionally substituted arylalkyl, optionally substituted heterocycloalkylalkyl, optionally substituted heteroarylalkyl, optionally substituted alkoxycarbonyl, optionally substituted aminocarbonyl, optionally substituted carbonyl, or optionally substituted sulfonyl; or $R_3$ and $R_4$, with the nitrogen to which they are attached, form an optionally substituted heterocycle;

$R_2$ is H, optionally substituted alkyl, optionally substituted alkenyl, optionally substituted alkynyl, optionally substituted aryl, optionally substituted heteroaryl, optionally substituted heterocycloalkyl, optionally substituted heterocycle, optionally substituted arylalkyl, optionally substituted heterocycloalkylalkyl, or optionally substituted heteroarylalkyl; and $R_5$ is H, alkyl, heteroalkyl, heterocycloalkyl, alkyl or aryl carbonyl, or optionally substituted alkyl or aryl sulfonyl.

2. The compound of claim 1, wherein $R_3$ and $R_4$, with the nitrogen atom to which they are attached, form an optionally substituted heterocycle.

3. The compound of claim 2, wherein $R_3$ and $R_4$, with the nitrogen atom to which they are attached, form an optionally substituted pyrrolidine.

4. The compound of claim 1, wherein $R_5$ is H, and $R_2$ is lower alkyl.

5. The compound of claim 4, wherein $R_2$ is cyclopropyl.

6. The compound of claim 1, wherein $R_2$ and $R_5$ are both lower alkyl.

7. The compound of claim 1, wherein $R_5$ is H, and $R_2$ is aryl.

8. The compound of claim 7, wherein $R_2$ is phenyl.

9. The compound of claim 1, wherein $R_1$ is bunched alkyl.

10. The compound of claim 9, wherein $R_1$ is t-butyl.

11. The compound of claim 1, wherein $R_2$ is substituted or unsubstituted aryl.

12. The compound of claim 11, wherein $R_2$ is substituted or unsubstituted phenyl.

13. The compound of claim 1, wherein $R_1$ is t-butyl, ad $R_2$ is substituted or unsubstituted phenyl.

14. The compound of claim 1, which is stereomericaily pure.

15. A pharmaceutical composition comprising a compound of claim 1.

16. The pharmaceutical composition of claim 15, which further comprises a pharmaceutically acceptable carder or excipient.

17. A single dosage form comprising a compound of claim 1.

18. The dosage form of claim 17, which is suitable for oral, parenteral or transdermal administration.

* * * * *